(12) United States Patent
Rabinowitz et al.

(10) Patent No.: US 9,695,477 B2
(45) Date of Patent: *Jul. 4, 2017

(54) SYSTEM AND METHOD FOR CLEANING NOISY GENETIC DATA FROM TARGET INDIVIDUALS USING GENETIC DATA FROM GENETICALLY RELATED INDIVIDUALS

(71) Applicant: Natera, Inc., San Carlos, CA (US)

(72) Inventors: Matthew Rabinowitz, San Francisco, CA (US); Milena Banjevic, Los Altos Hills, CA (US); Zachary Demko, Los Altos Hills, CA (US); David Johnson, San Francisco, CA (US)

(73) Assignee: Natera, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/293,257

(22) Filed: Oct. 13, 2016

(65) Prior Publication Data

US 2017/0029893 A1    Feb. 2, 2017

Related U.S. Application Data

(63) Continuation of application No. 15/191,197, filed on Jun. 23, 2016, which is a continuation of application
(Continued)

(51) Int. Cl.
*G01N 33/48* (2006.01)
*G01N 31/00* (2006.01)
(Continued)

(52) U.S. Cl.
CPC ......... *C12Q 1/6883* (2013.01); *C12Q 1/6827* (2013.01); *C12Q 1/6876* (2013.01);
(Continued)

(58) Field of Classification Search
None
See application file for complete search history.

(56) References Cited

U.S. PATENT DOCUMENTS 5,635,366 A    6/1997 Cooke et al.
5,716,776 A    2/1998 Bogart
(Continued)

FOREIGN PATENT DOCUMENTS

EP    1524321 A1    4/2005
EP    1524321 B1    7/2009
(Continued)

OTHER PUBLICATIONS

"Blast of AAAAAAAAATTTAAAAAAAAATTT(http://blast.ncbi.nih.gov/Blast.cgi, downloaded May 4, 2015)".
(Continued)

*Primary Examiner* — Larry D Riggs, II

(57) ABSTRACT

A system and method for determining the genetic data for one or a small set of cells, or from fragmentary DNA, where a limited quantity of genetic data is available, are disclosed. Genetic data for the target individual is acquired and amplified using known methods, and poorly measured base pairs, missing alleles and missing regions are reconstructed using expected similarities between the target genome and the genome of genetically related subjects. In accordance with one embodiment of the invention, incomplete genetic data is acquired from embryonic cells, fetal cells, or cell-free fetal DNA isolated from the mother's blood, and the incomplete genetic data is reconstructed using the more complete genetic data from a larger sample diploid cells from one or both parents, with or without genetic data from haploid cells from one or both parents, and/or genetic data taken from other related individuals.

11 Claims, 16 Drawing Sheets

Related U.S. Application Data

No. 13/793,133, filed on Mar. 11, 2013, now Pat. No. 9,424,392, which is a continuation of application No. 11/603,406, filed on Nov. 22, 2006, now Pat. No. 8,532,930.

(60) Provisional application No. 60/846,610, filed on Sep. 22, 2006, provisional application No. 60/817,741, filed on Jun. 30, 2006, provisional application No. 60/789,506, filed on Apr. 4, 2006, provisional application No. 60/774,976, filed on Feb. 21, 2006, provisional application No. 60/754,396, filed on Dec. 29, 2005, provisional application No. 60/742,305, filed on Dec. 6, 2005, provisional application No. 60/739,882, filed on Nov. 26, 2005.

(51) Int. Cl.

| | | |
|---|---|---|
| *G06G 7/48* | (2006.01) | |
| *G06G 7/58* | (2006.01) | |
| *C12Q 1/68* | (2006.01) | |
| *G06F 19/20* | (2011.01) | |
| *G06F 19/18* | (2011.01) | |
| *G06F 19/22* | (2011.01) | |
| *G06F 19/24* | (2011.01) | |

(52) U.S. Cl.
CPC .............. *G06F 19/18* (2013.01); *G06F 19/20* (2013.01); *G06F 19/22* (2013.01); *G06F 19/24* (2013.01); *C12Q 2600/118* (2013.01); *C12Q 2600/156* (2013.01); *C12Q 2600/158* (2013.01)

(56) References Cited

U.S. PATENT DOCUMENTS

| | | |
|---|---|---|
| 5,753,467 A | 5/1998 | Jensen et al. |
| 5,824,467 A | 10/1998 | Mascarenhas |
| 5,860,917 A | 1/1999 | Comanor et al. |
| 5,972,602 A | 10/1999 | Hyland et al. |
| 5,994,148 A | 11/1999 | Stewart et al. |
| 6,001,611 A | 12/1999 | Will |
| 6,025,128 A | 2/2000 | Veltri et al. |
| 6,108,635 A | 8/2000 | Herren et al. |
| 6,143,496 A | 11/2000 | Brown et al. |
| 6,180,349 B1 | 1/2001 | Ginzinger et al. |
| 6,214,558 B1 | 4/2001 | Shuber et al. |
| 6,258,540 B1 | 7/2001 | Lo et al. |
| 6,300,077 B1 | 10/2001 | Shuber et al. |
| 6,440,706 B1 | 8/2002 | Vogelstein et al. |
| 6,479,235 B1 | 11/2002 | Schumm et al. |
| 6,489,135 B1 | 12/2002 | Parrott et al. |
| 6,720,140 B1 | 4/2004 | Hartley et al. |
| 6,807,491 B2 | 10/2004 | Pavlovic et al. |
| 6,852,487 B1 | 2/2005 | Barany et al. |
| 6,958,211 B2 | 10/2005 | Vingerhoets et al. |
| 7,035,739 B2 | 4/2006 | Schadt et al. |
| 7,058,517 B1 | 6/2006 | Denton et al. |
| 7,058,616 B1 | 6/2006 | Larder et al. |
| 7,218,764 B2 | 5/2007 | Vaisberg et al. |
| 7,297,485 B2 | 11/2007 | Bornarth et al. |
| 7,332,277 B2 | 2/2008 | Dhallan |
| 7,414,118 B1 | 8/2008 | Mullah et al. |
| 7,442,506 B2 | 10/2008 | Dhallan |
| 7,459,273 B2 | 12/2008 | Jones et al. |
| 7,645,576 B2 | 1/2010 | Lo et al. |
| 7,700,325 B2 | 4/2010 | Cantor et al. |
| 7,718,367 B2 | 5/2010 | Lo et al. |
| 7,718,370 B2 | 5/2010 | Dhallan |
| 7,727,720 B2 | 6/2010 | Dhallan |
| 7,805,282 B2 | 9/2010 | Casey |
| 7,838,647 B2 | 11/2010 | Hahn et al. |
| 7,888,017 B2 | 2/2011 | Quake |
| 8,008,018 B2 | 8/2011 | Quake et al. |
| 8,024,128 B2 | 9/2011 | Rabinowitz et al. |
| 8,137,912 B2 | 3/2012 | Kapur et al. |
| 8,168,389 B2 | 5/2012 | Shoemaker et al. |
| 8,195,415 B2 | 6/2012 | Fan et al. |
| 8,296,076 B2 | 10/2012 | Fan et al. |
| 8,304,187 B2 | 11/2012 | Fernando |
| 8,318,430 B2 | 11/2012 | Chuu et al. |
| 8,467,976 B2 | 6/2013 | Lo et al. |
| 8,515,679 B2 | 8/2013 | Rabinowitz et al. |
| 8,532,930 B2 | 9/2013 | Rabinowitz et al. |
| 8,682,592 B2 | 3/2014 | Rabinowitz et al. |
| 8,825,412 B2 | 9/2014 | Rabinowitz et al. |
| 2001/0053519 A1 | 12/2001 | Fodor et al. |
| 2002/0006622 A1 | 1/2002 | Bradley et al. |
| 2003/0009295 A1 | 1/2003 | Markowitz et al. |
| 2003/0065535 A1 | 4/2003 | Karlov et al. |
| 2003/0077586 A1 | 4/2003 | Pavlovic et al. |
| 2003/0101000 A1 | 5/2003 | Bader et al. |
| 2003/0228613 A1 | 12/2003 | Bornarth et al. |
| 2004/0033596 A1 | 2/2004 | Threadgill et al. |
| 2004/0137470 A1 | 7/2004 | Dhallan et al. |
| 2004/0197797 A1 | 10/2004 | Inoko et al. |
| 2004/0236518 A1 | 11/2004 | Pavlovic et al. |
| 2004/0259100 A1 | 12/2004 | Gunderson et al. |
| 2005/0009069 A1 | 1/2005 | Liu et al. |
| 2005/0049793 A1 | 3/2005 | Paterlini-brechot |
| 2005/0123914 A1 | 6/2005 | Katz et al. |
| 2005/0142577 A1 | 6/2005 | Jones et al. |
| 2005/0144664 A1 | 6/2005 | Smith et al. |
| 2005/0164241 A1 | 7/2005 | Hahn et al. |
| 2005/0221341 A1 | 10/2005 | Shimkets et al. |
| 2005/0227263 A1 | 10/2005 | Green et al. |
| 2005/0250111 A1 | 11/2005 | Xie et al. |
| 2005/0255508 A1 | 11/2005 | Casey et al. |
| 2005/0272073 A1 | 12/2005 | Vaisberg et al. |
| 2006/0019278 A1 | 1/2006 | Lo et al. |
| 2006/0040300 A1 | 2/2006 | Dapprich et al. |
| 2006/0052945 A1 | 3/2006 | Rabinowitz et al. |
| 2006/0057618 A1 | 3/2006 | Piper et al. |
| 2006/0068394 A1 | 3/2006 | Langmore et al. |
| 2006/0088574 A1 | 4/2006 | Manning et al. |
| 2006/0099614 A1 | 5/2006 | Gill et al. |
| 2006/0121452 A1 | 6/2006 | Dhallan |
| 2006/0134662 A1 | 6/2006 | Pratt et al. |
| 2006/0141499 A1 | 6/2006 | Sher et al. |
| 2006/0210997 A1 | 9/2006 | Myerson et al. |
| 2006/0216738 A1 | 9/2006 | Wada et al. |
| 2006/0229823 A1 | 10/2006 | Liu |
| 2006/0281105 A1 | 12/2006 | Li et al. |
| 2007/0027636 A1 | 2/2007 | Rabinowitz |
| 2007/0059707 A1 | 3/2007 | Cantor et al. |
| 2007/0122805 A1 | 5/2007 | Cantor et al. |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0259351 A1 | 11/2007 | Chinitz |
| 2008/0020390 A1 | 1/2008 | Mitchell |
| 2008/0026390 A1 | 1/2008 | Stoughton et al. |
| 2008/0038733 A1 | 2/2008 | Bischoff et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0102455 A1 | 5/2008 | Poetter |
| 2008/0138809 A1 | 6/2008 | Kapur et al. |
| 2008/0182244 A1 | 7/2008 | Tafas et al. |
| 2008/0193927 A1 | 8/2008 | Mann et al. |
| 2008/0234142 A1 | 9/2008 | Lietz |
| 2008/0243398 A1 | 10/2008 | Rabinowitz et al. |
| 2009/0023190 A1 | 1/2009 | Lao et al. |
| 2009/0029377 A1 | 1/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |

(56) References Cited

U.S. PATENT DOCUMENTS

| | | |
|---|---|---|
| 2009/0176662 A1 | 7/2009 | Rigatti et al. |
| 2009/0221620 A1 | 9/2009 | Luke et al. |
| 2010/0035232 A1 | 2/2010 | Ecker et al. |
| 2010/0112575 A1 | 5/2010 | Fan et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0138165 A1 | 6/2010 | Fan et al. |
| 2010/0171954 A1 | 7/2010 | Quake et al. |
| 2010/0184069 A1 | 7/2010 | Fernando et al. |
| 2010/0184152 A1 | 7/2010 | Sandler |
| 2010/0196892 A1 | 8/2010 | Quake et al. |
| 2010/0203538 A1 | 8/2010 | Dube et al. |
| 2010/0216153 A1 | 8/2010 | Lapidus et al. |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0285537 A1 | 11/2010 | Zimmermann |
| 2010/0291572 A1 | 11/2010 | Stoughton et al. |
| 2010/0323352 A1 | 12/2010 | Lo et al. |
| 2011/0033862 A1 | 2/2011 | Rabinowitz et al. |
| 2011/0039724 A1 | 2/2011 | Lo et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0151442 A1 | 6/2011 | Fan et al. |
| 2011/0178719 A1 | 7/2011 | Rabinowitz et al. |
| 2011/0201507 A1 | 8/2011 | Rava et al. |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0300608 A1 | 12/2011 | Ryan et al. |
| 2011/0301854 A1 | 12/2011 | Curry et al. |
| 2011/0318734 A1 | 12/2011 | Lo et al. |
| 2012/0003635 A1 | 1/2012 | Lo et al. |
| 2012/0034603 A1 | 2/2012 | Oliphant et al. |
| 2012/0122701 A1 | 5/2012 | Ryan et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0191358 A1 | 7/2012 | Oliphant et al. |
| 2012/0196754 A1 | 8/2012 | Quake et al. |
| 2012/0214678 A1 | 8/2012 | Rava et al. |
| 2012/0264121 A1 | 10/2012 | Rava et al. |
| 2012/0270212 A1 | 10/2012 | Rabinowitz et al. |
| 2013/0017549 A1 | 1/2013 | Hong |
| 2013/0024127 A1 | 1/2013 | Stuelpnagel |
| 2013/0034546 A1 | 2/2013 | Rava et al. |
| 2013/0060483 A1 | 3/2013 | Struble et al. |
| 2013/0069869 A1 | 3/2013 | Akao et al. |
| 2013/0090250 A1 | 4/2013 | Sparks et al. |
| 2013/0123120 A1 | 5/2013 | Zimmermann et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0252824 A1 | 9/2013 | Rabinowitz et al. |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0303461 A1 | 11/2013 | Iafrate et al. |
| 2013/0323731 A1 | 12/2013 | Lo et al. |
| 2014/0032128 A1 | 1/2014 | Rabinowitz et al. |
| 2014/0051585 A1 | 2/2014 | Prosen et al. |
| 2014/0065621 A1 | 3/2014 | Mhatre et al. |
| 2014/0087385 A1 | 3/2014 | Rabinowitz et al. |
| 2014/0094373 A1 | 4/2014 | Zimmermann et al. |
| 2014/0100126 A1 | 4/2014 | Rabinowitz |
| 2014/0100134 A1 | 4/2014 | Rabinowitz et al. |
| 2014/0141981 A1 | 5/2014 | Zimmermann et al. |
| 2014/0154682 A1 | 6/2014 | Rabinowitz et al. |
| 2014/0162269 A1 | 6/2014 | Rabinowitz et al. |
| 2014/0193816 A1 | 7/2014 | Rabinowitz et al. |
| 2014/0206552 A1 | 7/2014 | Rabinowitz et al. |
| 2014/0256569 A1 | 9/2014 | Rabinowitz et al. |
| 2014/0287934 A1 | 9/2014 | Szelinger et al. |
| 2014/0329245 A1 | 11/2014 | Spier et al. |
| 2014/0336060 A1 | 11/2014 | Rabinowitz |
| 2015/0051087 A1 | 2/2015 | Rabinowitz et al. |
| 2015/0064695 A1 | 3/2015 | Katz et al. |
| 2015/0072872 A1 | 3/2015 | Rabinowitz et al. |
| 2015/0147815 A1 | 5/2015 | Babiarz et al. |
| 2015/0232938 A1 | 8/2015 | Mhatre |
| 2015/0322507 A1 | 11/2015 | Zimmermann et al. |
| 2016/0244838 A1 | 8/2016 | Babiarz et al. |
| 2016/0357904 A1 | 12/2016 | Rabinowitz et al. |
| 2017/0011166 A1 | 1/2017 | Rabinowitz et al. |
| 2017/0051355 A1 | 2/2017 | Zimmermann et al. |

FOREIGN PATENT DOCUMENTS

| | | |
|---|---|---|
| EP | 2902500 A1 | 8/2015 |
| GB | 2488358 | 8/2012 |
| JP | 2965699 | 8/1999 |
| JP | 2002-530121 A | 9/2002 |
| JP | 2004502466 A | 1/2004 |
| JP | 2004533243 A | 11/2004 |
| JP | 2005514956 A | 5/2005 |
| JP | 2005160470 A | 6/2005 |
| JP | 2006-254912 A | 9/2006 |
| WO | 0179851 A1 | 10/2001 |
| WO | 0190419 A2 | 11/2001 |
| WO | 0204672 A2 | 1/2002 |
| WO | 02055985 A2 | 7/2002 |
| WO | 02076377 | 10/2002 |
| WO | 03031646 A1 | 4/2003 |
| WO | 03050532 A1 | 6/2003 |
| WO | 03062441 A1 | 7/2003 |
| WO | 0190419 A9 | 11/2003 |
| WO | 03102595 A1 | 12/2003 |
| WO | 03106623 A2 | 12/2003 |
| WO | 2004087863 A2 | 10/2004 |
| WO | 2005021793 A1 | 3/2005 |
| WO | 2005035725 A2 | 4/2005 |
| WO | 2005100401 A2 | 10/2005 |
| WO | 2005123779 A2 | 12/2005 |
| WO | 2007057647 A1 | 5/2007 |
| WO | 2007062164 A3 | 5/2007 |
| WO | 2007070482 A2 | 6/2007 |
| WO | 2007132167 A2 | 11/2007 |
| WO | 2007147074 A2 | 12/2007 |
| WO | 2008024473 A2 | 2/2008 |
| WO | 2008048931 A1 | 4/2008 |
| WO | 2008051928 A2 | 5/2008 |
| WO | 2008081451 A2 | 7/2008 |
| WO | 2008115497 A2 | 9/2008 |
| WO | 2008135837 A2 | 11/2008 |
| WO | 2008157264 A2 | 12/2008 |
| WO | 2009009769 A2 | 1/2009 |
| WO | 2009013492 A1 | 1/2009 |
| WO | 2009013496 A1 | 1/2009 |
| WO | 2009019215 A1 | 2/2009 |
| WO | 2009019455 A2 | 2/2009 |
| WO | 2009030100 A1 | 3/2009 |
| WO | 2009032779 A2 | 3/2009 |
| WO | 2009032781 A2 | 3/2009 |
| WO | 2009033178 A1 | 3/2009 |
| WO | 2009091934 A1 | 7/2009 |
| WO | 2009092035 A2 | 7/2009 |
| WO | 2009105531 A1 | 8/2009 |
| WO | 2009146335 A1 | 12/2009 |
| WO | 2010017214 A1 | 2/2010 |
| WO | 2010075459 | 7/2010 |
| WO | 2011041485 A1 | 4/2011 |
| WO | 2011057094 | 5/2011 |
| WO | 2011087760 | 7/2011 |
| WO | 2011146632 A1 | 11/2011 |
| WO | 2012071621 | 6/2012 |
| WO | 2012083250 | 6/2012 |
| WO | 2012088456 A2 | 6/2012 |
| WO | 2012108920 A1 | 8/2012 |

(56) References Cited

FOREIGN PATENT DOCUMENTS

| WO | 2012/142531 A2 | 10/2012 |
|---|---|---|
| WO | 2013030577 | 3/2013 |
| WO | 2013052557 A2 | 4/2013 |
| WO | 2013130848 | 9/2013 |
| WO | 2014018080 | 1/2014 |
| WO | 2015/164432 A1 | 10/2015 |

OTHER PUBLICATIONS

"CompetitivePCR Guide.", TaKaRa Biomedicals, Lit. # L0126 Rev. Aug. 1999, 9 pgs.
"db SNP rs2056688 (http://www.ncbi.nlm.nih.gov/projects/SNP/snp_ref.cgi?rs=2056688, downloaded May 4, 2015".
"Declaration by Dr Zimmerman of Oct. 30, 2014 filed in U.S. Appl. No. 14/044,434".
"European Application No. 014198110, European Search Report Mailed Apr. 28, 2015, 3 pages".
"Finishing the Euchromatic Sequence of the Human Genome", Nature vol. 431, (Oct. 21, 2004), 931-945.
"FixedMedium, dictionary definition, Academic Press Dictionary of Science andTechnology", Retrieved from the Internet: <URL:www.credoreference.com/entry/apdst/fixed_medium>, 1996, 1 pg.
"GeneticsHome Reference", http://ghr.nlm.nih.gov/handbook/genomicresearch/snp, Feb. 28, 2014, 1-2.
"Guideline related to genetic examination", Societies Related to Genetic Medicine, Japanese Society for Genetic Counseling, Japanese Society for Gene Diagnosis and Therapy, Japan Society of Obstetrics an, 2003, 2-15.
"How ManyCarbs in a Potato?, [Online]", Retrieved from theInternet:<http://www.newhealthguide.org/How-Many-Carbs-In-A-Potato.html>, Nov. 1, 2014, 3 pgs.
"Ion Ampli Seq Comprehensive Cancer Panel, product brochure, Life TechnologiesCorporation. Retrieved from the Internet", <URL:https://tools.lifetechnologies.com/content/sfs/brochures/Ion_CompCancerPanel_Flyer.pdf>, 2012, 2 pgs.
"IonAmpliSeq Designer Provide Full Flexibility to Sequence Genes of Your Choice,product brochure, Life Technologies Corporation", Retrieved from the Internet<URL: http://tools.lifetechnologies.com/content/sfs/brochures/IonAmpliSeq_CustomPanels_AppNote_CO1.
"Merriam-Webster.com (http://www.merriam-webster.com/dictionary/universal, downloaded Jul. 23, 2014)".
"Multiplexing with RainDrop Digital PCR", RainDance Technologies, Application Note, 2013, 1-2.
"NucleicAcids, Linkers and Primers: Random Primers", New England BioLabs 1998/99Catalog. 1998, 121 and 284.
"PRIMER3, information sheet, Sourceforge.net. [retrieved on Nov. 12, 2012]. Retrieved from the Internet: <URL: http://primer3.sourceforge.net/>", 2009, 1 pg.
"www.fatsecret.com" (printed from internet Nov. 1, 2014).
International Application Serial No. PCT/US14/51926, international Search Report and Written Opinion mailed Dec. 9, 2014, 5 pgs.
PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010).
The Bump (Panorama Test, attached, Jul. 1, 2013).
What to Expect (Weird Harmony results, attached, May 1, 2015).
Wikipedia (attached, available at https://en.wikipedia.org/wiki/Stimulant, accessed Mar. 14, 2016).
Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.
Agarwal, Ashwin et al., "Commercial Landscape of Noninvasive Prenatal Testing in the United States", Prenatal Diagnosis,33, 2013, 521-531.

Alkan, Can et al., "Personalized Copy Number and Segmental Duplication Maps Using Next-Generation Sequencing", Nature Genetics, 41, 10, 2009, 1061-1068.
Allaire, F. R., "Mate selection by selection index theory", Theoretical Applied Genetics, 57(6). 1980, 267-272.
Allawi, Hatim T. et al., "Thermodynamics of internal C•T Mismatches in DNA", Nucleic Acids Research, 26 (11), 1998, 2694-2701.
Aoki, Yasuhiro, "Statistical and Probabilistic Bases of Forensic DNA Testing", The Journal of the Iwate Medical Association, 2002, vol. 54, p. 81-94.
Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.
Ashoor, Ghalia et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.
Bada, Michael A. et al., "Computational Modeling of Structural Experimental Data", Methods in Enzymology,317, 2000, 470-491.
Beaumont, Mark A. et al., "The Bayesian Revolution in Genetics", Nature Reviews Genetics, 5, 2004, 251-261.
Beer, Alan E. et al., "The Biological Basis of Passage of Fetal Cellular Material into the Maternal Circulation", Annals New York Academy of Sciences, 731, 1994, 21-35.
Beerenwinkel, et al., "Methods for Optimizing Antiviral Combination Therapies", Bioinformatics, 19(1), 2003, i16-i25.
Beerenwinkel, N. et al., "Geno2pheno. estimating phenotypic drug resistance from HIV-1 genotypes", Nucleic Acids Research, 31(13), 2003, 3850-3855.
Benn, P. et al., "Non-Invasive Prenatal Testing for Aneuploidy: Current Status and Future Prospects", Ultrasound Obstet Gynecol, 42, 2013, 15-33.
Benn, P. et al., "Non-Invasive prenatal Diagnosis for Down Syndrome: the Paradigm Will Shift, but Slowly", Ultrasound Obstet. Gynecol., 39, 2012, 127-130.
Bentley, David R. et al., "Accurate Whole Human Genome Sequencing Using Reversible Terminator Chemistry", Nature, 456, 6, 2008, 53-59.
Bermudez, M. et al., "Single-cell sequencing and mini-sequencing for preimplantation genetic diagnosis", Prenatal Diagnosis, 23, 2003, 669-677.
Bevinetto, Gina, Bevinetto (5 Foods All Pregnant Women Need, American Baby, available at http://www.parents.com/pregnancy/mybody/nutrition/5greatpregnancyfoods/, Apr. 15, 2008).
Bianci, D. W. et al., "Fetal gender and aneuploidy detection using fetal cells maternal blood: analysis of NIFTY 1 data", Prenat Diagn 2002, 22, 2002, 609-615.
Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.
Bisignano, et al., "PGD and Aneuploidy Screening for 24 Chromosomnes: Advantages and Disadvantages of Competing Platforms", Reproductive BioMedicine Online, 23, 2011, 677-685.
Bodenreider, O., "The Unified Medical Language System (UMLS), Integrating Biomedical Terminology", Nucleic Acids Research, 32, (Database issue), 2004, D267-D270.
Breithaupt, Holger, "The Future of Medicine", EMBO Reports, 21(61), 2001, 465-467.
Brownie, Jannine et al., "The Elimination of Primer-Dimer Accumulation in PCR", Nucleic Acids Research, 25(16), 1997, 3235-3241.
Cairns, Paul et al., "Homozygous Deletions of 9p21 in Primary Human Bladder Tumors Detected by Comparative Multiplex Polymerase Chain Reaction", Cancer Research, 54, 1994, 1422-1424.
Caliendo, Angela, "Multiplex PCR and Emerging Technologies for the Detection of Respiratory Pathogens", Clinical Infectious Diseases, 52(4), 2011, S326-S330.
Carnevale, Alessandra et al., "Attitudes of Mexican Geneticists Towards Prenatal Diagnosis and Selective Abortion", American Journal of Medical Genetics, 75, 1998, 426-431.

(56) References Cited

OTHER PUBLICATIONS

Chakraborty, R. et al., "Paternity Exclusion by DNA Markers: Effects of Paternal Mutations", Journal of Forensic Sciences, vol. 41, No. 4, Jul. 1996, 671-677.
Chen, E. et al., "Noninvasive Prenatal Diagnosis of Fetal Trisomy 18 and Trisomy 13 by Maternal Plasma DNA Sequencing", PLoS ONE, 6(7), e21791, 2011, 7 pgs.
Chetty, Shilpa et al., "Uptake of Noninvasive Prenatal Testing (NIPT) in Women Following Positive Aneuploidy Screening", Prenatal Diagnosis,33, 2013, 542-546.
Chiu, R. et al., "Non-Invasive Prenatal Assessment of Trisomy 21 by Multiplexed Maternal Plasma DNA Sequencing: Large Scale Validity Study", BMJ, 342, C7401, 2011, 9 pgs.
Chiu, Rossa W. et al., "Effects of Blood-Processing Protocols on Fetal and Total DNA Quantification in Maternal Plasma", Clinical Chemistry, 47(9), 2001, 1607-1613.
Chiu, Rossa W.K. et al., "Maternal Plasma DNA Analysis with Massively Parallel Sequencing by Litigation for Noninvasive Prenatal Diagnosis of Trisomy 21", Clinical Chemistry, 56, 3, 2010, 459-463.
Chiu, Rossa W.K. et al., "Noninvasive Prenatal Diagnosis of Fetal Chromosome Aneuploidy by Massively Parallel Genomic Sequencing of DNA in Maternal Plasma", PNAS, 105, 51 (with Supporting Information), 2008, 23.
Chiu, Rossa W.K. et al., "Non-Invasive Prenatal Diagnosis by Single Molecule Counting Technologies", Trends in Genetics, 25 (7), 2009, 324-331.
Chu, T. et al., "Statistical Considerations for Digital Approaches to Non-Invasive Fetal Genotyping", Bioinformatics (Advance Access publication), 26 (22), 2010, 2863-2866.
Chu, Tianjiao et al., "Statiustical Model for Whole Genome Sequencing and its Applications to Minimally Invasive Diagnosis of Fetal Genetic Disease", Bioinformatics, 25(10), 2009, 1244-1250.
Chu, Tianjiao et al., "A Novel Approach Toward the Challenge of Accurately Quantifying Fetal DNA in Maternal Plasma", Prenatal Diagnosis,30, 2010, 1226-1229.
Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.
Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.
Cossu, Gianfranco et al., "Rh D/d Genotyping by Quantitative Polymerase Chain Reaction and Capillary Zone Electrophoresis", Electrophoresis, 17, 1996, 1911-1915.
Coyle, J.F. et al., "Standards for detailed clinical models as the basis for medical data exchange and decision support", International Journal of Medical Informatics, 69(2-3), 2003, 157-174.
Cross, Jillian et al., "Resolution of trisomic mosaicism in prenatal diagnosis: estimated performance of a 50K SNP microarray", Prenat Diagn 2007;27, 2007, 1197-1204.
D'Aquila, Richard et al., "Maximizing sensitivity and specificity of PCR by pre-amplification heating", Nucleic Acids Research, 19(13), 1991, p. 3749.
Daruwala, Raoul-Sam et al., "A Versatile Statistical Analysis Algorithm to Detect Genome Copy Number Variation", PNAS, 101(46), 2004, 16292-16297.
De Vries, et al., "Diagnostic genome profiling in mental retardation", Am J Hum Genet, 77, published online Aug. 30, 2005, 2005, 606-616.
DeAngelis, M. et al., "Solid-phase Reversible Immobilization for the Isolation of PCR Products", Nucleic Acids Research, 23 (22), 1995, 4742-4743.
Devaney, S. et al., "Noninvasive Fetal Sex Determination Using Cell-Free Fetal DNA: A Systematic Review and Meta-Analysis", JAMA, 306(6), 2011, 627-636.
Dhallan, et al., "Methods to Increase the Percentage of Free Fetal DNA Recovered from the Maternal Circulation", JAMA, 291(9), 2004, 1114-1119.
Dhallan, Ravinder et al., "A non-invasive test for prenatal diagnosis based on fetal DNA present in maternal blood: a preliminary study", The Lancet, 369, 2007, 474-481.
Dieffenbach, C.W. et al., "General concepts for PCR primer design", Genome Research, PCR methods and Applications vol. 3, 1993, S30-S37.
Ding, C. et al., "Direct molecular haplotyping of long-range genomic DNA with M1-PCR", PNAS 100(13), 2003, 7449-7453.
Dohm, J. et al., "Substantial Biases in Ultra-Short Read Dta Sets From High-Throughput DNA Sequencing", Nucleic Acids Research, 36(16), e105, 2008, 10 pgs.
Dolganov, Gregory et al., "A Novel Method of Gene Transcript Profiling in Airway Biopsy Homogenates Reveal Increased Expression of a Na—K+—Cl-Cotransporter (NKCC1) in Asthmatic Subjects", Genome Res.,11, 2001, 1473-1483.
Donohoe, Gerard G. et al., "Rapid Single-Tube Screening of the C282Y Hemochromatosis Mutation by Real-Time Multiplex Allele-specific PCR without Fluorescent Probes", Clinical Chemsitry, 46, 10, 2000, 1540-1547.
Donoso, P. et al., "Current Value of Preimplantation Genetic Aneuploidy Screening in IVF", Human Reproduction Update, 13(1), 2007, 15-25.
Echeverri, et al., "Caffeine's Vascular Mechanisms of Action", International Journal of Vascular Medicine vol. 2010(2010), 10 pages, Aug. 25, 2010.
Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.
Eichler, H., "Mild Course of Fetal Rh D Haemolytic Disease due to Maternal Alloimmunisation to Paternal HLA Class I and II Antigens", Vox Sang, 68, 1995, 243-247.
Ellison, Aaron M., "Bavesian Inference in Ecology", Ecology Letters, 2004, vol. 7, p. 509-520.
Ellonen, P. et al., "Development of SNP Microarray for Supplementary Paternity Testing", International Congress Series,1261, 2004, 12-14.
EP06838311.6, "European Communication and Extended European Search Report", mailed Dec. 30, 2008, 8 pgs.
EP08742125.1, "European Communication pursuant to Article 94(3) EPC and Examination Report", mailed Feb. 12, 2010, 5 pgs.
Fan, et al., "Whole-genome molecular haplotyping of single cells", Nature Biotechnology, vol. 29, No. 1, Jan. 1, 2011, 51-57.
Fan, Christina H. et al., "Non-Invasive Prenatal Measurement of the Fetal Genome", Nature, doi: 10.1038/nature11251, 2012, 26 pgs.
Fan, Christina H. et al., "Noninvasive Diagnosis of Fetal Aneuploidy by Shotgun Sequencing DNA from Maternal Blood", PNAS, 105, 42, 2008, 16266-16271.
Fan, Jian-Bing et al., "Highly-Parallel Genomic Assay", Nature Reviews, 7, 2006, 632-644.
Fazio, Gennaro et al., "Identification of RAPD Markers Linked to Fusarium Crown and Root Rot Resistance (Frl) in Tomato", Euphytica 105, 1999, 205-210.
Fiorentino, F. et al., "Development and Clinical Application of a Strategy for Preimplantation Genetic Diagnosis of Single Gene Disorders Combined with HLA Matching", Molecular Human Reproduction (Advance Access Publication), 10 (6), 2004, 445-460.
Fiorentino, F et al., "Strategies and Clinical Outcome of 250 Cycles of Preimplantation Genetic Diagnosis for Single Gene Disorders", Human Reproduction, 21, 3, 2006, 670-684.
Fiorentino, Francesco et al., "Short Tandem Repeats Haplotyping of the HLA Region in Preimplantation HLA Matching", European Journal of Human Genetics, 13, 2005, 953-958.
Forejt, et al., "Segmental trisomy of mouse chromosome 17: introducing an alternative model of Down's syndrome", Genomics, 4(6), 2003, 647-652.
Forshew, et al., "Noninvasive Identification and Monitoring of Cancer Mutations by Targeting Deep Sequencing of Plasma DNA",

(56) References Cited

OTHER PUBLICATIONS

Noninvasive identification and monitoring of cancer mutations by targeted deep sequencing of plasma DNA. Sci. Transl. Med. 4, 136 30 (2012)., 1-12.
Frederiksson, et al., "Multiplex amplification of all coding sequences within 10 cancer genes by Gene-Collector", Nucleic Acids Research, 2007, vol. 35, No. 7 e47, 1-6.
Freeman, Jennifer L. et al., "Copy Number Variation: New Insights in Genome Diversity", Genome Research, 16, 2006, 949-961.
Frost, Mackenzie S. et al., "Differential Effects of Chronic Pulsatile Versus Chronic Constant Maternal Hyperglycemia on Fetal Pancreatic B-Cells", Journal of Pregnancy, 2012,, Article ID 812094, 2012, 8.
Ganshirt-Ahlert, D. et al., "Ratio of Fetal to Maternal DNA is Less Than 1 in 5000 at different Gestational Ages in Maternal Blood", Clinical Genetics,38, 1990. 38-43.
Ganshirt-Ahlert, D. et al., "Fetal DNA in Uterine Vein Blood", Obstetrics & Gynecology, 80 (4), 1992, 601-603.
Ganshirt-Ahlert, Dorothee et al., "Three Cases of 45,X/46,XYnf Mosaicism", Human Genetics, 76, 1987, 153-156.
Gardina, P. et al., "Ploidy Status and Copy Number Abberations in Primary Glioblastomas Defined by Integrated Analysis of Allelic Ratios, Signal Ratios and Loss of Heterozygosity Using 500K SNP Mapping Arrays", BMC Genomics, 9 (489), (doi:10.1186/1471-2164-9-489), 2008, 16 pgs.
Ghanta, Sujana et al., "Non-Invasive Prenatal Detection of Trisomy 21 Using Tandem Single Nucleotide Polymorphisms", PLoS ONE, 5 (10), 2010, 10 pgs.
Gjertson, David W. et al., "Assessing Probability of Paternity and the Product Rule in DNA Systems", Genetica, 96, 1995, 89-98.
Greenwalt, T. et al., "The Quantification of Fetomaternal Hemorrhage by an Enzyme-Linked Antibody Test with Glutaraldehyde Fixation", Vox Sang, 63, 1992, 268-271.
Guerra, J., "Terminal Contributions for Duplex Oligonucleotide Thermodynamic Properties in the Context of Nearest Neighbor Models", Biopolymers, 95(3), (2010), 2011, 194-201.
Guetta, Esther et al., "Analysis of Fetal Blood Cells in the Maternal Circulation: Challenges, Ongoing Efforts, and Potential Solutions", Stem Cells and Development, 13, 2004, 93-99.
Guichoux, et al., "Current Trends in Microsatellite Genotyping", Molecular Ecology Resources, 11, 2011, 591-911.
Hall, M., "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Dec. 8, 2014].
Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.
Hara, Eiji et al., "Subtractive eDNA cloning using oligo(dT)3o-latex and PCR: isolation of eDNA clones specific to undifferentiated human embryonal carcinoma cells", Nucleic Acids Research, 19(25), 1991, 7097-7104.
Hardenbol, P., "Multiplexed Genotyping With Sequence-Tagged Molecular Inversion Probes", Nature Biotechnology, 21 (6), 2003, 673-678.
Hardenbol, Paul et al., "Highly multiplexed molecular inversion probe genotyping: Over 10,000 targeted SNPs genotyped in a singled tube assay", Genome Research, 15, 2005, 269-275.
Harismendy, O. et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.
Harper, J. C. et al., "Recent Advances and Future Developments in PGD", Prenatal Diagnosis, 19, 1999, 1193-1199.
Harton, G.L. et al., "Preimplantation Genetic Testing for Marfan Syndrome", Molecular Human Reproduction, 2 (9), 1996, 713-715.

Hayden, et al., "Multiplex-Ready PCR: A new method for multiplexed SSR and SNP genotyping", BMC Genomics 2008, 9(80), 1-12.
Hellani, A. et al., "Clincal Application of Multiple Displacement Amplification in Preimplantation Genetic Diagnosis", Reproductive BioMedicine Online, 10 (3), 2005, 376-380.
Hellani, Ali et al., "Multiple displacement amplification on single cell and possible PGD applications", Molecular Human Reproduction, 10(11), 2004, 847-852.
Hojsgaard, S. et al., "BIFROST—Block recursive models induced from relevant knowledge, observations, and statistical techniques,", Computational Statistics & Data Analysis, 19(2), 1995, 155-175.
Holleley, et al., "Multiplex Manager 1.0: a Cross-Platform Computer Program that Plans and Optimizes Multiplex PCR", BioTechniques46:511-517 (Jun. 2009), 511-517.
Hollox, E. et al., "Extensive Normal Copy Number Variation of a β-Defensin Antimicrobial-Gene Cluster", Am. J. Hum. Genet., 73, 2003, 591-600.
Homer, et al., "Resolving Individuals Contributing Trace Amounts of DNA to Highly Complex Mixtures Using High-Density SNP Genotyping Microarrays", PLOS Genetics, 4(8), 2008, 9 pgs.
Hoogendoorn, Bastiaan et al., "Genotyping Single Nucleotide Polymorphisms by Primer Extension and High Perforrnance Liquid Chromotography", Hum Genet, 104, 1999, 89-93.
Hsopital, F. et al., "A General Algorithm to Compute Multilocus Genotype Frequencies Under Various Mating Systems" vol. 12, No. 6, Jan. 1, 1996 (Jan. 1, 1996), pp. 455-462.
Howie, et al., "Fast and accurate genotype imputation in genome-wide association studies through pre-phasing", Nature Genetics, vol. 44, No. 8, Jul. 22, 2012, 955-959.
Hu, Dong Gui et al., "Aneuploidy Detection in Single Cells Using DNA Array-Based Comparative Genomic Hybridization", Molecular Human Reproduction, 10(4), 2004, 283-289.
Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.
Illumina Catalog, "Paired-End Sample Preparation Guid, Illumina Catalog# PE-930-1 001, Part# 1005063 Rev. E", 2011, 1-40.
Ishii, et al., "Optimization of Annealing Temperature to Reduce Bias Caused by a Primer Mismatch in Multitemplate PCR", Applied and Environmental Microbiology, Aug. 2001, p. 3753-3755.
Johnson, D.S. et al., "Comprehensive Analysis of Karyotypic Mosaicism Between Trophectoderm and Inner Cell Mass", Molecular Human Reproduction, 16(12), 2010, 944-949.
Johnson D.S. et al., "Preclinical Validation of a Microarray Method for Full Molecular Karyotyping of Blastomeres in a 24-h Protocol" Human Reproduction, 25 (4), 2010, 1066-1075.
Kaplinski, Lauris et al., "MultiPLX: Automatic Grouping and Evaluation of PCR Primers", Bioinformatics, 21(8), 2005, 1701-1702.
Kazakov, V.I. et al., "Extracellular DNA in the Blood of Pregnant Women", sitologia, 37, 3, 1995, 8.
Kijak, G. et al., "Discrepant Results in the Interpretation of HIV-1 Drug-Resistance Genotypic Data Among Widely Used Algorithms", HIV Medicine, 4, 2003, 72-78.
Kinnings, S. L. et al., "Factors affecting levels of circulating cell-free fetal DNA in maternal plasma and their implications for noninvasive prenatal testing", Prenatal Diagnosis, vol. 35, 2015, 816-822.
Konfortov, Bernard A. et al., "An Efficient Method for Multi-Locus Molecular Haplotyping", Nucleic Acids Research, 35(1), e6, 2007, 8 pgs.
Krjutskov, K. et al., "Development of a single tuve 640-plex genotyping method for detection of nucleic acid variations on microarrays", Nucleic Acids Research, vol. 36, No. 12, May 23, 2008 (May 23, 2008), pp. e75-e75.
Kuliev, Anver et al., "Thirteen Years' Experience on Preimplantation Diagnosis: Report of the Fifth International Symposium on Preimplantation Genetics", Reproductive Biomedicine Online, 8, 2, 2004, 229-235.
Lambert-Messerlian, G. et al., "Adustrnent of Serum Markers in First Trimester Screening", Journal of Medical Screening, 16 (2), 2009, 102-103.

(56) References Cited

OTHER PUBLICATIONS

Lathi, Ruth B. et al., "Informatics Enhanced SNP Microarray Analysis of 30 Miscarriage Samples Compared to Routine Cytogenetics", PLoS ONE, 7(3), 2012, 5 pgs.
Leary, Rebecca J. et al., "Detection of Chromosomal Alteraions in the Circulation of Cancer Patients with Whole-Genome Sequencing", Science Translational Medicine, 4, 162, 2012, 12.
Li, Yind et al., "Non-Invasive Prenatal Diagnosis Using Cell-Free Fetal DNA in Maternal Plasma from PGD Pregnancies", Reproductive BioMedicine Online, 19 (5), 2009, 714-720.
Li, Ying et al., "Size Separation of Circulatory DNA in Maternal Plasma Permits Ready Detection of Fetal DNA Polymorphisms", Clinical Chemistry, 50, 6, 2004, 1002-1011.
Li B, "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet:<URL: http://www.ashg.org/2012meeting/abstracts/fulltext/f120121811.htm>, 2012, 1 pg.
Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.
Liao, J. et al., "An Alternative Linker-Mediated Polymerase Chain Reaction Method Using a Dideoxynucleotide to Reduce Amplification Background", Analytical Biochemistry 253, 137-139 (1997).
Liew, Michael et al., "Genotyping of Single-Nucleotide Polymorphisms", Clinical Chemistry, 50(7), 2004, 1156-1164.
Lindroos, Katatina et al., "Genotyping SNPs by Minisequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.
Lo, et al., "Digital PCR for the Molecular Detection of Fetal Chromosomal Aneuploidy", PNAS, vol. 104, No. 32, Aug. 7, 2007, 13116-13121.
Lo, et al., "Fetal Nucleic Acids in Maternal Blood: the Promises", Clin. Chem. Lab. Med., 50(6), 2012, 995-998.
Lo, et al., "Free Fetal DNA in Maternal Circulation", JAMA, 292(23), (Letters to the Editor), 2004, 2835-2836.
Lo, "Non-Invasive Prenatal Diagnosis by Massively parallel Sequencing of Maternal Plasma DNA", Open Biol 2: 120086, 2012, 1-5.
Lo, et al., "Prenatal Sex Determination by DNA Amplification from Maternal Peripheral Blood", The Lancet 2, 8676, 1989, 1363-1365.
Lo, et al., "Rapid Clearance of Fetal DNA from Maternal Plasma", Am. J. Hum. Genet., 64, 1999, 218-224.
Lo, et al., "Strategies for the Detection of Autosomal Fetal DNA Sequence from Maternal Peripheral Blood", Annals New York Academy of Sciences, 731, 1994, 204-213.
Lo, et al., "Two-way cell traffic between mother and fetus: biologic and clinical implications", Blood, 88(11), Dec. 1, 1996, 4390-4395.
Lo, Dennis Y. et al., "Fetal Nucleic Acids in Maternal Plasma: Toward the Development of Noninvasive Prenatal Diagnosis of Fetal Chromosome Aneuploidies", Ann. N.Y. Acad. Sci., 1137, 2008, 140-143.
Lo, Dennis Y. et al., "Plasma placental RNA allelic ratio permits noninvasive prenatal chromosomal aneuploidy detection", Nature Medicine, 13(2), 2007, 218-223.
Lo, Dennis Y.M. et al., "Maternal Plasma DNA Sequencing Reveals the Genome-Wide Genetic and Mutational Profile of the Fetus", Science Translational Medicine, 2, 61, 2010, 13.
Lo, Dennis Y.M. et al., "Presence of Fetal DNA in Maternal Plasma and Serum", The Lancet, 350, 1997, 485-487.
Lo, Dennis Y.M. et al., "Quantitative Analysis of Fetal DNA in Maternal Plasma and Serum: Implications for Noninvasive Prenatal Diagnosis", Am. J. Hum. Genet., 62, 1998, 768-775.

Lo, Y.M.D. et al., "Prenatal Determination of Fetal Rhesus D Status by DNA Amplification of Peripheral Blood of Rhesus-Negative Mothers", Annals New York Academy of Science, 731, 1994, 229-236.
Lo, Y-M.D. et al., "Prenatal Determination of Fetal RhD Status by Analysis of Peripheral Blood of Rhesus Negative Mothers", The Lancet, 341, 1993, 1147-1148.
Lo, Y-M.D. et al., "Detection of Single-Copy Fetal DNA Sequence from Maternal Blood", The Lancet, 335, 1990, 1463-1464.
Lo, Y. et al., "Detection of Fetal RHD Sequence from Peripheral Blood of Sensitized RhD-Negative Pregnant Women", British Journal of Haematology, 87, 1994, 658-660.
Luo, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.
Maniatis, T. et al., "In: Molecular Cloning: A Laboratory Manual", Cold Spring Harbor Laboratory, New York, Thirteenth Printing, 1986, 458-459.
Mansfield, Elaine S., "Diagnosis of Down Syndrome and Other Aneuploidies Using Quantitative Polymerase Chain Reaction and Small Tandem Repeat Polymorphisms", Human Molecular Genetics, 2, 1, 1993, 43-50.
Markoulatos, P. et al., "Multiplex Polymerase Chain Reactuion: A Practical Approach", 2002 Wiley-Liss, Inc. DOI 10.1002/jcla.2058 Journal of Clinical Laboratory Analysis 16:47-51 (2002).
May, Rober M. et al., "How Many Species Are There on Earth?", Science, 241, 1988, 1441-1449.
McCray, Alexa T. et al., "Aggregating UMLS Semantic Types for Reducing Conceptual Complexity", MEDINFOR 2001: Proceedings of the 10th World Congress on Medical Informatics (Studies in Health Technology and Informatics, 84, V. Patel et al. (eds.), IOS Press Amsterdam, 2001, 216-220.
Mennuti, M. et al., "Is It Time to Sound an Alarm About False-Positive Cell-Free DNA Testing for Fetal Aneuploidy?", American Journal of Obstetrics, 2013, 5 pgs.
Mersy, et al., "Noninvasive Detection of Fetal Trisomy 21: Systematic Review and Report of Quality and Outcomes of Diagnostic Accuracy Studies Perofrmed Between 1997 and 2012", Human Reproduction Update, 19(4), 2013, 318-329.
Miller, Robert, "Hyperglycemia-Induced Changes in Hepatic Membrane Fatty Acid Composition Correlate with Increased Caspase-3 Activites and Reduced Chick-Embryo Viability", Comparative Biochemistry and Physiology, Part B, 141, 2005, 323-330.
Miller, Robert R., "Homocysteine-Induced Changes in Brain Composition Correlate with Increased Brain Caspase-3 Activites and Reduced Chick-Embryo Viability", Comparative Biochemistry and Physiology Part B, 136, 2003, 521-532.
Morand, et al., "Hesperidin contributes to the vascular protective effects of orange juice: a randomized crossover study in healthy volunteers", Am J Clin Nutr. Jan. 2011;93(1):73-80. Epub Nov. 10, 2010.
Munne, S. et al., "Chromosome abnormalities in human embryos", Human Reproduction update, 4 (6), 842-855.
Murtaza, M. et al., "Non-Invasive Analysis of Acquired Resistance to Cancer Therapy by Sequencing of Plasma DNA", Nature (doi:10.1038/nature12065), 2013, 6 pgs.
Muse, Spencer V., "Examining rates and patterns of nucleotide substitution in plants", Plant Molecular Biology 42:25-43, 2000.
Myers, Chad L. et al., "Accurate Detection of Aneuploidies in Array CGH and Gene Expression Microarray Data", Bioinformatics, 20(18), 2004, 3533-3543.
Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.
Nicolaides, K. et al., "Noninvasive Prenatal Testing for Fetal Tirsomies in a Routinely Screened First-Trimester Population", American Journal of Obstetrics (article in press), 207, 2012, 1.e1-1.e6.
Nicolaides, K.H. et al., "Validation of Targeted Sequencing of Single-Nucleotide Polymorphisms for Non-Invasive Prenatal

(56) References Cited

OTHER PUBLICATIONS

Detection of Aneuploidy of Chromosomes 13, 18, 21, X, and Y", Prenatal Diagnosis, 33, 2013, 575-579.
Nicolaides, Kypros H. et al., "Prenatal Detection of Fetal Triploidy from Cell-Free DNA Testing in Maternal Blood", Fetal Diagnosis and Therapy, 2013, 1-6.
Nygren, et al., "Quantification of Fetal DNA by Use of Methylation-Based DNA Discrimination", Clinical Chemistry 56:10 1627-1635 (2010).
Ogino, S. et al., "Bayesian Analysis and Risk Assessment in Genetic Counseling and Testing", Journal of Molecular Diagnostics, 6 (1), 2004, 9 pgs.
O'Malley, R. et al., "An adapter ligation-mediated PCR method for high-throughput mapping of T-DNA inserts in the Arabidopsis genome", Nat. Protoc. 2, 2910-2917 (2007).
Orozco A.F., et al., "Placental Release of Distinct DNA-Associated Micro-Particles into Maternal Circulation: Reflective of Gestation Time and Preeclampsia", Placenta,30, 2009, 891-897.
Ozawa, Makiko et al., "Two Families with Fukuyama Congenital Muscular Dystrophy that Underwent In Utero Diagnosis Based on Polymorphism Analysis", Clinical Muscular Dystrophy: Research in Immunology and Genetic Counseling—FY 1994 Research Report, (including text in Japanese), 1994, 8.
Paez, Guillermo J. et al., "Genome coverage and sequence fidelity of $\phi$29 polymerase-based multiple strand displacement whole genome amplification", Nucleic Acids Research, 32(9), 2004, 1-11.
Page, S. L. et al., "Chromosome Choreography: The Melotic Ballet", Science, 301, 2003, 785-789.
Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012. 10.
Palomaki, Glenn E. et al., "DNA Sequencing of Maternal Plasma to Detect Down Syndrome: An International Clinical Validation Study", Genetics in Medicine (pre-print version) 13, 2011, 8 pgs.
Papageorgiou, Elisavet A. et al., "Fetal-Specific DNA Methylation Ratio Permits Noninvasive Prenatal Diagnosis of Trisomy 21", Nature Medicine (advance online publication), 17, 2011, 5 pgs.
PCT/US2006/045281, "International Preliminary Report on Patentability", mailed May 27, 2008, 1 pg.
PCT/US2006/045281, "International Search Report and Written Opinion", mailed Sep. 28, 2007, 7 pgs.
PCT/US2008/003547, "International Search Report", mailed Apr. 15, 2009, 5 pgs.
PCT/US2009/034506, "International Search Report", mailed Jul. 8, 2009, 2 pgs.
PCT/US2009/045335, "International Search Report", mailed Jul. 27, 2009, 1 pg.
PCT/US2009/052730. "International Search Report", mailed Sep. 28, 2009, 1 pg.
PCT/US2010/050824, "International Search Report", mailed Nov. 15, 2010, 2 pgs.
PCT/US2011/037018, "International Search Report", mailed Sep. 27, 2011, 2 pgs.
PCT/US2011/061506, "International Search Report", mailed Mar. 16, 2012, 1 pgs.
PCT/US2011/066938, "International Search Report", mailed Jun. 20, 2012, 1 pg.
PCT/US2012066339, "International Search Report", mailed Mar. 5, 2013, 1 pg.
PCT/US2013/028378, "International Search Report and Written Opinion", mailed May 28, 2013, 11 pgs.
PCT/US2013/57924, "International Search Report and Written Opinion", mailed Feb. 18, 2014, 8 pgs.
PCT/US2014/051926, "International Search Report mailed", Dec. 9, 2014, 3 pgs.
PCT/US2014/51926, "Written Opinion", mailed Dec. 9, 2014, 5 pgs.
PCT/US2015/026957, "International Preliminary Report on Patentability mailed on Nov. 3, 2016", Nov. 3, 2016, 3 pages.

Pearson, K., "On the criterion that a given system of deviations from the probable in the case of a correlated system of variables is such that it can be reasonably supposed to have arisen from random sampling", Philosophical Magazine Series 5, vol. 50, Issue 302, 1900, 157-175.
Pena, Sergio D.J. et al., "Paternity Testing in the DNA Era", Trends in Genetics, 10, 6, 1994, 204-209.
Perkel, Jeffrey M., "Overcoming the Challenges of Multiplex PCR", Biocompare Editorial Article, NULL, 2012, 1-5.
Perry, George H. et al., "The Fine-Scale and Complex Architecture of Human Copy-Number Variation", The American Journal of Human Genetics,82, 2008, 685-695.
Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.
Peters, David P. et al., "Noninvasive Prenatal Diagnosis of a Fetal Microdeletion Syndrome", New England Journal of Medicine, 365(19), 2011, 1847-1848.
Pfaffl, Michael W., "Relative Expression Software Tool (REST ©) for Group-Wise Comparison and Statistical Analysis of Relative Expression Results in real-Time PCR", Nucleic Acids Research, 30(9), 2002, 10 pgs.
Phillips, C. et al., "Resolving Relationship Tests that Show Ambiguous STR Results Using Autosomai SNPs as Supplementary Markers", Forensic Science International: Genetics 2, 2008, 198-204.
Podder, Mohua et al., "Robust SN P genotyping by multiplex PCR and arrayed primer", BMC Medical Genomics,1(5), 2008, 1-15.
Porreca, Gregory J. et al., "Multiplex Amplification of Large Sets of Human Exons", Nature Methods, 4, (advance online publication), 2007, 6.
Price, T.S. et al., "SW-Array: a dynamic programming solution for the identification of copy-number changes in genomic DNA using array comparative genome hybridization data", Nucleic Acids Research, vol. 33, No. 11, Jun. 16, 2005 (Jun. 16, 2005), pp. 3455-3464.
Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006. 541-549.
Rabinowitz, Matthew et al., "Origins and rates of aneuploidy inhuman blastomeres", Fertility and Sterility, Elsevier Science Inc, 97(2), 2012, 395-401.
Rabinowitz, Matthew et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.
Rachlin, J. et al., "Computational tradeoffs in multiplex PCR assay design for SNP genotyping", BMC Genomics, vol. 6, No. 102, Jul. 25, 2005, 11 pages.
Rahmann, Sven et al., "Mean and variance of the Gibbs free energy of oligonucleotides in the nearest neighbor model under varying conditions", Bioinformatics, 20(17), 2004, 2928-2933.
Rava, Richard P. et al., "Circulating Fetal Cell-Free DNA Fraction Differ in Autosomal Aneuploidies and Monosomy X", Clinical Chemistry, 60(1), (papers in press), 2013, 8 pgs.
Rechitsky, Svetlana et al., "Preimplantation Genetic Diagnosis with HLA Matching", Reproductive Bio Medicine Online, 9, 2, 2004, 210-221.
Renwick, Pamela et al., "Proof of Principle and First Cases Using Preimplantation Genetic Haplotyping—A Paradigm Shift for Embryo Diagnosis", Reproductive BioMedicine Online, 13 (1), 2006, 110-119.
Ricciotti, Hope, "Eating by Trimester", Online]. Retrieved from Internet:<http://www.youandyourfamily.com/article.php?story=Eating+by+Trimester>, 2014, 3.
Roper, Stephen M. et al., "Forensic Aspects of DNA-Based Human Identity Testing", Journal of Forensic Nursing, 4, 2008, 150-156.
Roux, K., "Optimization and Troubleshooting in PCR", PCR Methods Appl. 4, 1995, 185-194.
Rozen, Steve et al., "Primer3 on the WWW for General Users and for Biologis Programmers", Methods in Molecular Biology, 132: Bioinformatics Methods and Protocols, 1999, 365-386.

(56) References Cited

OTHER PUBLICATIONS

Russell, L.M., "X Chromosome Loss and Ageing", Cytogenetic and Genome Res., 116, 2007, 181-185.

Ryan, et al., "The importance of phase information for human genomics", Nature Reviews Genetics, vol. 12, No. 3, Mar. 1, 2011.

Ryan, Allison et al., "Informatics-Based, Highly Accurate, Noninvasive Prenatal Paternity Testing", Genetics in Medicine (advance online publication), 2012, 5 pgs.

Rychlik, et al., "Optimization of the annealing temperature for DNA amplification in vitro", Nucleic Acids Research, 18(21), 1990, 6409-6412.

Samango-Sprouse, C. et al., "SNP-Based Non-Invasive Prenatal Testing Detects Sex Chromosome Aneuploidies with High Accuracy", Prenatal Diagnosis, 33, 2013, 1-7.

Sander, Chris, "Genetic Medicine and the Future of Health Care", Science, 287(5460), 2000, 1977-1978.

Santalucia, J. et al., "The Thermodynamics of DNA Structural Motifs", Annu. Rev. Biophys. Biomol. Struct., 33, 2004, 415-440.

Santalucia, John J.R. et al., "Improved Nearest-Neighbor Parameters for Predicting DNA Duplex Stability", Biochemistry, 35, 1996, 3555-3562.

Sasabe, Yutaka, "Genetic Diagnosis of Gametes and Embryos Resulting from ART", Japanese Journal of Fertility and Sterility, 2001, vol. 46, No. 1, p. 43-46.

Schoumans, J et al., "Detection of chromosomal imbalances in children with idiopathic mental retardation by array based comparative genomic hybridisation (array-CGH)", JMed Genet, 42, 205, 699-705.

Sebat, Jonathan et al., "Strong Association of De Novo Copy Number Mutations with Autism", Science, 316, 2007, 445-449.

Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.

Sermon, Karen et al., "Preimplantation genetic diagnosis", The Lancet, Lancet Limited. 363(9421), 2000, 1633-1641.

Servin, B et al., "MOM: A Program to Compute Fully Informative Genotype Frequencies in Complex Breeding Schemes", Journal of Heredity, vol. 93, No. 3, Jan. 1, 2002 (Jan. 1, 2002), pp. 227-228.

Shaw-Smith, et al., "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., 41, 2004, 241-248.

Shen, et al., "High-quality DNA sequence capture of 524 diease candidate genes", High-quality DNA sequence capture of 524 disease candidate genes, Proceedings of the National Academy of Sciences, vol. 108, No. 15, Apr. 5, 2011, (Apr. 5, 2011), pp. 6549-6554.

Shen, Zhiyong, "MPprimer: a program for reliable multiplex PCR primer design", BMC Bioinformatics 2010, 11:143, 1-7.

Sherlock, J. et al., "Assesment of Diagnostic Quantitative Fluorescent Multiplex Polymerase Chain Reaction Assays Performed on Single Cells", Annals of Human Genetics,62, 1, 1998, 9-23.

Simpson, J. et al., "Fetal Cells in Maternal Blood: Overview and Historical Perspective", Annals New York Academy of Sciences, 731, 1994, 1-8.

Sint, Daniela et al., "Advances in Multiplex PCR: Balancing Primer Efficiencies and Improving Detection Success", Methods in Ecology and Evolution, 3, 2012, 898-905.

Slater, Howard et al., "High-Resolution Identification of Chromosomal Abnormalities Using Oligonucleotide Arrays Containing 116,204 SNPs", Am. J. Hum. Genet., 77, 5, 2005, 709-726.

Snijders, Antoine et al., "Assembly of Microarrays for Genome-Wide Measurement of DNA Copy Number", Nature Genetic, 29, 2001, 263-264.

Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1-319.e9.

Sparks, Andrew B. et al., "Selective Analysis of Cell-Free DNA in Maternal Blood for Evaluation of Fetal Trisomy", Prenatal Diagnosis, 32, 2012, 1-7.

Spiro, Alexander et al., "A Bead-Based Method for Multiplexed Identification and Quantitation of DNASequences Using Flow Cytometry", Applied and Environmental Microbiology, 66, 10, 2000, 4258-4265.

Spits, C. et al., "Optimization and Evaluation of Single-Cell Whole Genome Multiple Displacement Amplification", Human Mutation, 27(5), 496-503, 2006.

Srinivasan, et al., "Noninvasive Detection of Fetal Subchromosome Abnormalities via Deep Sequencing of Maternal Plasma", The American Journal of Human Genetics 92, 167-176, Feb. 7, 2013.

Stephens, Mathews. et al. "A Comparison of Bayesian Methods for Haplotype Reconstruction from Population Genotype Data", Am. J. Hum. Genet.,73, 2003, 1162-1169.

Stevens, Robert et al., "Ontology-Based Knowledge Representation for Bioinformatics", Briefings in Bioinformatics, 1, 4, 2000, 398-414.

Steyerberg, E.W. et al., "Application of Shrinkage Techniques in Logistic Regression Analysis: A Case Study", Statistica Neerlandica, 55(1), 2001, 76-88.

Strom, C. et al., "Three births after preimplantation genetic diagnosis for cystic fibrosis with sequential first and second polar body analysis", American Journal of Obstetrics and Gynecology, 178 (6), 1998, 1298-1306.

Strom, Charles M. et al., "Neonatal Outcome of Preimplantation Genetic Diagnosis by Polar Body Removal: The First 109 Infants", Pediatrics, 106( 4), 2000, 650-653.

Stroun, Maurice et al., "Prehistory of the Notion of Circulating Nucleic Acids in Plasma/Serum (CNAPS): Birth of a Hypothesis", Ann. N.Y. Acad. Sci., 1075, 2008, 10-20.

Su, S.Y. et al., "'Inferring combined CNV/SNP haplotypes from genotype data'", Bioinformatics, vol. 26, No. 11,1, Jun. 1, 2010, 1437-1445.

Sun, Guihua et al., "SNPs in human miRNA genes affect biogenesis and function", RNA, 15(9), 2009, 1640-1651.

Sweet-Kind Singer, J. A. et al., "Log-penalized linear regression", IEEE International Symposium on Information Theory, 2003. Proceedings, 2003, 286.

Tamura, et al., "Sibling Incest and formulation of paternity probability: case report", Legal Medicine, 2000, vol. 2, p. 189-196.

Tang, et al., Multiplex fluorescent PCR for noninvasive prenatal detection of fetal-derived paternally inherited diseases using circulatory fetal DNA in maternal plasma, Eur J Obstet Gynecol Reprod Biol, 2009, v. 144, No. 1, p. 35-39.

Tang, N. et al., "Detection of Fetal-Derived Paternally Inherited X-Chromosome Polymorphisms in Maternal Plasma", Clinical Chemistry, 45 (11), 1999, 2033-2035.

Thomas, M.R. et al., "The Time of Appearance and Disappearance of Fetal DNA from the Maternal Circulation", Prenatal Diagnosis, 15, 1995, 641-646.

Tong, Yu et al., "Nonnvasive Prenatal Detection of Fetal Trisomy 18 by epigenetic Allelic Ratio Analysis in Maternal Plasma: Theoretical and Empirical Considerations", Clinical Chemistry, 52(12), 2006, 2194-2202.

Tong, Yu K. et al., "Noninvasive Prenatal Detection of Trisomy 21 by Epigenetic-Genetic Chromosome-Dosage Approach", Clinical Chemistry, 56(1), 2010, 90-98.

Troyanskaya, Olga G. et al., "A Bayesian Framework for Combining Heterogenous Data Sources for Gene Function Prediction (in *Saccharomyces cerevisiae*)", PNAS, 100(14), 2003, 8348-8353.

Tsui, Nancy B.Y. et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.

Turner, E. et al., "Massively Parallel Exon Capture and Library-Free Resequencing Across 16 Genomes", Nature Methods, 6 (5), 2009, 315-316.

Vallone, Peter, "AutoDimer: a Screening Tool for Primer-Dimer and Hairpin Structures", Bio Techniques, 37, 2004, 226-231.

(56) References Cited

OTHER PUBLICATIONS

Varley, Katherine Elena et al., "Nested Patch PCR Enables Highly Multiplexed Mutation Discovery in Candidate Genes", Genome Res., 18(11), 2008, 1844-1850.
Verlinky, Y. et al., "Over a Decade of Experience with Preimplantation Genetic Diagnosis", Fertility and Sterility, 82 (2), 2004, 302-303.
Wagner, Jasenka et al., "Non-Invasive Prenatal Paternity Testing from Maternal Blood", Int. J. Legal Med., 123, 2009, 75-79.
Wang, Eric et al., "Gestational Age and Maternal Weight Effects on Fetal Cell-Free DNA in Maternal Plasma", Prenatal Diagnosis, 33, 2013, 662-666.
Wang, Hui-Yun et al., "A genotyping system capable of simultaneously analyzing >1000 single nucleotide polymorphisms in a haploid genome", Genome Res., 15, 2005, 276-283.
Wang, Yuker et al., "Allele quantification using molecular inversion probes (MIP)", Nucleic Acids Research, vol. 33, No. 21, Nov. 28, 2005, 14 pgs.
Wapner, R. et al., "Chromosomal Microarray Versus Karyotyping for Prenatal Diagnosis", The New England Journal of Medicine, 367 (23), 2012, 2175-2184.
Watkins, N. et al., "Thermodynamic contributions of single internal rA •dA, rC • dC, rG • dG and rU • dT mismatches in RNA/DNA duplexes", Nucleic Acids Research, 9 (5),, 2010, 1894-1902.
Wells, D., "Microarray for Analysis and Diagnosis of Human Embryos", 12th International Congress on Prenatal Diagnosis and Therapy, Budapest, Hungary, 2004, 9-17.
Wells, Dagan, "Advances in Preimplantation Genetic Diagnosis", European Journal of Obstetrics and Gynecology and Reproductive Biology, 115S, 2004, S97-S101.
Wells, Dagan, "Detailed Chromosomal and Molecular Genetic Analysis of Single Cells by Whole Genome Amplification and Comparative Genomic Hybridisation", Nucleic Acids Research, 27, 4, 1999, 1214-1218.
Wen, Daxing et al., "Universal Multiples PCR: A Novel Method of Simultaneous Amplification of Multiple DNA Fragments", Plant Methods, 8(32), NULL, 2012, 1-9.
Wilton, et al., "Birth of a Healthy Infant After Preimplantation Confirmation of Euploidy by Comparative Genomic Hybridization", N. Engl. J. Med., 345(21), 2001, 1537-1541.
Wilton, L., "Preimplantation Genetic Diagnosis and Chromosme Analysis of Blastomeres Using Comparative Genomic Hybridization", Human Reproduction Update, 11 (1), 2005, 33-41.
Wright, C. F. et al., "Cell-free fetal DNA and RNA in maternal blood: implications for safer antenatal testing", BMJ, vol. 39, Jul. 18, 2009, 161-165.
Wu, Y. Y. et al., "Rapid and/or high-throughput genotyping for human red blood cell, platelet and leukocyte antigens, and forensic applications", Clinica Chimica Acta, vol. 363, 2006, 165-176.
Xia, Tianbing et al., "Thermodynamic Parameters for an Expanded Nearest-Neighbor Model for Formation of RNA Duplexes with Watson-Crick Base Pairs", Biochemistry, 37, 1998, 14719-14735.
Yeh, Iwei et al., "Knowledge Acquisition, Consistency Checking and Concurrency Control for Gene Ontology (GO)", Bioinformatics, 19, 2, 2003, 241-248.
You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.
Zhang, Rui et al., "Quantifying RNA allelic ratios by microfluidic multiplex PCR and sequencing", Nature Methods, (11)1, 2014, 51-56.
Zhao, Xiaojun et al., "An Integrated View of Copy Number and Allelic Alterations in the Cancer Genome Using Single Nucleotide Polymorphism Arrays", Cancer Research,64, 2004, 3060-3071.
Zhou, W. et al., "Counting Alleles Reveals a Connection Between Chromosome 18q Loss and Vascular Invasion", Nature Biotechnology, 19, 2001, 78-81.
Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.
Fan, H. Christina et al., "Sensitivity of Noninvasive Prenatal Detection of Fetal Aneuploidy from Maternal Plasma Using Shotgun Sequencing Is Limited Only by Counting Statistics", PLoS ONE, vol. 5, Issue 5 (e10439), May 3, 2010, 1-6.
Ragoussis, J., "Genotyping Technologies for Genetic Research", Annual Review of Genomics and Human Genetics, vol. 10(1), Sep. 1, 2009, 117-133.
Taliun, D. et al., "Efficient haplotype block recognition of very long and dense genetic sequences", BMC Bioinformatics, vol. 15(10), 2014, 1-18.
U.S. Appl. No. 15/187,555, filed Jun. 20, 2016, System and Method for Cleaning Noisy Genetic Data From Target Individuals Using Genetic Data From Genetically Related Individuals.
U.S. Appl. No. 15/191,197, filed Jun. 23, 2016, System and Method for Cleaning Noisy Genetic Data From Target Individuals Using Genetic Data From Genetically Related Individuals.
U.S. Appl. No. 15/293,257, filed Oct. 13, 2016, System and Methof for Cleaning Noisy Genetic Data from Target Individuals Using Genetic Data from Genetically Related Individuals.
U.S. Appl. No. 14/866,223, filed Sep. 25, 2015, Methods for Non-Invasive Prenatal Ploidy Calling.
U.S. Appl. No. 14/877,925, filed Oct. 7, 2015, Highly Multiplex Pcr Methods and Compositions.
U.S. Appl. No. 14/983,128, filed Dec. 29, 2015, Methods for Non-Invasive Prenatal Ploidy Calling.
U.S. Appl. No. 15/252,795, filed Aug. 31, 2016, Methods for Non-Invasive Prenatal Ploidy Calling.
U.S. Appl. No. 15/273,332, filed Sep. 22, 2016, Methods for Non-Invasive Prenatal Ploidy Calling.
U.S. Appl. No. 15/343,003, filed Nov. 3, 2016, Methods for Non-Invasive Prenatal Ploidy Calling.
U.S. Appl. No. 14/732,632, filed Nov. 12, 2014, Systems and Methods for Detection of Aneuploidy.
U.S. Appl. No. 14/538,998, filed Nov. 24, 2014, Methods for Simultaneous Amplification of Target Loci.
U.S. Appl. No. 14/692,703, filed Apr. 21, 2015, Detecting Mutations and Ploidy in Chromosomal Segments.
U.S. Appl. No. 14/882,763, filed Oct. 14, 2015, Detecting Cancer Mutations and Aneuploidy in Chromosomal Segments.
U.S. Appl. No. 14/918,544, filed Oct. 20, 2015, Methods for Simultaneous Amplification of Target Loci.
U.S. Appl. No. 15/336,630, filed Oct. 27, 2016, Methods for Simultaneous Amplification of Target Loci.
U.S. Appl. No. 15/186,774, filed Jun. 20, 2016, Systems and Methods for Determining Aneuploidy Risk Using Sample Fetal Fraction.
U.S. Appl. No. 15/372,279, filed Dec. 7, 2016, Compositions and Methods for Identifying Nucleic Acid Molecules.
U.S. Appl. No. 15/293,257, filed Oct. 13, 2016, System and Method for Cleaning Noisy Genetic Data From Target Individuals Using Genetic Data From Genetically Related Individuals.
U.S. Appl. No. 15/413,200, filed Jan. 23, 2017, System and Method for Cleaning Noisy Genetic Data and Determining Chromosome Copy Number.
U.S. Appl. No. 15/446,778, filed Mar. 1, 2017, System and Method for Cleaning Noisy Genetic Data and Determining Chromosome Copy Number.
U.S. Appl. No. 15/586,013, filed May 3, 2017, Methods for Non-Invasive Prenatal Ploidy Calling.
U.S. Appl. No. 15/433,950, filed Feb. 15, 2017, Methods for Non-Invasive Prenatal Testing Using Parental Mosaicism Data.

| | Features of Different Techniniques of Screening for Aneuploidy | | | | | | | | | | | | | | | |
|---|---|---|---|---|---|---|---|---|---|---|---|---|---|---|---|---|
| Technique Description | Formula Applied to compute N = | Assay Name | E(m1) | E(m0) | Std(m1) | Std(m0) | Copy No. Compare | Mosaicism | N | Price per SNP | Additional Costs | Factor Sigma | 1- Conf | Segments | Cells per Well | Total Cells w/o PCR | Cost |
| Comp of means no reference sample | 2^2*5^2*s^2/(m1-m0)^2 | Taqman | 32.26 | 30.75 | 0.597 | 0.597 | 2 vs 1 | 100.0% | 16 | $0.20 | 30 | 5 | 2.87E-07 | 5 | 50 | 800 | $48.00 |
| Comp of means with ref. sample | 2^2*5^2*(2*s^2)/(m1-m0)^2 | Taqman | 32.26 | 30.75 | 0.597 | 0.597 | 2 vs 1 | 100.0% | 32 | $0.20 | 30 | 5 | 2.87E-07 | 5 | 50 | 1600 | $62.00 |
| Comp of means no reference sample | 4*(2^2)*(0.95*s^2+0.05*s^2)/(0.05^2*(m1-m0)^2) | Taqman | 32.26 | 30.75 | 0.597 | 0.597 | 2 vs 1 | 5.0% | 1001 | $0.20 | 30 | 2 | 2.30E-02 | 5 | 50 | 50050 | $1,031.00 |
| Comp of means with ref. samples | 4*(2^2)*(1.95*s^2+0.05*s^2)/(0.05^2*(m1-m0)^2) | Taqman | 32.26 | 30.75 | 0.597 | 0.597 | 2 vs 1 | 5.0% | 2002 | $0.20 | 30 | 2 | 2.30E-02 | 5 | 50 | 100100 | $2,032.00 |
| Comp of means no reference sample | 4*(2^2)*(0.95*s^2+0.05*s^2)/(0.05^2*(m1-m0)^2) | MIPs | 32.26 | 30.75 | 0.597 | 0.597 | 2 vs 1 | 5.0% | 1001 | $0.01 | 200 | 2 | 2.30E-02 | 5 | 50 | 50050 | $250.05 |
| Comp of means with ref. sample | 4*(2^2)*(1.95*s^2+0.05*s^2)/(0.05^2*(m1-m0)^2) | MIPs | 32.26 | 30.75 | 0.597 | 0.597 | 2 vs 1 | 5.0% | 2002 | $0.01 | 200 | 2 | 2.30E-02 | 5 | 50 | 100100 | $300.10 |
| Comp of means no reference sample | 4*(2^2)*((1-ff)*s^2+ff*s^2)/(ff^2*(m1-m0)^2); ff = 0.081 | Taqman | 32.26 | 30.75 | 0.597 | 0.597 | 2 vs 1 | 8.1% | 384 | $0.20 | 30 | 2 | 2.30E-02 | 5 | 50 | 19200 | $414.00 |
| Comp of means no reference sample | 4*(1^2)*((1-ff)*s^2+ff*s^2)/(ff^2*(m1-m0)^2); ff = 0.058 | Taqman | 32.26 | 30.75 | 0.597 | 0.597 | 2 vs 1 | 4.1% | 384 | $0.20 | 30 | 1 | 1.59E-01 | 5 | 50 | 19200 | $414.00 |
| Comp of means no reference sample | 4*(2^2)*((1-ff)*s^2+ff*s^2)/(ff^2*(m1-m0)^2); ff = 0.19 | Taqman | 32.26 | 30.75 | 0.597 | 0.597 | 2 vs 1 | 19.0% | 70 | $0.20 | 30 | 2 | 2.30E-02 | 5 | 50 | 3500 | $100.00 |
| Comp of means no reference sample | 2^2*5^2*s^2/(m1-m0)^2 | qPCR | 27.65 | 26.64 | 0.53 | 0.53 | 2 vs 1 | 100.0% | 27 | $0.15 | 30 | 5 | 2.87E-07 | 5 | 50 | 1350 | $50.25 |
| Comp of means with ref. sample | 2^2*5^2*(2*s^2)/(m1-m0)^2 | qPCR | 27.65 | 26.64 | 0.53 | 0.53 | 2 vs 1 | 100.0% | 55 | $0.15 | 30 | 5 | 2.87E-07 | 5 | 50 | 2750 | $71.25 |
| Comp of means no reference sample | 4*(2^2)*(0.95*s^2+0.05*s^2)/(0.05^2*(m1-m0)^2) | qPCR | 27.65 | 26.64 | 0.53 | 0.53 | 2 vs 1 | 5.0% | 1754 | $0.15 | 30 | 2 | 2.30E-02 | 5 | 50 | 87700 | $1,345.50 |
| Comp of means with ref. samples | 4*(2^2)*(1.95*s^2+0.05*s^2)/(0.05^2*(m1-m0)^2) | qPCR | 27.65 | 26.64 | 0.53 | 0.53 | 2 vs 1 | 5.0% | 3508 | $0.15 | 30 | 2 | 2.30E-02 | 5 | 50 | 175400 | $2,681.00 |
| Comp of means no reference sample | 4*(2^2)*((1-ff)*s^2+ff*s^2)/(ff^2*(m1-m0)^2); ff = 0.107 | qPCR | 27.65 | 26.64 | 0.53 | 0.53 | 2 vs 1 | 10.7% | 384 | $0.15 | 30 | 2 | 2.30E-02 | 5 | 50 | 19200 | $318.00 |
| Comp of means no reference sample | 4*(1^2)*((1-ff)*s^2+ff*s^2)/(ff^2*(m1-m0)^2); ff = 0.054 | qPCR | 27.65 | 26.64 | 0.53 | 0.53 | 2 vs 1 | 5.4% | 384 | $0.15 | 30 | 1 | 1.59E-01 | 5 | 50 | 19200 | $318.00 |
| Comp of means no reference sample | 4*(2^2)*((1-ff)*s^2+ff*s^2)/(ff^2*(m1-m0)^2); ff = 0.19 | qPCR | 27.65 | 26.64 | 0.53 | 0.53 | 2 vs 1 | 19.0% | 121 | $0.15 | 30 | 2 | 2.30E-02 | 5 | 50 | 6050 | $120.75 |

FIG. 20

| snp_id | e1 | e2 | p1 | p2 | m1 | m2 | pe1 | pe2 | pp1 | pp2 | pm1 | pm2 |
|---|---|---|---|---|---|---|---|---|---|---|---|---|
| 101100940 | C | T | T | C | C | T | 0.9538 | 0.8902 | 0.8626 | 0.8580 | 0.8654 | 0.9101 |
| 101164838 | T | C | T | C | T | C | 0.9359 | 0.9521 | 0.9406 | 0.9253 | 0.9957 | 0.8770 |
| rs1463589 | C | C | T | C | C | C | 0.9428 | 0.9928 | 0.9841 | 0.9266 | 0.8661 | 0.9798 |
| 101028396 | C | G | C | G | C | C | 0.9252 | 0.8792 | 0.9246 | 0.9856 | 0.9819 | 0.8631 |
| 101204217 | A | G | G | A | G | G | 0.9799 | 0.9843 | 0.9194 | 0.9478 | 0.9438 | 0.9709 |
| 101214313 | A | G | G | A | G | A | 0.8513 | 0.9863 | 0.9521 | 0.9707 | 0.8570 | 0.9639 |
| 101231593 | G | A | G | G | A | A | 0.9857 | 0.9653 | 0.8908 | 0.9036 | 0.9431 | 0.9832 |
| rs1426442 | G | C | C | G | C | G | 0.9338 | 0.9278 | 0.9469 | 0.9514 | 0.8766 | 0.9017 |
| rs7486852 | C | C | C | T | T | C | 0.9566 | 0.9616 | 0.9390 | 0.8673 | 0.8785 | 0.8889 |
| 101266729 | A | G | A | G | A | G | 0.9238 | 0.9500 | 0.9026 | 0.9855 | 0.8760 | 0.9381 |

FIG. 21

| snp_id | e1 | e2 | p1 | p2 | m1 | m2 | pe1 | pe2 | pp1 | pp2 | pm1 | pm2 |
|---|---|---|---|---|---|---|---|---|---|---|---|---|
| 101019515 | G | G | G | G | G | G | 0.9134 | 0.8768 | 0.8666 | 0.9690 | 0.8679 | 0.8599 |
| 101100940 | C | T | T | C | C | T | 0.9538 | 0.8902 | 0.8626 | 0.8580 | 0.8654 | 0.9101 |
| 101160854 | A | A | A | A | A | A | 0.8705 | 0.9769 | 0.8763 | 0.8870 | 0.9311 | 0.9553 |
| rs4980809 | A | G | G | A | A | G | 0.9638 | 0.9951 | 0.9582 | 0.9621 | 0.9197 | 0.9199 |
| 101058479 | G | A | G | A | G | A | 0.9003 | 0.9885 | 0.8906 | 0.9235 | 0.9787 | 0.8792 |
| 101236938 | G | G | G | G | G | A | 0.8528 | 0.9710 | 0.8810 | 0.9249 | 0.9274 | 0.9891 |
| rs7137405 | T | T | T | T | T | A | 0.9360 | 0.9918 | 0.9148 | 0.9558 | 0.9135 | 0.9388 |
| 101251161 | G | G | G | G | G | G | 0.9802 | 0.8620 | 0.9372 | 0.8501 | 0.9891 | 0.8679 |
| 101270051 | G | G | G | G | G | A | 0.9004 | 0.9643 | 0.9778 | 0.9060 | 0.9943 | 0.8962 |
| rs215227 | G | G | G | G | G | A | 0.9244 | 0.9236 | 0.9629 | 0.8575 | 0.9019 | 0.9362 |
| 101245075 | G | G | G | G | G | G | 0.9958 | 0.8593 | 0.9129 | 0.8504 | 0.8534 | 0.9866 |
| 101158538 | A | G | A | G | G | G | 0.9471 | 0.8909 | 0.8710 | 0.9581 | 0.8961 | 0.9046 |
| rs2535386 | A | A | A | A | A | A | 0.9273 | 0.9479 | 0.9867 | 0.8918 | 0.9264 | 0.9750 |
| rs6489653 | T | T | T | T | T | T | 0.9453 | 0.9776 | 0.9051 | 0.8547 | 0.9636 | 0.9532 |
| 101137205 | C | G | C | C | G | G | 0.8619 | 0.9503 | 0.9029 | 0.9426 | 0.8845 | 0.9282 |
| 101089311 | T | C | C | C | C | T | 0.8844 | 0.9381 | 0.9719 | 0.8636 | 0.9186 | 0.9652 |
| 101205712 | A | A | A | A | A | A | 0.8513 | 0.9226 | 0.8755 | 0.8999 | 0.9193 | 0.8535 |
| 101124605 | G | G | G | G | G | G | 0.8981 | 0.9093 | 0.9075 | 0.8676 | 0.8931 | 0.9258 |
| 101025989 | G | T | T | G | G | T | 0.9695 | 0.9016 | 0.8722 | 0.8821 | 0.9787 | 0.9273 |
| rs4766370 | T | A | A | T | T | A | 0.8886 | 0.9166 | 0.8762 | 0.8767 | 0.9890 | 0.8536 |

FIG. 22

| snp_id | true_value | true_hyp | ee | pp | mm | SnipProb | HypProb |
|---|---|---|---|---|---|---|---|
| 101100940 | CT | p2 m2 | CT | TC | CT | 0.8416 | 0.5206 |
| 101164838 | CT | p2 m1 | TC | TC | TC | 0.9061 | 0.5206 |
| rs1463589 | CC | p2 m1 | CC | TC | CC | 0.9946 | 0.5206 |
| 101028396 | GC | p2 m1 | CG | CG | CC | 0.9791 | 0.5206 |
| 101204217 | AG | p2 m2 | AG | GA | GG | 0.9577 | 0.5206 |
| 101214313 | GA | p1 m2 | AG | GA | GA | 0.9308 | 0.5206 |
| 101231593 | GA | p1 m2 | GA | GG | AA | 1.0000 | 0.5206 |
| rs1426442 | CG | p1 m2 | GC | CG | CG | 0.9198 | 0.5206 |
| rs7486852 | CC | p1 m2 | CC | CT | TC | 0.9138 | 0.5206 |
| 101266729 | AG | p1 m2 | AG | AG | AG | 0.9296 | 0.5206 |

FIG. 23

| snp_id | true_value | true_hyp | ee | pp | mm | SnipProb | HypProb |
|---|---|---|---|---|---|---|---|
| 101019515 | GG | p1 m1 | GG | GG | GG | 1.0000 | 0.9890 |
| 101100940 | TC | p1 m1 | CT | TC | CT | 0.9946 | 0.9890 |
| 101160854 | AA | p1 m1 | AA | AA | AA | 1.0000 | 0.9890 |
| rs4980809 | GA | p1 m1 | AG | GA | AG | 0.9961 | 0.9890 |
| 101058479 | GG | p1 m1 | GA | GA | GA | 0.9957 | 0.9890 |
| 101236938 | GG | p1 m1 | GG | GG | GA | 1.0000 | 0.9890 |
| rs7137405 | TT | p1 m1 | TT | TT | TA | 1.0000 | 0.9890 |
| 101251161 | GG | p1 m1 | GG | GG | GG | 1.0000 | 0.9890 |
| 101270051 | GG | p1 m1 | GG | GG | GA | 1.0000 | 0.9890 |
| rs215227 | GG | p1 m1 | GG | GG | GA | 1.0000 | 0.9890 |
| 101245075 | GG | p1 m1 | GG | GG | GG | 1.0000 | 0.9890 |
| 101158538 | AG | p1 m1 | AG | AG | GG | 0.9977 | 0.9890 |
| rs2535386 | AA | p1 m1 | AA | AA | AA | 1.0000 | 0.9890 |
| rs6489653 | TT | p1 m1 | TT | TT | TT | 1.0000 | 0.9890 |
| 101137205 | CG | p1 m1 | CG | CC | GG | 1.0000 | 0.9890 |
| 101089311 | CC | p1 m1 | TC | CC | CT | 0.9940 | 0.9890 |
| 101205712 | AA | p1 m1 | AA | AA | AA | 1.0000 | 0.9890 |
| 101124605 | GG | p1 m1 | GG | GG | GG | 1.0000 | 0.9890 |
| 101025989 | TG | p1 m1 | GT | TG | GT | 0.9973 | 0.9890 |
| rs4766370 | AT | p1 m1 | TA | AT | TA | 0.9973 | 0.9890 |

FIG. 24

|          |      |      | DHAlgorithm1 |           | DHAlgorithm2 |           |
|----------|------|------|--------------|-----------|--------------|-----------|
| Pop.Freq | ph   | pd   | P1accuracy   | P2accuracy| P1accuracy   | P2accuracy|
| data     | 0.95 | 0.95 | 0.982        | 0.951     | 0.95         | 0.906     |
| data     | 0.75 | 0.75 | 0.891        | 0.811     | 0.749        | 0.618     |
| data     | 0.25 | 0.25 | 0.71         | 0.71      | 0.253        | 0.25      |
| data     | 0.5  | 0.9  | 0.849        | 0.838     | 0.499        | 0.768     |
| data     | 0.9  | 0.5  | 0.942        | 0.734     | 0.898        | 0.347     |
| data     | 0.6  | 0.8  | 0.852        | 0.816     | 0.601        | 0.673     |
| uniform  | 0.95 | 0.95 | 0.95         | 0.906     | 0.949        | 0.905     |
| uniform  | 0.75 | 0.75 | 0.749        | 0.612     | 0.749        | 0.612     |
| uniform  | 0.25 | 0.25 | 0.25         | 0.248     | 0.25         | 0.25      |
| uniform  | 0.5  | 0.9  | 0.69         | 0.669     | 0.501        | 0.671     |
| uniform  | 0.9  | 0.5  | 0.901        | 0.412     | 0.901        | 0.413     |
| uniform  | 0.6  | 0.8  | 0.678        | 0.618     | 0.6          | 0.618     |

FIG. 25

|          |      |      |      | PSAlgorithm1 |           | PSAlgorithm2 |           |
|----------|------|------|------|--------------|-----------|--------------|-----------|
| Pop.Freq | ph   | pd   | pe   | P1accuracy   | P2accuracy| P1accuracy   | P2accuracy|
| data     | 0.95 | 0.95 | 0.95 | 0.834        | 0.815     | 0.928        | 0.931     |
| data     | 0.75 | 0.75 | 0.75 | 0.797        | 0.769     | 0.819        | 0.819     |
| data     | 0.25 | 0.25 | 0.25 | 0.711        | 0.682     | 0.703        | 0.687     |
| data     | 0.5  | 0.9  | 0.9  | 0.849        | 0.838     | 0.866        | 0.864     |
| data     | 0.9  | 0.5  | 0.5  | 0.792        | 0.809     | 0.756        | 0.752     |
| data     | 0.6  | 0.8  | 0.8  | 0.777        | 0.788     | 0.835        | 0.828     |
| uniform  | 0.95 | 0.95 | 0.95 | 0.673        | 0.631     | 0.898        | 0.901     |
| uniform  | 0.75 | 0.75 | 0.75 | 0.549        | 0.497     | 0.635        | 0.65      |
| uniform  | 0.25 | 0.25 | 0.25 | 0.239        | 0.249     | 0.252        | 0.25      |
| uniform  | 0.5  | 0.9  | 0.9  | 0.601        | 0.611     | 0.814        | 0.818     |
| uniform  | 0.9  | 0.5  | 0.5  | 0.459        | 0.391     | 0.449        | 0.468     |
| uniform  | 0.6  | 0.8  | 0.8  | 0.544        | 0.511     | 0.672        | 0.679     |

FIG. 26

SYSTEM AND METHOD FOR CLEANING NOISY GENETIC DATA FROM TARGET INDIVIDUALS USING GENETIC DATA FROM GENETICALLY RELATED INDIVIDUALS

CROSS-REFERENCES TO RELATED APPLICATIONS

This application is a continuation of U.S. Utility application Ser. No. 15/191,197, filed Jun. 23, 2016, which is a continuation of U.S. Utility application Ser. No. 13/793,133 (now U.S. Pat. No. 9,424,392), filed Mar. 11, 2013, which is a continuation of U.S. Utility application Ser. No. 11/603,406 (now U.S. Pat. No. 8,532,930), filed Nov. 22, 2006, which claims the benefit under 35 U.S.C. §119(e) of the following U.S. Provisional Patent Applications: Ser. No. 60/739,882, filed Nov. 26, 2005; Ser. No. 60/742,305, filed Dec. 6, 2005; Ser. No. 60/754,396, filed Dec. 29, 2005; Ser. No. 60/774,976, filed Feb. 21, 2006; Ser. No. 60/789,506, filed Apr. 4, 2006; Ser. No. 60/817,741, filed Jun. 30, 2006; and Ser. No. 60/846,610, filed Sep. 22, 2006; the disclosures of the patent applications cited in this paragraph are each incorporated by reference herein in their entirety.

BACKGROUND OF THE INVENTION

Field of the Invention

The invention relates generally to the field of acquiring, manipulating and using genetic data for medically predictive purposes, and specifically to a system in which imperfectly measured genetic data is made more precise by using known genetic data of genetically related individuals, thereby allowing more effective identification of genetic irregularities that could result in various phenotypic outcomes.

Description of the Related Art

Current methods of prenatal diagnosis can alert physicians and parents to abnormalities in growing fetuses. Without prenatal diagnosis, one in 50 babies is born with serious physical or mental handicap, and as many as one in 30 will have some form of congenital malformation. Unfortunately, standard methods require invasive testing and carry a roughly 1 percent risk of miscarriage. These methods include amniocentesis, chorion villus biopsy and fetal blood sampling. Of these, amniocentesis is the most common procedure; in 2003, it was performed in approximately 3% of all pregnancies, though its frequency of use has been decreasing over the past decade and a half. A major drawback of prenatal diagnosis is that given the limited courses of action once an abnormality has been detected, it is only valuable and ethical to test for very serious defects. As a result, prenatal diagnosis is typically only attempted in cases of high-risk pregnancies, where the elevated chance of a defect combined with the seriousness of the potential abnormality outweighs the risks. A need exists for a method of prenatal diagnosis that mitigates these risks.

It has recently been discovered that cell-free fetal DNA and intact fetal cells can enter maternal blood circulation. Consequently, analysis of these cells can allow early Non-Invasive Prenatal Genetic Diagnosis (NIPGD). A key challenge in using NIPGD is the task of identifying and extracting fetal cells or nucleic acids from the mother's blood. The fetal cell concentration in maternal blood depends on the stage of pregnancy and the condition of the fetus, but estimates range from one to forty fetal cells in every milliliter of maternal blood, or less than one fetal cell per 100,000 maternal nucleated cells. Current techniques are able to isolate small quantities of fetal cells from the mother's blood, although it is very difficult to enrich the fetal cells to purity in any quantity. The most effective technique in this context involves the use of monoclonal antibodies, but other techniques used to isolate fetal cells include density centrifugation, selective lysis of adult erythrocytes, and FACS. Fetal DNA isolation has been demonstrated using PCR amplification using primers with fetal-specific DNA sequences. Since only tens of molecules of each embryonic SNP are available through these techniques, the genotyping of the fetal tissue with high fidelity is not currently possible.

Much research has been done towards the use of pre-implantation genetic diagnosis (PGD) as an alternative to classical prenatal diagnosis of inherited disease. Most PGD today focuses on high-level chromosomal abnormalities such as aneuploidy and balanced translocations with the primary outcomes being successful implantation and a take-home baby. A need exists for a method for more extensive genotyping of embryos at the pre-implantation stage. The number of known disease associated genetic alleles is currently at 389 according to OMIM and steadily climbing. Consequently, it is becoming increasingly relevant to analyze multiple embryonic SNPs that are associated with disease phenotypes. A clear advantage of pre-implantation genetic diagnosis over prenatal diagnosis is that it avoids some of the ethical issues regarding possible choices of action once undesirable phenotypes have been detected.

Many techniques exist for isolating single cells. The FACS machine has a variety of applications; one important application is to discriminate between cells based on size, shape and overall DNA content. The FACS machine can be set to sort single cells into any desired container. Many different groups have used single cell DNA analysis for a number of applications, including prenatal genetic diagnosis, recombination studies, and analysis of chromosomal imbalances. Single-sperm genotyping has been used previously for forensic analysis of sperm samples (to decrease problems arising from mixed samples) and for single-cell recombination studies.

Isolation of single cells from human embryos, while highly technical, is now routine in in vitro fertilization clinics. To date, the vast majority of prenatal diagnoses have used fluorescent in situ hybridization (FISH), which can determine large chromosomal aberrations (such as Down syndrome, or trisomy 21) and PCR/electrophoresis, which can determine a handful of SNPs or other allele calls. Both polar bodies and blastomeres have been isolated with success. It is critical to isolate single blastomeres without compromising embryonic integrity. The most common technique is to remove single blastomeres from day 3 embryos (6 or 8 cell stage). Embryos are transferred to a special cell culture medium (standard culture medium lacking calcium and magnesium), and a hole is introduced into the zona pellucida using an acidic solution, laser, or mechanical drilling. The technician then uses a biopsy pipette to remove a single visible nucleus. Clinical studies have demonstrated that this process does not decrease implantation success, since at this stage embryonic cells are undifferentiated.

There are three major methods available for whole genome amplification (WGA): ligation-mediated PCR (LM-PCR), degenerate oligonucleotide primer PCR (DOP-PCR), and multiple displacement amplification (MDA). In LM-PCR, short DNA sequences called adapters are ligated to blunt ends of DNA. These adapters contain universal amplification sequences, which are used to amplify the DNA by PCR. In DOP-PCR, random primers that also contain universal amplification sequences are used in a first round of annealing and PCR. Then, a second round of PCR is used to amplify the sequences further with the universal primer sequences. Finally, MDA uses the phi-29 polymerase, which is a highly processive and non-specific enzyme that replicates DNA and has been used for single-cell analysis. Of the three methods, DOP-PCR reliably produces large quantities of DNA from small quantities of DNA, including single copies of chromosomes. On the other hand, MDA is the fastest method, producing hundred-fold amplification of DNA in a few hours. The major limitations to amplifying material from a single cell are (1) necessity of using extremely dilute DNA concentrations or extremely small volume of reaction mixture, and (2) difficulty of reliably dissociating DNA from proteins across the whole genome. Regardless, single-cell whole genome amplification has been used successfully for a variety of applications for a number of years.

There are numerous difficulties in using DNA amplification in these contexts. Amplification of single-cell DNA (or DNA from a small number of cells, or from smaller amounts of DNA) by PCR can fail completely, as reported in 5-10% of the cases. This is often due to contamination of the DNA, the loss of the cell, its DNA, or accessibility of the DNA during the PCR reaction. Other sources of error that may arise in measuring the embryonic DNA by amplification and microarray analysis include transcription errors introduced by the DNA polymerase where a particular nucleotide is incorrectly copied during PCR, and microarray reading errors due to imperfect hybridization on the array. The biggest problem, however, remains allele drop-out (ADO) defined as the failure to amplify one of the two alleles in a heterozygous cell. ADO can affect up to more than 40% of amplifications and has already caused PGD misdiagnoses. ADO becomes a health issue especially in the case of a dominant disease, where the failure to amplify can lead to implantation of an affected embryo. The need for more than one set of primers per each marker (in heterozygotes) complicate the PCR process. Therefore, more reliable PCR assays are being developed based on understanding the ADO origin. Reaction conditions for single-cell amplifications are under study. The amplicon size, the amount of DNA degradation, freezing and thawing, and the PCR program and conditions can each influence the rate of ADO.

All those techniques, however, depend on the minute DNA amount available for amplification in the single cell. This process is often accompanied by contamination. Proper sterile conditions and microsatellite sizing can exclude the chance of contaminant DNA as microsatellite analysis detected only in parental alleles exclude contamination. Studies to reliably transfer molecular diagnostic protocols to the single-cell level have been recently pursued using first-round multiplex PCR of microsatellite markers, followed by real-time PCR and microsatellite sizing to exclude chance contamination. Multiplex PCR allows for the amplification of multiple fragments in a single reaction, a crucial requirement in the single-cell DNA analysis. Although conventional PCR was the first method used in PGD, fluorescence in situ hybridization (FISH) is now common. It is a delicate visual assay that allows the detection of nucleic acid within undisturbed cellular and tissue architecture. It relies firstly on the fixation of the cells to be analyzed. Consequently, optimization of the fixation and storage condition of the sample is needed, especially for single-cell suspensions.

Advanced technologies that enable the diagnosis of a number of diseases at the single-cell level include interphase chromosome conversion, comparative genomic hybridization (CGH), fluorescent PCR, and whole genome amplification. The reliability of the data generated by all of these techniques rely on the quality of the DNA preparation. PGD is also costly, consequently there is a need for less expensive approaches, such as mini-sequencing. Unlike most mutation-detection techniques, mini-sequencing permits analysis of very small DNA fragments with low ADO rate. Better methods for the preparation of single-cell DNA for amplification and PGD are therefore needed and are under study. The more novel microarrays and comparative genomic hybridization techniques, still ultimately rely on the quality of the DNA under analysis.

Several techniques are in development to measure multiple SNPs on the DNA of a small number of cells, a single cell (for example, a blastomere), a small number of chromosomes, or from fragments of DNA. There are techniques that use Polymerase Chain Reaction (PCR), followed by microarray genotyping analysis. Some PCR-based techniques include whole genome amplification (WGA) techniques such as multiple displacement amplification (MDA), and MOLECULAR INVERSION PROBES (MIPs) that perform genotyping using multiple tagged oligonucleotides that may then be amplified using PCR with a single pair of primers. An example of a non-PCR based technique is fluorescence in situ hybridization (FISH). It is apparent that the techniques will be severely error-prone due to the limited amount of genetic material which will exacerbate the impact of effects such as allele drop-outs, imperfect hybridization, and contamination.

Many techniques exist which provide genotyping data. TAQMAN is a unique genotyping technology produced and distributed by Applied Biosystems. TAQMAN uses polymerase chain reaction (PCR) to amplify sequences of interest. During PCR cycling, an allele specific minor groove binder (MGB) probe hybridizes to amplified sequences. Strand synthesis by the polymerase enzymes releases reporter dyes linked to the MGB probes, and then the TAQMAN optical readers detect the dyes. In this manner, TAQMAN achieves quantitative allelic discrimination. Compared with array based genotyping technologies, TAQMAN is quite expensive per reaction (~$0.40/reaction), and throughput is relatively low (384 genotypes per run). While only 1ng of DNA per reaction is necessary, thousands of genotypes by TAQMAN requires microgram quantities of DNA, so TAQMAN does not necessarily use less DNA than microarrays. However, with respect to the IVF genotyping workflow, TAQMAN is the most readily applicable technology. This is due to the high reliability of the assays and, most importantly, the speed and ease of the assay (~3 hours per run and minimal molecular biological steps). Also unlike many array technologies (such as 500 k AFFMETRIX arrays), TAQMAN is highly customizable, which is important for the IVF market. Further. TAQMAN is highly quantitative, so aneuploidies could be detected with this technology alone.

ILLUMINA has recently emerged as a leader in high-throughput genotyping. Unlike AFFMETRIX, ILLUMINA genotyping arrays do not rely exclusively on hybridization. Instead, ILLUMINA technology uses an allele-specific DNA extension step, which is much more sensitive and specific than hybridization alone, for the original sequence detection. Then, all of these alleles are amplified in multiplex by PCR, and then these products hybridized to bead arrays. The beads on these arrays contain unique "address" tags, not native sequence, so this hybridization is highly specific and sensitive. Alleles are then called by quantitative scanning of the bead arrays. The Illumina GOLDEN GATE assay system genotypes up to 1536 loci concurrently, so the throughput is better than TAQMAN but not as high as AFFMETRIX 500 k arrays. The cost of ILLUMINA genotypes is lower than TAQMAN, but higher than AFFMETRIX arrays. Also, the ILLUMINA platform takes as long to complete as the 500 k AFFMETRIX arrays (up to 72 hours), which is problematic for IVF genotyping. However, ILLUMINA has a much better call rate, and the assay is quantitative, so aneuploidies are detectable with this technology. ILLUMINA technology is much more flexible in choice of SNPs than 500 k AFFMETRIX arrays.

One of the highest throughput techniques, which allows for the measurement of up to 250,000 SNPs at a time, is the AFFMETRIX GeneChip 500K genotyping array. This technique also uses PCR, followed by analysis by hybridization and detection of the amplified DNA sequences to DNA probes, chemically synthesized at different locations on a quartz surface. A disadvantage of these arrays are the low flexibility and the lower sensitivity. There are modified approaches that can increase selectivity, such as the "perfect match" and "mismatch probe" approaches, but these do so at the cost of the number of SNPs calls per array.

Pyrosequencing, or sequencing by synthesis, can also be used for genotyping and SNP analysis. The main advantages to pyrosequencing include an extremely fast turnaround and unambiguous SNP calls, however, the assay is not currently conducive to high-throughput parallel analysis. PCR followed by gel electrophoresis is an exceedingly simple technique that has met the most success in preimplantation diagnosis. In this technique, researchers use nested PCR to amplify short sequences of interest. Then, they run these DNA samples on a special gel to visualize the PCR products. Different bases have different molecular weights, so one can determine base content based on how fast the product runs in the gel. This technique is low-throughput and requires subjective analyses by scientists using current technologies, but has the advantage of speed (1-2 hours of PCR, 1 hour of gel electrophoresis). For this reason, it has been used previously for prenatal genotyping for a myriad of diseases, including: thalassaemia, neurofibromatosis type 2, leukocyte adhesion deficiency type I, Hallopeau-Siemens disease, sickle-cell anemia, retinoblastoma, Pelizaeus-Merzbacher disease, Duchenne muscular dystrophy, and Currarino syndrome.

Another promising technique that has been developed for genotyping small quantities of genetic material with very high fidelity is MOLECULAR INVERSION PROBES (MIPs), such as AFFMETRIX's GENFLEX Arrays. This technique has the capability to measure multiple SNPs in parallel: more than 10,000 SNPS measured in parallel have been verified. For small quantities of genetic material, call rates for this technique have been established at roughly 95%, and accuracy of the calls made has been established to be above 99%. So far, the technique has been implemented for quantities of genomic data as small as 150 molecules for a given SNP. However, the technique has not been verified for genomic data from a single cell, or a single strand of DNA, as would be required for pre-implantation genetic diagnosis.

The MIP technique makes use of padlock probes which are linear oligonucleotides whose two ends can be joined by ligation when they hybridize to immediately adjacent target sequences of DNA. After the probes have hybridized to the genomic DNA, a gap-fill enzyme is added to the assay which can add one of the four nucleotides to the gap. If the added nucleotide (A,C,T,G) is complementary to the SNP under measurement, then it will hybridize to the DNA, and join the ends of the padlock probe by ligation. The circular products, or closed padlock probes, are then differentiated from linear probes by exonucleolysis. The exonuclease, by breaking down the linear probes and leaving the circular probes, will change the relative concentrations of the closed vs. the unclosed probes by a factor of 1000 or more. The probes that remain are then opened at a cleavage site by another enzyme, removed from the DNA, and amplified by PCR. Each probe is tagged with a different tag sequence consisting of 20 base tags (16,000 have been generated), and can be detected, for example, by the AFFMETRIX GENFLEX Tag Array. The presence of the tagged probe from a reaction in which a particular gap-fill enzyme was added indicates the presence of the complimentary amino acid on the relevant SNP.

The molecular biological advantages of MIPS include: (1) multiplexed genotyping in a single reaction, (2) the genotype "call" occurs by gap fill and ligation, not hybridization, and (3) hybridization to an array of universal tags decreases false positives inherent to most array hybridizations. In traditional 500K, TAQMAN and other genotyping arrays, the entire genomic sample is hybridized to the array, which contains a variety of perfect match and mismatch probes, and an algorithm calls likely genotypes based on the intensities of the mismatch and perfect match probes. Hybridization, however, is inherently noisy, because of the complexities of the DNA sample and the huge number of probes on the arrays. MIPs, on the other hand, uses multiplex probes (i.e., not on an array) that are longer and therefore more specific, and then uses a robust ligation step to circularize the probe. Background is exceedingly low in this assay (due to specificity), though allele dropout may be high (due to poor performing probes).

When this technique is used on genomic data from a single cell (or small numbers of cells) it will—like PCR based approaches—suffer from integrity issues. For example, the inability of the padlock probe to hybridize to the genomic DNA will cause allele dropouts. This will be exacerbated in the context of in-vitro fertilization since the efficiency of the hybridization reaction is low, and it needs to proceed relatively quickly in order to genotype the embryo in a limited time period. Note that the hybridization reaction can be reduced well below vendor-recommended levels, and micro-fluidic techniques may also be used to accelerate the hybridization reaction. These approaches to reducing the time for the hybridization reaction will result in reduced data quality.

Once the genetic data has been measured, the next step is to use the data for predictive purposes. Much research has been done in predictive genomics, which tries to understand the precise functions of proteins, RNA and DNA so that phenotypic predictions can be made based on genotype. Canonical techniques focus on the function of Single-Nucleotide Polymorphisms (SNP); but more advanced methods are being brought to bear on multi-factorial phenotypic features. These methods include techniques, such as linear regression and nonlinear neural networks, which attempt to determine a mathematical relationship between a set of genetic and phenotypic predictors and a set of measured outcomes. There is also a set of regression analysis techniques, such as Ridge regression, log regression and stepwise selection, that are designed to accommodate sparse data sets where there are many potential predictors relative to the number of outcomes, as is typical of genetic data, and which apply additional constraints on the regression parameters so that a meaningful set of parameters can be resolved even when the data is underdetermined. Other techniques apply principal component analysis to extract information from undetermined data sets. Other techniques, such as decision trees and contingency tables, use strategies for subdividing subjects based on their independent variables in order to place subjects in categories or bins for which the phenotypic outcomes are similar. A recent technique, termed logical regression, describes a method to search for different logical interrelationships between categorical independent variables in order to model a variable that depends on interactions between multiple independent variables related to genetic data. Regardless of the method used, the quality of the prediction is naturally highly dependent on the quality of the genetic data used to make the prediction.

Normal humans have two sets of 23 chromosomes in every diploid cell, with one copy coming from each parent. Aneuploidy, a cell with an extra or missing chromosomes, and uniparental disomy, a cell with two of a given chromosome that originate from one parent, are believed to be responsible for a large percentage of failed implantations, miscarriages, and genetic diseases. When only certain cells in an individual are aneuploid, the individual is said to exhibit mosaicism. Detection of chromosomal abnormalities can identify individuals or embryos with conditions such as Down syndrome, Klinefelter's syndrome, and Turner syndrome, among others, in addition to increasing the chances of a successful pregnancy. Testing for chromosomal abnormalities is especially important as mothers age: between the ages of 35 and 40 it is estimated that between 40% and 50% of the embryos are abnormal, and above the age of 40, more than half of the embryos are abnormal.

Karyotyping, the traditional method used for the prediction of aneuploides and mosaicism is giving way to other more high throughput, more cost effective methods. One method that has attracted much attention recently is Flow cytometry (FC) and fluorescence in situ hybridization (FISH) which can be used to detect aneuploidy in any phase of the cell cycle. One advantage of this method is that it is less expensive than karyotyping, but the cost is significant enough that generally a small selection of chromosomes are tested (usually chromosomes 13, 18, 21, X, Y, also sometimes 8, 9, 15, 16, 17, 22); in addition, FISH has a low level of specificity. Using FISH to analyze 15 cells, one can detect mosaicism of 190/% with 95% confidence. The reliability of the test becomes much lower as the level of mosaicism gets lower, and as the number of cells to analyze decreases. The test is estimated to have a false negative rate as high as 15% when a single cell is analyzed. There is a great demand for a method that has a higher throughput, lower cost, and greater accuracy.

Listed here is a set of prior art which is related to the field of the current invention. None of this prior art contains or in any way refers to the novel elements of the current invention. In U.S. Pat. No. 6,720,140, Hartley et al describe a recombinational cloning method for moving or exchanging segments of DNA molecules using engineered recombination sites and recombination proteins. In U.S. Pat. No. 6,489,135 Parrott et al. provide methods for determining various biological characteristics of in vitro fertilized embryos, including overall embryo health, implantability, and increased likelihood of developing successfully to term by analyzing media specimens of in vitro fertilization cultures for levels of bioactive lipids in order to determine these characteristics. In US Patent Application 20040033596 Threadgill et al. describe a method for preparing homozygous cellular libraries useful for in vitro phenotyping and gene mapping involving site-specific mitotic recombination in a plurality of isolated parent cells. In U.S. Pat. No. 5,994,148 Stewart et al. describe a method of determining the probability of an in vitro fertilization (IVF) being successful by measuring Relaxin directly in the serum or indirectly by culturing granulosa lutein cells extracted from the patient as part of an IVF/ET procedure. In U.S. Pat. No. 5,635,366 Cooke et al. provide a method for predicting the outcome of IVF by determining the level of 11β-hydroxysteroid dehydrogenase (11☐β-HSD) in a biological sample from a female patient. In U.S. Pat. No. 7,058,616 Larder et al. describe a method for using a neural network to predict the resistance of a disease to a therapeutic agent. In U.S. Pat. No. 6,958,211 Vingerhoets et al. describe a method wherein the integrase genotype of a given HIV strain is simply compared to a known database of HIV integrase genotype with associated phenotypes to find a matching genotype. In U.S. Pat. No. 7,058,517 Denton et al. describe a method wherein an individual's haplotypes are compared to a known database of haplotypes in the general population to predict clinical response to a treatment. In U.S. Pat. No. 7,035,739 Schadt at al. describe a method is described wherein a genetic marker map is constructed and the individual genes and traits are analyzed to give a gene-trait locus data, which are then clustered as a way to identify genetically interacting pathways, which are validated using multivariate analysis. In U.S. Pat. No. 6,025,128 Veltri et al. describe a method involving the use of a neural network utilizing a collection of biomarkers as parameters to evaluate risk of prostate cancer recurrence.

The cost of DNA sequencing is dropping rapidly, and in the near future individual genomic sequencing for personal benefit will become more common. Knowledge of personal genetic data will allow for extensive phenotypic predictions to be made for the individual. In order to make accurate phenotypic predictions high quality genetic data is critical, whatever the context. In the case of prenatal or pre-implantation genetic diagnoses a complicating factor is the relative paucity of genetic material available. Given the inherently noisy nature of the measured genetic data in cases where limited genetic material is used for genotyping, there is a great need for a method which can increase the fidelity of, or clean, the primary data.

SUMMARY OF THE INVENTION

The system disclosed enables the cleaning of incomplete or noisy genetic data using secondary genetic data as a source of information. While the disclosure focuses on genetic data from human subjects, and more specifically on as-yet not implanted embryos or implanted fetuses, it should be noted that the methods disclosed apply to the genetic data of a range of organisms, in a range of contexts. The techniques described for cleaning genetic data are most relevant in the context of pre-implantation diagnosis during in-vitro fertilization, prenatal diagnosis in conjunction with amniocentesis, chorion villus biopsy, and fetal blood sampling, and non-invasive prenatal diagnosis, where a small quantity of fetal genetic material is isolated from maternal blood. The diagnoses may focus on inheritable diseases, increased likelihoods of defects or abnormalities, as well as making phenotype predictions for individuals to enhance clinical and lifestyle decisions. The invention addresses the shortcomings of prior art that are discussed above.

In one aspect of the invention, methods make use of imperfect knowledge of the genetic data of the mother and the father, together with the knowledge of the mechanism of meiosis and the imperfect measurement of the embryonic DNA, in order to reconstruct, in silico, the embryonic DNA at the location of key SNPs with a high degree of confidence. It is important to note that the parental data allows the reconstruction not only of SNPs that were measured poorly, but also of insertions, deletions, and of SNPs or whole regions of DNA that were not measured at all.

The disclosed method is applicable in the context of in-vitro fertilization, where a very small number of blastomeres are available for genotyping from each embryo being considered for implantation. The disclosed method is equally applicable to the context of Non-Invasive Prenatal Diagnosis (NIPD) where only a small number of fetal cells, or fragments of fetal DNA, have been isolated from the mother's blood. The disclosed method is more generally applicable in any case where a limited amount of genetic data is available from the target genome, and additional genetic data is available from individuals who are genetically related to the target.

In one aspect of the invention, the fetal or embryonic genomic data which has been reconstructed can be used to detect if the cell is aneuploid, that is, if fewer or more than two of a particular chromosome is present in a cell. A common example of this condition is trisomy-21, which gives rise to Down syndrome. The reconstructed data can also be used to detect for uniparental disomy, a condition in which two of a given chromosome are present, both of which originate from one parent. This is done by creating a set of hypotheses about the potential states of the DNA, and testing to see which one has the highest probability of being true given the measured data. Note that the use of high throughput genotyping data for screening for aneuploidy enables a single blastomere from each embryo to be used both to measure multiple disease-linked loci as well as screen for aneuploidy.

In another aspect of the invention, the direct measurements of the amount of genetic material, amplified or unamplified, present at a plurality of loci, can be used to detect for aneuploides, or uniparental disomy. The idea behind this method is simply that the amount of genetic material present during amplification is proportional to the amount of genetic information in the initial sample, and measuring these levels at multiple loci will give a statistically significant result.

In another aspect of the invention, the disclosed method can clean genetic material of the individual which has been contaminated by foreign DNA or RNA by identifying the data generated by extraneous genetic materials. The spurious signals generated by the contaminating DNA can be recognized in a manner similar to that way that chromosome-wide anomalous signals generated by aneuploides can be detected.

In another aspect of the invention, target cells are isolated, the genetic data contained in those cells are amplified, and measurements of multiple SNPs are made using a combination of one or more of the following techniques: PCR-based amplification techniques, PCR-based measurement techniques, or detection techniques based on MOLECULAR INVERSION PROBES, or microarrays such as the GENECHIP or TAQMAN systems. This genetic data is then used in the system described herein.

In another aspect of the invention, the genetic data of an individual can be cleaned using diploid and haploid data from both parents. Alternately, haploid data from a parent can be simulated if diploid and haploid data of the parent's parent can be measured. In another aspect, genetic data from any person of a known genetic relation to the individual can be used to clean the data of the individual, including parents, siblings, grandparents, offspring, cousins, uncles, aunts etc.

In another aspect of the invention, the target and/or related individual's genetic data may be partly or wholly known in silico, obviating the need for some direct measurements. Portions of the genetic data can be generated in silico by means of an informatics approach utilizing a hidden Markov model.

In another aspect of the invention, it is possible to estimate the confidence one has in the determination of those SNPs.

Note that the techniques described herein are relevant both to measurements of genetic material in one, or a small number of cells, as well as to measurements on smaller amounts of DNA such as that which can be isolated from the mother's blood in the context of Non-invasive Prenatal Diagnosis (NIPD). Also note that this method can be equally applied to genomic data in silico, i.e. not directly measured from genetic material.

It will be recognized by a person of ordinary skill in the art, given the benefit of this disclosure, aspects and embodiments that may implement one or more of the systems, methods, and features, disclosed herein.

BRIEF DESCRIPTION OF THE DRAWINGS

FIG. 20: a summary of different aneuploidy detection techniques

FIG. 21: an example of input data for the method described using SNPs with a low degree of cosegregation.

FIG. 22: an example of input data for the method described using SNPs with a high degree of cosegregation.

FIG. 23: an example of the output data for the input data shown in FIG. 21.

FIG. 24: an example of the output data for the input data shown in FIG. 23.

FIG. 25: the results of the preliminary simulation.

FIG. 26: the results of the full simulation of the method.

DETAILED DESCRIPTION OF THE PREFERRED EMBODIMENT

Conceptual Overview of the System

The goal of the disclosed system is to provide highly accurate genomic data for the purpose of genetic diagnoses. In cases where the genetic data of an individual contains a significant amount of noise, or errors, the disclosed system makes use of the similarities between genetic data of related individuals, and the information contained in that secondary genetic data, to clean the noise in the target genome. This is done by determining which segments of chromosomes were involved in gamete formation and where crossovers occurred during meiosis, and therefore which segments of the secondary genomes are expected to be nearly identical to sections of the target genome. In certain situations this method can be used to clean noisy base pair measurements, but it also can be used to infer the identity of individual base pairs or whole regions of DNA that were not measured. In addition, a confidence can be computed for each reconstruction call made. A highly simplified explanation is presented first, making unrealistic assumptions in order to illustrate the concept of the invention. A detailed statistical approach that can be applied to the technology of today is presented afterward.

Another goal of the system is to detect abnormal numbers of chromosomes, sections of chromosomes, and origins of chromosomes. In genetic samples that are aneuploid, have unbalanced translocations, uniparental disomy, or other gross chromosomal abnormalities, the amount of genetic material present at a plurality of loci can be used to determine the chromosomal state of the sample. There are multiple approaches to this method, and several of them are described here. In some approaches, the amount of genetic material present in a sample is sufficient to directly detect aneuploides. In other approaches, the method for cleaning the genetic material can be used to enhance the efficiency of detection of chromosomal imbalances. A confidence can be computed for each chromosomal call made.

Technical Description of the System

A Simplified Example

Figure 1:
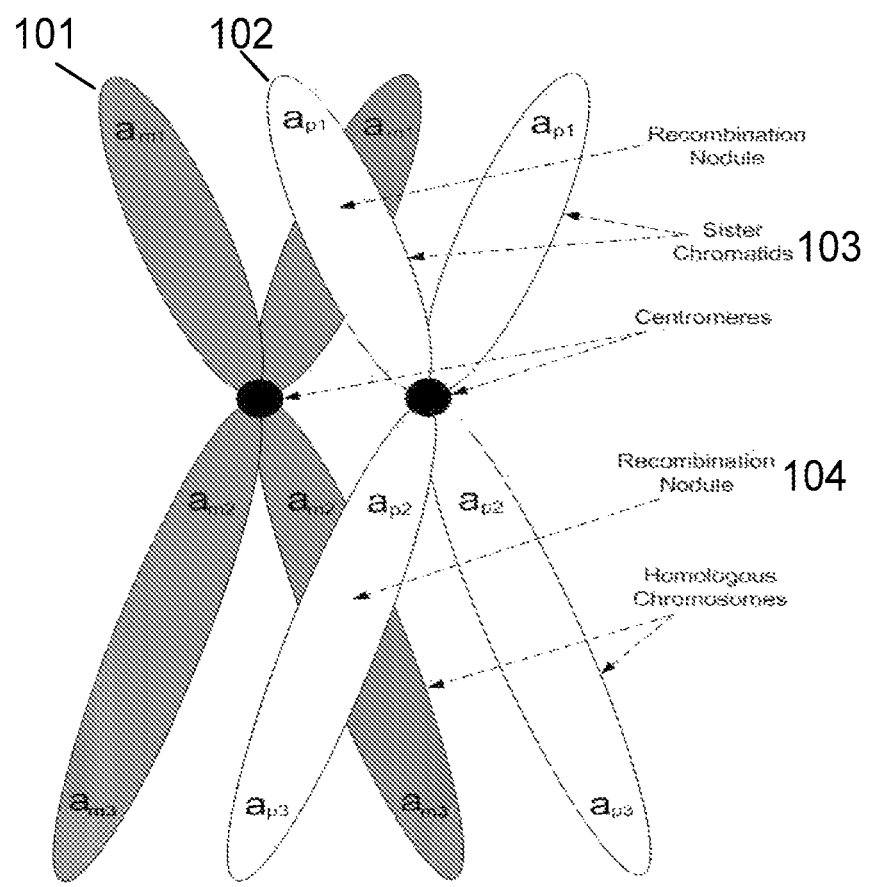
FIG. 1: an illustration of the concept of recombination in meiosis for gamete formation.

FIG. 1 illustrates the process of recombination that occurs during meiosis for the formation of gametes in a parent. The chromosome 101 from the individual's mother is shown in grey. The chromosome 102 from the individual's father is shown in white. During this interval, known as Diplotene, during Prophase I of Meiosis, a tetrad of four chromatids 103 is visible. Crossing over between non-sister chromatids of a homologous pair occurs at the points known as recombination nodules 104. For the purpose of illustration, the example will focus on a single chromosome, and three Single Nucleotide Polymorphisms (SNPs), which are assumed to characterize the alleles of three genes. For this discussion it is assumed that the SNPs may be measured separately on the maternal and paternal chromosomes. This concept can be applied to many SNPs, many alleles characterized by multiple SNPs, many chromosomes, and to the current genotyping technology where the maternal and paternal chromosomes cannot be individually isolated before genotyping.

Attention must be paid to the points of potential crossing over in between the SNPs of interest. The set of alleles of the three maternal genes may be described as $(a_{m1}, a_{m2}, a_{m3})$ corresponding to SNPs ($SNP_1$, $SNP_2$, $SNP_3$). The set of alleles of the three paternal genes may be described as $(a_{p1}, a_{p2}, a_{p3})$. Consider the recombination nodules formed in FIG. 1, and assume that there is just one recombination for each pair of recombining chromatids. The set of gametes that are formed in this process will have gene alleles: $(a_{m1}, a_{m2}, a_{p3})$, $(a_{m1}, a_{p2}, a_{p3})$, $(a_{p1}, a_{m2}, a_{p3})$, $(a_{p1}, a_{p2}, a_{m3})$. In the case with no crossing over of chromatids, the gametes will have alleles $(a_{m1}, a_{m2}, a_{m3})$, $(a_{p1}, a_{p2}, a_{p3})$. In the case with two points of crossing over in the relevant regions, the gametes will have alleles $(a_{m1}, a_{p2}, a_{m3})$, $(a_{p1}, a_{m2}, a_{p3})$. These eight different combinations of alleles will be referred to as the hypothesis set of alleles, for that particular parent.

The measurement of the alleles from the embryonic DNA will be noisy. For the purpose of this discussion take a single chromosome from the embryonic DNA, and assume that it came from the parent whose meiosis is illustrated in FIG. 1. The measurements of the alleles on this chromosome can be described in terms of a vector of indicator variables: $A = [A_1\ A_2\ A_3]^T$ where $A_1 = 1$ if the measured allele in the embryonic chromosome is $a_{m1}$, $A_1 = -1$ if the measured allele in the embryonic chromosome is $a_{p1}$, and $A_1 = 0$ if the measured allele is neither $a_{m1}$ or $a_{p1}$. Based on the hypothesis set of alleles for the assumed parent, a set of eight vectors may be created which correspond to all the possible gametes describe above. For the alleles described above, these vectors would be $a_1 = [1\ 1\ 1]^T$, $a_2 = [1\ 1\ -1]^T$, $a_3 = [1\ -1\ 1]^T$, $a_4 = [1\ -1\ -1]^T$, $a_5 = [-1\ 1\ 1]^T$, $a_6 = [-1\ 1\ -1]^T$, $a_7 = [-1\ -1\ 1]^T$, $a_8 = [-1\ -1\ -1]^T$. In this highly simplified application of the system, the likely alleles of the embryo can be determined by performing a simple correlation analysis between the hypothesis set and the measured vectors:

$$i^* = \arg\max_i A^T a_i, \quad i = 1 \ldots 8 \qquad (1)$$

Once $i^*$ is found, the hypothesis $a_{i^*}$ is selected as the most likely set of alleles in the embryonic DNA. This process is then repeated twice, with two different assumptions, namely that the embryonic chromosome came from the mother or the father. That assumption which yields the largest correlation $A^T a_{i^*}$ would be assumed to be correct. In each case a hypothesis set of alleles is used, based on the measurements of the respective DNA of the mother or the father. Note that in a typical embodiment of the disclosed method, one measures a large number of SNPs between those SNPs that are important due to their association with particular disease phenotypes—these will be referred to these as Phenotype-associated SNPs or PSNPs. The Non-phenotype-associated SNPs (NSNPs) between the PSNPs may be chosen a-priori (for example, for developing a specialized genotyping array) by selecting from the NCBI dbSNP database those RefSNPs that tend to differ substantially between individuals. Alternatively, the NSNPs between the PSNPs may be chosen for a particular pair of parents because they differ between the parents. The use of the additional SNPs between the PSNPs enables one to determine with a higher level of confidence whether crossover occurs between the PSNPs. It is important to note that while different "alleles" are referred to in this notation, this is merely a convenience; the SNPs may not be associated with genes that encode proteins.

The System in the Context of Current Technology

In another more complex embodiment, the a-posteriori probability of a set of alleles is computed given a particular measurement, taking into account the probability of particular crossovers. In addition, the scenario typical of microarrays and other genotyping technologies is addressed where SNPs are measured for pairs of chromosomes, rather than for a single chromosome at a time. The measurements of the genotype at the locus i for the embryonic, paternal and maternal chromosomes may be characterized respectively by random variables representing the pairs of SNP measurements $(e_{1,i}, e_{2,i})$, $(p_{1,i}, p_{2,i})$ and $(m_{1,i}, m_{2,i})$. Since one cannot determine the presence of crossovers in the maternal and paternal chromosomes if all measurements are made as pairs, the method is modified: in addition to genotyping the fertilized embryos and paternal and maternal diploid tissue, one haploid cell from each parent, namely, a sperm cell and an egg cell, is also genotyped. The measured alleles of the sperm cell are represented by $p_{1,i}$, i=1 . . . N and the complementary alleles measured from the paternal diploid tissue by $p_{2,i}$. Similarly, the measured alleles of the egg cell are represented by $m_{1,i}$ and their complement in the mother's diploid cell by $m_{2,i}$. These measurements provide no information on where the parental chromosomes crossed over in generating the measured sperm and egg cells. However, one can assume that the sequence of N alleles on the egg or sperm was created from the parental chromosomes by a small number of, or no, crossovers. This is sufficient information to apply the disclosed algorithm. A certain error probability is associated with calling the paternal and maternal SNPs. The estimation of this error probability will vary based on the measurements made $(p_{1,i}, p_{2,i})$ and $(m_{1,i}, m_{2,i})$ and the signal-to-noise ratio for the technology used. Although these error probabilities can be uniquely computed for each locus without affecting the disclosed method, the algebra is simplified here by assuming that the probabilities of correctly calling the paternal and maternal SNPs are constant at $p_p$ and $p_m$ respectively.

Assume that a measurement is performed on the embryonic DNA which is termed measurement M. In addition, the notation is slightly modified so that A is now a set and not a vector: A refers to a particular hypothesis about the combination (or set) of alleles derived from each parent. The set of all possible combinations of alleles A from both parents is denoted as $S_A$. The goal is to determine the combination of alleles (or that hypothesis) $A \in S_A$ with the highest a-posteriori probability, given the measurement M:

$$A^* = \arg\max_A P(A|M), \forall A \in S_A \quad (2)$$

Using the law of conditional probabilities, P(A|M)=P(M|A)P(A)/P(M). Since P(M) is common for all different A's, the optimizing search can be recast as:

$$A^* = \arg\max_A P(M|A)P(A), \forall A \in S_A \quad (3)$$

Now consider the computation of P(M|A). Begin with a single locus i, and let the hypothesis be that this locus on the embryo is derived from the parental SNPs $p_{t,1,i}$ and $m_{t,1,i}$, where the underscore t is used to denote the true value of these Parental SNPs, as opposed to the measurements performed, $p_{1,i}$ and $m_{1,i}$, which may or may not be correct. The true value of the embryonic SNPs is denoted as $(e_{t,1,i}, e_{t,2,i})$. If hypothesis A is true, then $(e_{t,1,i}, e_{t,2,i})=(p_{t,1,i}, m_{t,1,i})$ or $(m_{t,1,i}, p_{t,1,i})$. Since one cannot differentiate which of the measurements $(e_{1,i}, e_{2,i})$ comes from which parent, both orders must be considered so the hypothesis set $A=[(p_{t,1,i}, m_{t,1,i}), (m_{t,1,i}, p_{t,1,i})]$. The probability of a particular measurement M depends on the true values or the underlying states of the parental SNPs, namely $(p_{t,1,i}, p_{t,2,i})$ and $(m_{t,1,i}, m_{t,2,i})$. Since there are four SNPs, $p_{t,1,i}, p_{t,2,i}, m_{t,1,i}, m_{t,2,i}$, and each of these can assume the value of four nucleotide bases, A,C,T,G, there are $4^4$ or 256 possible states. The algorithm is illustrated for one state $s_1$ for which it is assumed that $p_{t,1,i} \neq p_{t,2,i} \neq m_{t,1,i} \neq m_{t,2,i}$. From this explanation, it will be clear how to apply the method to all 256 possible states, $s_k$, k=1 . . . 256. Assume a measurement M of embryonic SNPs $(e_{1,i}, e_{2,i})$ is performed, and the result $e_{1,i}=p_{1,i}, e_{2,i}=m_{1,i}$ is obtained. The a priori probability for this measurement given that hypothesis A and state $s_1$ are true is computed:

$$P(e_{1,i}=p_{1,i}, e_{2,i}=m_{1,i}|A, s_1) = P(e_{t,1,i}=p_{t,1,i}, e_{t,2,i}=m_{t,1,i}|A, s_1)P(e_{1,i}=p_{1,i}|e_{t,1,i}=p_{t,1,i})P(e_{2,i}=m_{1,i}|e_{t,2,i}=m_{t,1,i}) + P(e_{t,1,i}=m_{t,1,i}, e_{t,2,i}=p_{t,1,i}|A, s_1)P(e_{1,i}=p_{1,i}|e_{t,1,i}=m_{t,1,i}, p_{t,1,i} \neq m_{t,1,i})P(e_{2,i}=m_{1,i}|e_{t,2,i}=p_{t,2,i}, p_{t,2,i} \neq m_{t,1,i}) \quad (4)$$

Consider the first expressions in the first term and second term: $P(e_{1,i}=p_{1,i}, e_{2,i}=m_{1,i}|A, s_1) = P(e_{1,i}=m_{1,i}, e_{2,i}=p_{1,i}|A, s_1) = 0.5$ since the hypothesis $A=[(p_{t,1,i}, m_{t,1,i}), (m_{t,1,i}, p_{t,1,i})]$ makes two orderings for the embryonic SNPs equally likely. Now consider the second expression of the first term, $P(e_{1,i}=p_{1,i}|e_{t,1,i}=p_{t,1,i})$, the probability of measuring $e_{1,i}=p_{1,i}$ given the assumption that embryonic SNP $e_{t,1,i}$ actually is derived from paternal SNP $p_{t,1,i}$. The probabilities for correctly measuring the paternal SNPs, maternal SNPs, and embryonic SNPs are $p_p$, $p_m$, and $p_e$. Given the assumption $(e_{t,1,i}=p_{t,1,i})$, the measurement $(e_{1,i}=p_{1,i})$ requires either that both embryonic and paternal SNPs are correctly measured, or that both are incorrectly measured and they happen to be incorrectly measured as the same nucleotide (A, C, T, or G). So, $P(e_{1,i}=p_{1,i}|e_{t,1,i}=p_{t,1,i}) = p_e p_p + (1-p_e)(1-p_p)/3$ where it is assumed for simplicity that the probability of incorrectly calling all of the four nucleotides is equally likely—the algorithm can be easily modified to accommodate different probabilities of calling a particular nucleotide (A,C,T,G) given a measurement on another particular nucleotide. The same approach may be applied to the third expression in the first term to obtain $P(e_{2,i}=m_{1,i}|e_{t,2,i}=m_{t,1,i}) = p_e p_m + (1-p_e)(1-p_m)/3$. Now consider the second expression of the second term. $P(e_{1,i}=p_{1,i}|e_{t,1,i}=m_{t,1,i}, m_{t,1,i} \neq p_{t,1,i})$ requires either that $e_{1,i}$ or $p_{1,i}$ be an incorrect measurement, or that both be incorrect measurements, so that the measured values happen to be equal: $P(e_{1,i}=p_{1,i}|e_{t,1,i}=m_{t,1,i}, m_{t,1,i} \neq p_{t,1,i}) = p_e(1-p_p)/3 + (1-p_e)p_p/3 + (1-p_e)(1-p_p)2/9$. The same argument can be applied to the last expression of the second term to yield $P(e_{2,i}=m_{1,i}|e_{t,2,i}=p_{t,2,i}, m_{t,1,i} \neq p_{t,2,i}) = p_e(1-p_m)3 + (1-p_e)p_m/3 + (1-p_e)(1-p_m)2/9$. Now, combining all of these terms, and making the assumption—merely to simplify the algebra—that $p_e = p_p = p_m = p$, one can compute:

$$P(M(e_{1,i}=p_{1,i}, e_{2,i}=m_{1,i})|A, s_1) = 1/162(160p^4 - 160p^3 + 96p^2 - 28p + 13) \quad (5)$$

Although the computation will vary, a similar conceptual approach to that described here would be used for all 256 possible states, $s_k$, k=1 . . . 256. Computing $P(e_{1,i}=p_{1,i}, e_{2,i}=m_{1,i}|A, s_i)$ for all 256 states $s_i$ and summing over the probability of each $s_i$ one obtains $P(e_{1,i}=p_{1,i}, e_{2,i}=m_{1,i}|A)$. In other words:

$$P(M|A) = \sum_{i=1 \ldots 256} P(M|A, s_i)P(s_i) \quad (6)$$

In order to compute the probabilities of each state $s_i$, $P(s_i)$, one must treat all the separate alleles making up a state as separate events since they are on separate chromosomes, in other words: $P(s_i)=P(p_{t,1,i}, p_{t,2,i}, m_{t,1,i}, m_{t,2,i})=P(p_{t,1,i})P(p_{t,2,i})P(m_{t,1,i})P(m_{t,2,i})$. Bayesian techniques may be applied to estimate the probability distribution for the individual measurements. Every measurement of an allele on the maternal or paternal chromosomes at locus i may be treated as a coin toss experiment to measure the probability of this allele being a particular value (A, C, T or G). These measurements are made on the adult tissue samples and may be treated as being totally reliable, even though pairs of alleles are measured for each SNP, and it is not possible to determine which allele comes from which chromosome. Let $w_{p,1,i}=P(p_{t,1,i})$, corresponding to the probability of the SNP i on the father's chromosome being value $p_{t,1,i}$. In the following explanation, w is used instead of $w_{p,1,i}$. Let the measurements performed on SNP i of the father's chromosome be characterized as collecting data D. One can create a probability distribution for w, p(w) and update this after the data is measurement according to Bayes Theorem: p(w|D)=p(w)p(D|w)/p(D). Assume n alleles of SNP i are observed and that the particular allele corresponding to w comes up h times—in other words, heads is observed h times. The probability of this observation can be characterized by the binomial distribution $$p(D \mid w) = \binom{n}{h} w^h (1-w)^{n-h} \qquad (7)$$

Before data is collected, assume there is a prior distribution p(w) which is uniform between 0 and 1. By applying the Bayes theorem, it is straightforward to show that the resulting distribution for p(w|D) will be a beta distribution of the form:

$$p(w \mid D) = \frac{1}{c} w^h (1-w)^{n-h} \text{ where } c = \int_0^1 w^h (1-w)^{n-h} dw \qquad (8)$$

and c is a normalizing constant. However many times p(w|D) is then updated by applying Bayes theorem and new measurements, it will continue to have a beta distribution as above. The estimates of p(w) are updated every time a new measurement is collected. Note that there will be a different function p(w) for different races and different genders, using the same groupings used in the Hapmap project, since the probability of different alleles at particular SNPs is dependent on these groupings of race and gender. For the computation of $P(s_i)$, each allele on each chromosome will be associated with an estimated probability distribution, namely $p_{p,1,i}(w_{p,1,i})$, $p_{p,2,i}(w_{p,2,i})$, $p_{m,1,i}(w_{m,1,i})$ and $p_{m,2,i}(w_{m,2,i})$. One may then compute the maximum a-posteriori (MAP) estimate for $P(s_i)$ according to the MAP estimate for each of the individual distributions. For example, let $w_{p,1,i}^*$ be the argument that maximizes $p_{p,1,i}(w_{p,1,i})$. The MAP estimate of $P(s_i)$ may be found according to $$P(s_i)_{MAP} = w_{p,1,i}^* * w_{p,2,i}^* * w_{m,1,i}^* * w_{m,2,i}^* \qquad (9)$$

Since there is a probability distribution for each w, one can also compute conservative estimates of the values $P(s_i)$ to any specified confidence level, by integrating over the probability distribution, rather than simply using the MAP estimates. It is possible to do this, for example, to conservatively estimate P(M|A) to within some confidence level. Whether a conservative estimate or a MAP estimate is used, the estimate of $P(s_i)$ is continually refined for the computation of P(M|A). In what follows, reference to the assumed state will be eliminated to simplify the notation, and state $s_i$ is assumed for all explanations of detailed computation. Bear in mind that in actuality these calculations would be performed for each of 256 states and be summed over the probability of each.

The method of computing P(M|A) is now extended to multiple SNP loci, assuming that M represents the set of measurements of N pairs of SNPs on the embryo, M=[$M_1, \ldots, M_N$]. Assume also that A represents the set of hypotheses for each SNP about which parental chromosomes contributed to that SNP, A=[$A_1, \ldots, A_N$]. Let $S_{A'}$ represent the set of all other possible hypotheses that are different from A or are in the set A'. P(M|A) and P(M|A') may be computed:

$$P(M \mid A) = \prod_{i=1 \ldots N} P(M_i \mid A_i), \qquad (10)$$

$$P(M \mid A') = \sum_{A \in S_{A'}} P(A) \prod_{i=1 \ldots N} P(M_i \mid A_i)$$

Consider the computation of P(A). In essence, this is based on the likelihood of particular crossovers occurring in the formation of the gametes that form the embryo. The probability of a particular allele set depends on two factors, namely the probability that the embryonic chromosome comes from the mother or the father, and the probability of a particular combination of crossovers. For a normal set of embryonic chromosomes that do not suffer from aneuploidy, the a-priori probability that the embryonic chromosome comes from the mother or father is ~50% and is consequently common for all A. Now, consider the probability of a particular set of recombination nodes. The number of relevant recombination sites R depends on the number of measured SNPS: R=N−1. Since the DNA segment constituting N NSNPs around the PSNP of interest will be relatively short, crossover interference makes it highly improbable that two crossovers on the same chromosome can occur in one region. For reasons of computational efficiency this method assumes that only one crossover will occur in each region for each relevant chromosome, and this can occur at R possible sites. It will be obvious to someone skilled in the art how this method may be extended to include the possibility where there are multiple crossovers in a given region.

Let the probability of a crossover in each region between SNPs be denoted $P_r$, r=1 . . . N−1. To first order, the probability of a recombination node in a region r between two SNPs is proportional to the genetic distance between those SNPs (measured in cMorgans). However, much recent research has enabled a precise modeling of the probability of recombination between two SNP loci. Observations from sperm studies and patterns of genetic variation show that recombination rates vary extensively over kilobase scales and that much recombination occurs in recombination hotspots, and causes linkage disequilibrium to display a block-like structure. The NCBI data about recombination rates on the Human Genome is publicly available through the UCSC Genome Annotation Database.

Figure 2:
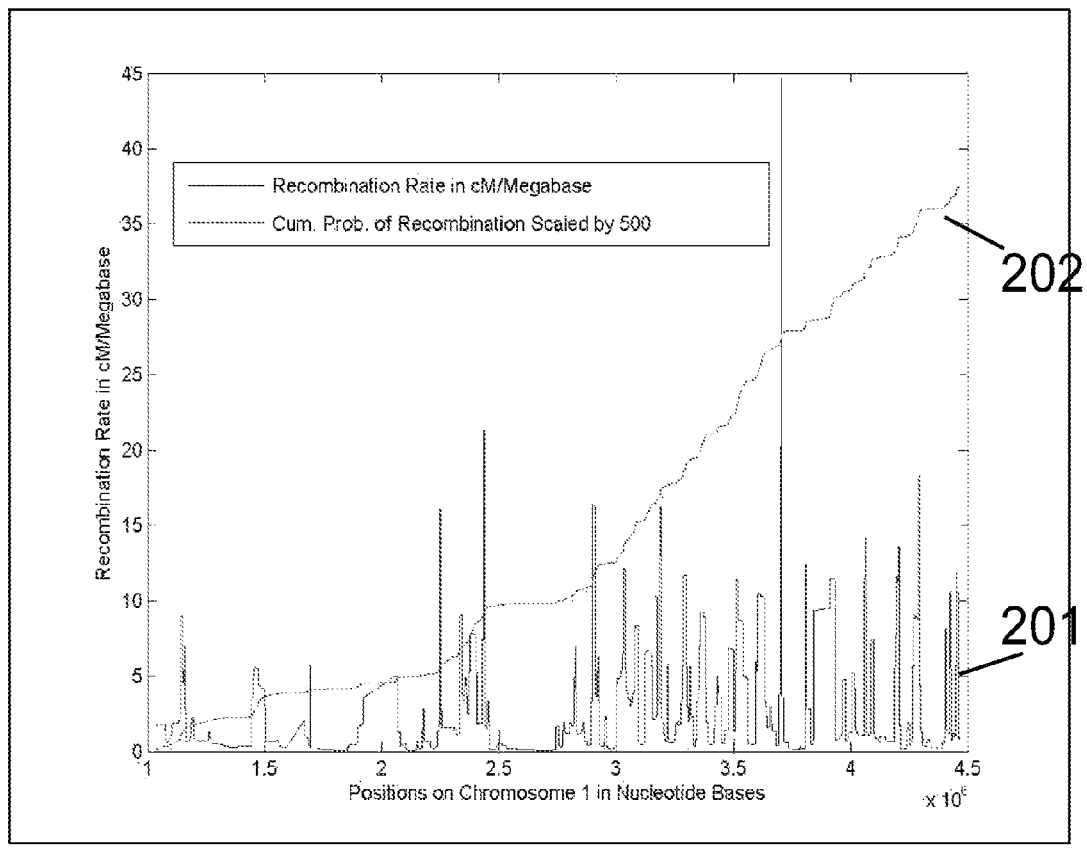
FIG. 2: an illustration of the variable rates of recombination along one region of Human Chromosome 1.

Various data sets can be used singly or in combination. Two of the most common data sets are from the Hapmap Project and from the Perlegen Human Haplotype Project. The latter is higher density; the former is higher quality. See FIG. 2 for the regional recombination rates from positions 1,038,423 to 4,467,775 of chromosome 1, based on the HapMap Phase I data, release 16a. These rates were estimated using the reversible-jump Markov Chain Monte Carlo (MCMC) method which is available in the package LDHat. The state-space considered is the distribution of piece-wise constant recombination rate maps. The Markov chain explores the distribution of the number and location of rate change-points, in addition to the rates for each segment, 201. These results may be used to generate an estimate of $P_r$ by integrating over the recombination rates times by the length of each constant segment between the SNPS. The cumulative recombination rate over the nucleotides 202 is shown in FIG. 2 in red.

Let C be a set of indicator variables $c_r$ such that $c_r=1$ if a crossover occurred in region r and 0 otherwise. $c_0=1$ if no crossovers occurred and 0 otherwise. Since it is assumed that only one crossover can occur in a region of N SNPs, only one element of the set C is non-zero. Hence, the probability of crossover represented by set C is found to be:

$$P_C = \left(1 - \sum_{r=1 \ldots N-1} P_r\right)^{C_0} \prod_{r=1} P_r^{C_r} \tag{11}$$

In the hypothesis A about SNPs 1 . . . N, there are four potential crossovers of relevance. Namely, the potential crossovers in i) the paternal chromosomes that formed the embryo (denoted by set $C_{pe}$ of indicator variables), ii) the paternal chromosomes that formed the sequenced sperm (set $C_{ps}$), iii) the maternal chromosomes that formed the embryo (set $C_{me}$) and iv) the maternal chromosomes that formed the sequenced egg (set $C_{ee}$). Two additional assumptions are v) whether the first paternal embryonic SNP comes from $p_{t,1,l}$ or $p_{t,2,l}$ and vi) whether the first maternal embryonic SNP comes from $m_{t,1,l}$ or $m_{t,2,l}$. Since the probabilities of crossovers between SNPs is found to differ between races and sexes, different crossover probabilities will be denoted as $P_{p,r}$ for the paternal chromosomes, and $P_{m,r}$ for the maternal chromosomes. Therefore, the probability of a particular hypothesis A, which subsumes the sets $C_{pe}$, $C_{ps}$, $C_{me}$, $C_{ee}$ is expressed as:

$$P(A) = \tag{12}$$

$$\frac{1}{4}\left(1 - \sum_{r=1 \ldots N-1} P_{p,r}\right)^{C_{pe,0}} \prod_{r=1 \ldots N-1} P_{p,r}^{C_{pe,r}} \left(1 - \sum_{r=1 \ldots N-1} P_{p,r}\right)^{C_{pe,0}}$$

$$\prod_{r=1 \ldots N-1} P_{p,r}^{C_{ps,r}} \left(1 - \sum_{r=1 \ldots N-1} P_{m,r}\right)^{C_{me,0}}$$

$$\prod_{r=1 \ldots N-1} P_{m,r}^{C_{me,r}} \left(1 - \sum_{r=1 \ldots N-1} P_{m,r}\right)^{C_{ee,0}} \prod_{r=1 \ldots N-1} P_{m,r}^{C_{ee,r}}$$

Now with the equations for determining P(A) and P(M/A), all the elements necessary to compute A* per Equation 3 above have been defined. Hence, it is possible to determine from the highly error-prone measurements of the embryonic SNPs where crossovers occurred, and to consequently clean the embryonic measurements with a high degree of confidence. It remains to determine the degree of confidence in the best hypothesis A*. To determine this, it is necessary to find the odds ratio $P(A^*|M)/P(A^{*\prime}|M)$. The tools have all been described above for this computation:

$$\frac{P(A^*|M)}{P(A^{*\prime}|M)} = \frac{P(A^*|M)}{1 - P(A^*|M)} = \tag{13}$$

$$\frac{P(A^*)P(M|A^*)}{P(A^{*\prime})P(M|A^{*\prime})} = \frac{P(A^*)P(M|A^*)}{(1 - P(A^*))P(M|A^{*\prime})} = OR_{A^*}$$

The confidence in A* is then given as $P(A^*|M)=OR_{A^*}/(1+OR_{A^*})$. This computation indicates the confidence in a particular hypothesis A*, but it does not indicate a confidence in a particular determination of a SNP. In order to compute the confidence in a determination of embryonic PSNP n, it is necessary to create the set of all hypotheses A that don't change the value of this SNP. This set will be denoted as $S_{A^*,n}$, which corresponds to all hypothesis that result in PSNP n on the embryo having the same value as is predicted by hypothesis A*. Similarly, create a set $S_{A^{*\prime},n}$ which corresponds to all hypothesis that result in PSNP n having a different value to that predicted by hypothesis A*. Now, it is possible to compute the odds ratio of the probability that the SNP is correctly called versus the probability that the SNP is incorrectly called:

$$OR_{A^*,n} = \tag{14}$$

$$\frac{\sum_{A \in S_{A^*,n}} P(A|M)}{\sum_{A \in S_{A^{*\prime},n}} P(A|M)} = \frac{\sum_{A \in S_{A^*,n}} P(A|M)}{1 - \sum_{A \in S_{A^*,n}} P(A|M)} = \frac{\sum_{A \in S_{A^*,n}} P(A)P(M|A)}{\sum_{A \in S_{A^{*\prime},n}} P(A)P(M|A)}$$

The confidence in the particular call of embryonic SNP n based on the odds ratio $OR_{A^*,n}$ can be computed as:

$$P(\text{correctly called SNP } n) = \sum_{A \in S_{A^*,n}} P(A|M) = \frac{OR_{A^*,n}}{1 + OR_{A^*,n}} \tag{15}$$

Note that this technique could also be used to detect such defects as uniparental disomy (UPD) wherein two of the same chromosomes are from the same parent, while none of that chromosomes from the other parent is present. Upon attempting to deduce the crossovers in the parent chromosomes, there will be no hypothesis which adequately explains the data with a high confidence, and if alternate hypotheses are allowed that include the possibility of UPD, they will found to be more likely.

Bounding the Effect of Uncertainty in Recombination Rates and SNP Measurement Reliability The disclosed method depends on: assumptions about the probability of recombination between particular SNPs; assumptions about the probability of the correct measurement of each SNP on the embryonic, sperm, egg, paternal and maternal chromosomes; and assumptions about the likelihood of certain alleles within different population groups. Consider each of these assumptions: the mechanism of recombination is not perfectly understood and modeled, and the crossover probability has been established to vary based on an individual's genotype. Furthermore, the techniques by which the recombination rates are measured show substantial variability. For example, the package LDHat, which implements the reversible-jump Markov Chain Monte Carlo (MCMC) method, makes a set of assumptions and requires a set of user inputs about the mechanism and characterization of recombination. These assumptions can affect predicted recombination rates between SNPs as is evinced by the different results obtained by various studies.

It is anticipated that the assumptions about recombination rates, out of all assumptions listed above, will have the most impact on Equation 15. The computations described above should be based on the best estimates of the probability for crossover between SNPS, Pr. Thereafter, conservative estimates may be used for $P_r$ using values at, for example, the 95% confidence bounds for the recombination rates, in the direction that reduces the confidence measure P(correctly called SNP n). The 95% confidence bounds may be derived from confidence data produced by various studies of recombination rates, and this may be corroborated by looking at the level of discordance between published data from different groups using different methods.

Similarly, the 95% confidence bounds may be used for the estimates of the probability that each SNP is correctly called: $p_p$, $p_m$, $p_e$. These numbers can be computed based on the actual measured array intensities included in the genotyping assay output files, combined with empirical data on the reliability of the measurement technique. Note that those NSNPs for which these parameters $p_p$, $p_m$ and $p_e$ are not well established may be ignored. For example, since the diploid parental data is reliably measured, one may ignore NSNP measurements of the parents' haploid cells and on the embryo that do not correspond to any of the alleles on the relevant SNPs of the parent's diploid tissue.

Lastly, consider the assumptions about the likelihood of certain alleles within different population groups, which give rise to the computation $P(s_i)$. These assumptions also will not have a large impact on the disclosed method since the measurement of the parental diploid data is reliable i.e. direct measurement of the state $s_i$ from the parental samples typically result in data with high confidence. Nonetheless, it is possible to use the probability distribution for each as described in Equation 8 in order to compute a confidence bound for the probability of each state $P(s_i)$. As above, one may compute the 95% confidence bound for each $P(s_i)$ in the conservative direction that reduces confidence measure P(correctly called SNP n).

The determination of P(correctly called SNP n) will inform the decision about how many NSNPs need to be measured around each PSNP in order to achieve the desired level of confidence.

Note that there are different approaches to implementing the concept of the disclosed method, namely combining the measurement of the parent's DNA, the measurement of the DNA of one or more embryos, and the a-priori knowledge of the process of meiosis, in order to obtain a better estimate of the embryonic SNPs. It will be clear to one skilled in the art, how similar methods can be applied when different subsets of the a-priori knowledge are known or not known, or known to a greater or lesser degree of certainty. For example, one can use the measurements of multiple embryos to improve the certainty with which one can call the SNPs of a particular embryo or to accommodate missing data from the parents. Note also that one does not need a PSNP of interest to be measured by the measurement technique. Even if that PSNPs is not determined by the measurement system, it can still be reconstructed with a high degree of confidence by the disclosed method.

Also note that once the points of crossover that occurred during meiosis have been determined, and the regions of the target genome have been mapped to the pertinent regions of the parental DNA, it is possible to infer not only the identity of individual SNPs of interest, but also whole regions of DNA that may be missing in the measured target genome due to allele drop-out or other errors in measurement. It is also possible to measure insertions and deletions in the parental DNA, and use the disclosed method to infer that they exist in the target DNA.

Various techniques may be used to improve the computational complexity of the disclosed algorithm described above. For example, one may only or predominantly select those NSNPs that differ between the mother and the father. Another consideration would be to only use NSNPs that are spaced nearby the PSNPs to minimize the chance of crossovers occurring between the NSNPs and PSNPs of interest. One could also use NSNPs that were spaced along the chromosome so as to maximize coverage of multiple PSNPs. Another consideration will be to initially use only a small number of NSNPs to determine roughly where crossovers occurred, and with only a limited degree of certainty. Additional NSNPs can then be used to refine the crossover model and increase the probability of correctly calling the PSNPs. The number of crossover combinations to consider scales roughly as $N^C$ where N is the number of SNPs and C is the maximum number of crossovers. Consequently, for C=4 it is possible to accommodate roughly N=100 for each PSNP while remaining computationally tractable on a Pentium-IV processor. Using the approaches described above and other approaches for increased computational efficiency, N>100, C>4 can be easily accommodated. One such approach is described below.

Note that there are many other approaches to make a call on a PSNP and generate an estimate of the probability that a PSNPs has been correctly determined, based on a particular set of embryonic data, parent data, and algorithm used, without changing the underlying concept. This probability can be used for individual decision-making, and for implementing a reliable service in the context of IVF or NIPGD.

Recursive Solution to the Genetic Data Cleaning Algorithm

Another embodiment of the invention involving an algorithm that scales linearly is described here. Given the limited nature of computation power, the length of the computation may be a significant factor in the use of the disclosed method. When running computations, any algorithm that must compute certain values where the number of computations needed rises exponentially with the number of SNPs can become unwieldy. A solution that involves a number of calculations that increase linearly with the number of SNPs will always be preferred from a time standpoint as the number of SNPs gets large. Below this approach is described.

A simple approach, which is to consider all possible hypotheses must contend with the running time being an exponential function in number of SNPs. Suppose, as before, that measured data are a collection of measured embryo, father and mother chromosome measurements on k SNPs, i.e. $M=\{M_1, \ldots, M_k\}$ where $M_i=(e_{1i},e_{2i},p_{1i},p_{2i},m_{1i},m_{2i})$. As before, the hypotheses space is $S_H=(H^1, \ldots, H^q)=\{$set of all the hypotheses$\}$, where each hypothesis is of the format $H^i=(H^i_1, \ldots H^i_k)$ where $H^i_j$ is the "mini" hypothesis for snip i, of the format $H^i_j=(p_i^*,m_i^*)$ where $p_i^* \in \{p_{1i}, p_{2i}\}$ and $m_i^* \in \{m_{1i},m_{2i}\}$. There are 4 different "mini" hypotheses $H^i_j$, in particular:

$H^i_j1:(e_{1i},e_{2i})=\{(p_{1i},m_{1i})$ or $(m_{1i},p_{1i})\}$; $H^i_j2:(e_{1i},e_{2i})=\{(p_{1i},m_{2i})$ or $(m_{2i},p_{1i})\}$ $H^i_j3:(e_{1i},e_{2i})=\{(p_{2i},m_{1i})$ or $(m_{1i},p_{2i})\}$; $H^i_j4:(e_{1i},e_{2i})=\{(p_{2i},m_{2i})$ or $(m_{2i},p_{2i})\}$

The goal is to choose the most likely hypothesis H* as:
$H^*=\text{argmax}_{H \in S_H} P(H|M)=\text{arg max}_{H \in S_H} F(M,H)$ where function $F(M,H)=P(H|M)$ There are $4^k$ different hypotheses in the space $S^H$. By trying to find the best hypothesis by exhaustively exploring the entire space $S^H$, the necessary algorithm would be of exponential order in k O(exp(k)), where k is the number of SNPs involved. For large k, even k>5, this is immensely slow and unpractical. Therefore, it is more practical to resort to a recursive solution which solves the problem of size k as a function of the problem of size (k−1) in constant time. The solution shown here is of the linear order in k, O(k).

Recursive Solution Linear in the Number of SNPs

Begin with F(M,H)=P(H|M)=P(M|H)*P(H)/P(M). Then argmax$_H$F(M,H)=argmax$_H$P(M|H)*P(H) and the goal is to solve P(M|H)*P(H) in linear time. Suppose that $M_{(s,k)}$= measurement on SNPs s to k, $H_{(s,k)}$=hypothesis on SNPs s to k, and to simplify notation $M_{(k,k)}=M_k$, $H_{(k,k)}=H_k$= measurement and hypothesis on SNP k. As shown before:

$$P(M_{(1,k)} \mid H_{(1,k)}) = \prod_{i=1}^{k} P(M_i \mid H_i) =$$

$$P(M_k \mid H_k) * \prod_{i=1}^{k-1} P(M_i \mid H_i) = P(M_k \mid H_k) * P(M_{(1,k-1)} \mid H_{(1,k-1)})$$

Also:

$$P(H_{(1,k)}) = 1/4 * \prod_{i=2}^{k} PF(H_{i-1}, H_i) =$$

$$PF(H_{k-1}, H_k) * 1/4 * \prod_{i=2}^{k-1} PF(H_{i-1}, H_i) = PF(H_{k-1}, H_k) * P(H_{(1,k-1)})$$

where $PF(H_{i-1}, H_i) = \begin{cases} 1 - PC(H_{i-1}, H_i) & H_{i-1} = H_i \\ PC(H_{i-1}, H_i) & H_{i-1} \neq H_i \end{cases}$ and $PC(H_{i-1}, H_i)$=probability of crossover between $H_{i-1}$, $H_i$ Finally, for k SNPs:

F(M,H)=P(M|H)*P(H)=P($M_{(1,k)}$|$H_{(1,k)}$)*P($H_{(1,k)}$)=P($M_{(1,k-1)}$|$H_{(1,k-1)}$)*P($H_{(1,k-1)}$)*P($M_k$|$H_k$)*PF($H_{k-1}$, $H_k$)

so in short F(M,H)=F($M_{(1,k)}$,$H_{(1,k)}$))=F($M_{(1,k-1)}$,$H_{(1,k-1)}$)*P($M_k$|$H_k$)*PF($H_{k-1}$, $H_k$)

i.e. we can reduce the calculation of F on k SNPs to the calculation of F on k−1 SNPs.

For H=($H_1$, . . . $H_k$), the hypothesis on k SNPs:

$$\max_H F(M, H) = \max_{(H_{(1,k-1)}, H_k)} F(M, (H_{(1,k-1)}, H_k))$$

$$= \max_{H_k} \max_{H_{(1,k-1)}} F(M, (H_{(1,k-1)}, H_k))$$

$$= \max_{H_k} G(M_{(1,k)}, H_k)$$

where $$G(M_{(1,n)}, H_n) = \max_{H_{(1,n-1)}} F(M_{(1,n)}, (H_{(1,n-1)}, H_n))$$

$$= \max_{H_{(1,n-1)}} F(M_{(1,n-1)}, H_{(1,n-1)}) * P(M_n \mid H_n) * PF(H_{n-1}, H_n)$$

$$= P(M_n \mid H_n) * \max_{H_{(1,n-1)}} F(M_{(1,n-1)}, H_{(1,n-1)}) * PF(H_{n-1}, H_n)$$

$$= P(M_n \mid H_n) * \max_{H_{n-1}} \max_{H_{(1,n-2)}} F(M_{(1,n-1)}, (H_{(1,n-2)}, H_{n-1})) * PF(H_{n-1}, H_n)$$

$$= P(M_n \mid H_n) * \max_{H_{n-1}} PF(H_{n-1}, H_n) * G(M_{(1,n-1)}, H_{n-1})$$

To summarize this:

$$\max_H F(M, H) = \max_{H_n} G(M_{(1,k)}, H_k)$$

where G can be found recursively: for n=2, . . . , k $$G(M_{(1,n)}, H_n) = P(M_n \mid H_n) * \max_{H_{n-1}} \lfloor PF(H_{n-1}, H_n) * G(M_{(1,n-1)}, H_{n-1}) \rfloor$$

and $G(M_{(1,1)}, H_1) = 0.25 * P(M_1 \mid H_1)$

The algorithm is as follows:

For n=1: Generate 4 hypotheses $H^1 i$, calculate $G(M_1|H_1 i)$ for i=1, . . . , 4.

For n=2: Generate 4 hypothesis for $H_2 i$, calculate $G(M_{(1,2)}|H_{2i})$, i=1, . . . , 4 in constant time using the formula:

$$G(M_{(1,2)}, H_2 i) = P(M_2 \mid H_2 i) * \max_{j=1,\ldots,4} [PF(H_1, H_2 i) * G(M_1, H_1 j)]$$

For n = k: Generate 4 hypothesis for $H_k i$, make $G(M_{(1,k)} \mid H_k i), i = 1, \ldots, 4$ by $G(M_{(1,k)}, H_k i) =$ $$P(M_k \mid H_k i) * \max_{j=1,\ldots,4} \lfloor PF(H_{k-1}, H_k i) * G(M_{(1,k-1)}, H_{k-1} j) \rfloor$$

At any time there are only 4 hypotheses to remember and a constant number of operations. So the algorithm is linear in k, number of SNPs, as opposed to exponential.

Solving P(M) in Linear Time

It is not necessary to solve for P(M) to get the best hypothesis, since it is constant for all H. But in order to get the actual, meaningful number for the conditional probability P(H|M)=P(M|H)*P(H)/P(M), it is also necessary to derive P(M). As above, we can write:

$$P(M) = P(M_{(1,k)})$$

$$= \sum_{H_{(1,k)}} P(M_{(1,k)} \mid H_{(1,k)}) * P(H_{(1,k)})$$

$$= \sum_{H_k} P(M_k \mid H_k) \sum_{H_{(1,k-1)}} P(M_{(1,k-1)} \mid H_{(1,k-1)}) * P(H_{(1,k-1)}) * PF(H_{k-1}, H_k)$$

$$= \sum_{H_k} P(M_k \mid H_k) * W(M_{(1,k-1)} \mid H_k)$$

where $$W(M_{(1,k-1)} \mid H_k) = \sum_{H_{(1,k-1)}} P(M_{(1,k-1)} \mid H_{(1,k-1)}) * P(H_{(1,k-1)}) * PF(H_{k-1}, H_k)$$

We can solve for W(M,H) by recursion:

$$W(M_{(1,k-1)} \mid H_k) = \sum_{H_{(1,k-1)}} P(M_{(1,k-1)} \mid H_{(1,k-1)}) * P(H_{(1,k-1)}) * PF(H_{k-1}, H_k)$$

$$= \sum_{H_{k-1}} P(M_{k-1} \mid H_{k-1}) \sum_{H_{(1,k-2)}} P(M_{(1,k-2)} \mid H_{(1,k-2)}) *$$

-continued $$= \sum_{H_{k-1}} P(M_{k-1} \mid H_{k-1}) * PF(H_{k-1}, H_k) * W(M_{(1,k-2)} \mid H_{k-1})$$

so in short, problem of size k is reduced to the problem of size (k−1) by $$W(M_{(1,k-1)} \mid H_k) =$$
$$\sum_{H_{k-1}} P(M_{k-1} \mid H_{k-1}) * PF(H_{k-1}, H_k) * W(M_{(1,k-2)} \mid H_{k-1})$$

and $W(M_{(1,1)} \mid H_2) = \sum_{H_1} P(M_1 \mid H_1) * 0.25 * PF(H_1, H_2)$

As before, for n=2:k, generate W(2), . . . , W(K)= $W(M_{(1,k-1)} \mid H_k)$ recursively, until finally, it is possible to derive $$P(M) = \sum_{H_k} P(M_k \mid H_k) * W(M_{(1,k-1)} \mid H_k).$$

At each level there are only four different hypotheses I-k, so the algorithm is again linear in the number of SNPs k.

Individual SNP Confidence in Linear Time

Once the best hypothesis $H^* = (H_1^*, \ldots, H_k^*)$, has been computed, it now may be desired to derive the confidence in the final answer for each SNP, namely $P(H_i^* \mid M)$, for i=1, . . . , k. As before $P(H_i^* \mid M) = P(M \mid H_i^*)P(H_i^*)/P(M) = W(H_i^*, M)/P(M)$, where P(M) is already known.

$$W(M, H_i^*) = \sum_{H, H_i = H_i^*} P(M \mid H) * P(H)$$
$$= \sum_{H = (H_{(1,i-1)}, H_i^*, H_{(i+1,k)})} P(M \mid H) * P(H),$$

i.e. hypothesis H has been broken up to the hypothesis on first i−1 SNPs, ith SNP, and hypothesis on the i+1 to kth SNP. As before:

$$P(M_{(1,k)} \mid H_{(1,k)}) = \prod_{j=1}^{k} P(M_j \mid H_j)$$
$$= \prod_{j=1}^{i-1} P(M_j \mid H_j) * P(M_i \mid H_i^*) * \prod_{j=i+1}^{k} P(M_j \mid H_j)$$
$$= P(H_{(1,i-1)} \mid H_{(1,i-1)}) * P(M_i \mid H_i^*) * P(M_{(i+1,k)} \mid H_{(i+1,k)})$$

and $$P(H_{(1,k)}) = 1/4 * \prod_{j=2}^{k} PF(H_{j-1}, H_j)$$
$$= 1/4 * \prod_{j=2}^{i-1} PF(H_{j-1}, H_j) * PF(H_{i-1}, H_i^*) * PF(H_{i-1}, H_i^*) *$$
$$\prod_{j=i+2}^{k} PF(H_{j-1}, H_j)$$
$$= 1/4 * T(H_{(1,i-1)}) * PF(H_{i-1}, H_i^*) * PF(H_{i-1}, H_i^*) * T(H_{(i+1,k)})$$

So $P(H_{(1,k)}) = 1/4 * T(H_{(1,k)}) = 1/4 * T(H_{(1,i-1)}) * PF(H_{i-1}, H_i^*) * PF(H_{i-1}, H_i^*) * T(H_{(i+1,k)})$ where $$T(H_{(1,k)}) = \prod_{j=2}^{k} PF(H_{j-1}, H_j).$$

From this it is possible to show that $$W(M_{(1,k)}, H_i^*) = \sum_{H, H_i = H_i^*} P(M \mid H) * P(H)$$
$$= \sum_{H, H_i = H_i^*} P(M \mid H) * 1/4 * T(H)$$

$P(M_{(1,i-1)} \mid H_{(1,i-1)}) * P(M_i \mid H_i^*) * P(M_{(i+1,k)} \mid H_{(i+1,k)}) *=$
$$\sum_{H = (H_{(1,i-1)}, H_i^*, H_{(i+1,k)})} 1/4 * T(H_{(1,i-1)}) * PF(H_{i-1}, H_i^*) *$$
$$PF(H_{i-1}, H_i^*) * T(H_{(i+1,k)}) = 4 * P(M_i \mid H_i^*) *$$
$$\left( \sum_{H_{i-1}} P(M_{(1,i-1)} \mid H_{(1,i-1)}) * 1/4 * T(H_{(1,i-1)}) * PF(H_{i-1}, H_i^*) \right) *$$
$$\left( \sum_{H_{i+1}} P(M_{(i+1,k)} \mid H_{(i+1,k)}) * 1/4 * T(H_{(i+1,k)}) * PF(H_i^*, H_{i+1}) \right) =$$
$$4 * P(M_i \mid H_i^*) * \left( \sum_{H_{i-1}} W(M_{(1,i-1)}, H_{i-1}) * PF(H_{i-1}, H_i^*) \right) *$$
$$\left( \sum_{H_{i+1}} W(M_{(i+,k)}, H_{i+1}) * PF(H_i^*, H_{i+1}) \right)$$

Again a case of size k has been reduced to two pieces of smaller size, albeit a bit more complicated than before. Each of the pieces can be calculated as $$W(M_{(1,n)}, H_n) = P(M_n \mid H_n) * \left( \sum_{H_{n-1}} W(M_{(1,n-1)}, H_{n-1}) * PF(H_{n-1}, H_n) \right)$$
$$W(M_{(m,k)}, H_m) = P(M_m \mid H_m) * \left( \sum_{H_{m+1}} W(M_{(m+1,k)}, H_{m+1}) * PF(H_m, H_{m+1}) \right)$$

So the algorithm will, for n=1, . . . , k, m=k, . . . 1, for each of 4 different $H_n$, $H_m$ calculate $W(M(H_{(1,n)}, H_n)$, $W(M_{(m,k)}, H_m)$ and then combine them as needed to calculate $W(M_{(1,k)}, H_i^*)$, for i=1, . . . , k. The number of operations is still linear in k.

Application of the Disclosed Method to Embryonic Data when a Smaller or Different Set of Data is Available In one embodiment of the system it is only necessary to make use of diploid data from one parent (presumably the mother), with or without haploid data from either or both of the parents, and when that data is known to a greater or lesser degree of certainty. For example it is expected that, given the grueling nature of egg donation, there will be occasions when maternal haploid data is not readily available. It will be clear to one skilled in the art, after reading this description, how the statistical methods for computing the likelihood of a particular SNP can be modified given a limited data set.

An alternative approach uses data from more distant relatives to make up for missing diploid or haploid data of one or both parents. For example, since it is known that one set of an individual's chromosomes come from each of his or her parents, diploid data from the maternal grandparents could be used to partially reconstruct missing or poorly measured maternal haploid data.

Note the recursive nature of this method: given the naturally noisy measurement of single cell parental haploid data, along with the diploid and/or haploid data of the appropriate grandparents, the disclosed method could be used to clean the parental haploid data, which in turn will provide more accurate genotyping of the embryo. It should be obvious to one skilled in the arts how to modify the method for use in these cases.

It is preferable to use more information rather than less, as this can increase the chances of making the right call at a given SNP, and can increase the confidence in those calls. This must be balanced with the increasing complexity of the system as additional techniques and sources of data are used. There are many sources of additional information, as well as techniques available to use the information to augment the data. For example, there are informatics based approaches which take advantage of correlations which can be found in Hapmap data, or other repositories of genomic data. In addition there are biological approaches which can allow for the direct measurement of genetic data that otherwise would need to be recreated in silico. For example, haploid data otherwise unavailable may be measureable by extracting individual chromosomes from diploid cells using flow cytometry techniques to isolate fluorescently tagged chromosomes. Alternately, one may use cell fusion to create monoallelic hybrid cells to effect diploid to haploid conversion.

Application of the Disclosed Method to Selecting which Embryo is Likely to Implant In one embodiment, the system can be used to determine the likelihood of an embryo to implant in the mother and develop into a baby. To the extent that the likelihood of the embryo implanting is determined by SNPs of the embryo, and/or their relation to SNPs of the mother, the disclosed method will be important in helping the selection of embryos, based on making a reliable prediction of which will successfully implant based on the clean SNP data. To best predict the likelihood it will be necessary to take into account the determined genotype of the embryo possibly combined with the levels of gene expression in the embryo, the levels of gene expression in the mother, and/or the determined genotype of the mother.

In addition, it is well known that aneuploid embryos are less likely to implant, less likely to result in a successful pregnancy, and less likely to result in a healthy child. Consequently, screening for aneuploides is an important facet to selecting the embryo that is most likely to result in a successful outcome. More detail on this approach is given below.

Deducing Parental Haploid Data

In one embodiment of the method, it may be necessary to deduce parental haplotypes, given detailed knowledge of the diploid data of a parent. There are multiple ways this can be done. In the simplest case, haplotypes have already been inferred by molecular assay of single haploid cells of a direct relation (mother, father, son or daughter). In this case, it is a trivial matter to one skilled in the art to deduce the sister haplotype by subtracting the known haplotype from the diploid genotype measured by molecular assay. For example, if a particular locus is heterozygous, an unknown parental haplotype is the opposite allele from the known parental haplotype.

In another case, the noisy haploid data of the parent may be known from molecular biological haplotyping of individual parental haploid cells, such as a sperm cell, or from individual chromosomes, which may be isolated by various methods including magnetic beads and flow cytometry. In this case, the same procedure can be used as above, except that the determined haplotype will be as noisy as the measured haplotype.

There are also methods for deducing haploid data sets directly from diploid data, using statistical methods that utilize known haplotype blocks in the general population (such as those created for the public Hapmap project). A haplotype block is essentially a series of correlated alleles that occur repeatedly in a variety of populations. Since these haplotype blocks are often ancient and common, they may be used to predict haplotypes from diploid genotypes. The parents' inferred haplotype blocks can then be used as input for the method described herein to clean the noisy data from the embryos. Publicly available algorithms that would accomplish this task include an imperfect phylogeny approach, Bayesian approaches based on conjugate priors, and priors from population genetics. Some of these algorithms use hidden Markov models. One study used public trio and unrelated individual data to demonstrate that these algorithms perform with error rates as low as 0.05% across 1 MB of sequence. However, as expected, accuracy is lower for individuals with rare haplotype blocks. In one estimate, computational methods failed to phase as many as 5.1% of loci with minor allele frequency of 20%.

In one embodiment of the invention, genetic data from multiple blastomeres taken from different embryos during an IVF cycle is used to infer the haplotype blocks of the parents with greater reliability.

Techniques for Screening for Aneuploidy Using High and Medium Throughput Genotyping In one embodiment of the system the measured genetic data can be used to detect for the presence of aneuploides and/or mosaicism in an individual. Disclosed herein are several methods of using medium or high-throughput genotyping to detect the number of chromosomes or DNA segment copy number from amplified or unamplified DNA from tissue samples. The goal is to estimate the reliability that can be achieved in detecting certain types of aneuploidy and levels of mosaicism using different quantitative and/or qualitative genotyping platforms such as ABI TAQMAN, MIPS, or Microarrays from ILLUMINA, AGILENT and AFFMETRIX. In many of these cases, the genetic material is amplified by PCR before hybridization to probes on the genotyping array to detect the presence of particular alleles. How these assays are used for genotyping is described elsewhere in this disclosure.

Described below are several methods for screening for abnormal numbers of DNA segments, whether arising from deletions, aneuploides and/or mosaicism. The methods are grouped as follows: (i) quantitative techniques without making allele calls; (ii) qualitative techniques that leverage allele calls; (iii) quantitative techniques that leverage allele calls; (iv) techniques that use a probability distribution function for the amplification of genetic data at each locus. All methods involve the measurement of multiple loci on a given segment of a given chromosome to determine the number of instances of the given segment in the genome of the target individual. In addition, the methods involve creating a set of one or more hypotheses about the number of instances of the given segment; measuring the amount of genetic data at multiple loci on the given segment; determining the relative probability of each of the hypotheses given the measurements of the target individual's genetic data; and using the relative probabilities associated with each hypothesis to determine the number of instances of the given segment. Furthermore, the methods all involve creating a combined measurement M that is a computed function of the measurements of the amounts of genetic data at multiple loci. In all the methods, thresholds are determined for the selection of each hypothesis $H_i$ based on the measurement M, and the number of loci to be measured is estimated, in order to have a particular level of false detections of each of the hypotheses.

The probability of each hypothesis given the measurement M is $P(H_i|M)=P(M|H_i)P(H_i)/P(M)$. Since $P(M)$ is independent of $H_i$, we can determine the relative probability of the hypothesis given M by considering only $P(M|H_i)P(H_i)$. In what follows, in order to simplify the analysis and the comparison of different techniques, we assume that $P(H_i)$ is the same for all $\{H_i\}$, so that we can compute the relative probability of all the $P(H_i|M)$ by considering only $P(M|H_i)$. Consequently, our determination of thresholds and the number of loci to be measured is based on having particular probabilities of selecting false hypotheses under the assumption that $P(H_i)$ is the same for all $\{H_i\}$. It will be clear to one skilled in the art after reading this disclosure how the approach would be modified to accommodate the fact that $P(H_i)$ varies for different hypotheses in the set $\{H_i\}$. In some embodiments, the thresholds are set so that hypothesis H is is selected which maximizes $P(H_i|M)$ over all i. However, thresholds need not necessarily be set to maximize $P(H_i|M)$, but rather to achieve a particular ratio of the probability of false detections between the different hypotheses in the set $\{H_i\}$.

It is important to note that the techniques referred to herein for detecting aneuploides can be equally well used to detect for uniparental disomy, unbalanced translocations, and for the sexing of the chromosome (male or female; XY or XX). All of the concepts concern detecting the identity and number of chromosomes (or segments of chromosomes) present in a given sample, and thus are all addressed by the methods described in this document. It should be obvious to one skilled in the art how to extend any of the methods described herein to detect for any of these abnormalities.

The Concept of Matched Filtering

The methods applied here are similar to those applied in optimal detection of digital signals. It can be shown using the Schwartz inequality that the optimal approach to maximizing Signal to Noise Ratio (SNR) in the presence of normally distributed noise is to build an idealized matching signal, or matched filter, corresponding to each of the possible noise-free signals, and to correlate this matched signal with the received noisy signal. This approach requires that the set of possible signals are known as well as the statistical distribution—mean and Standard Deviation (SD)—of the noise. Herein is described the general approach to detecting whether chromosomes, or segments of DNA, are present or absent in a sample. No differentiation will be made between looking for whole chromosomes or looking for chromosome segments that have been inserted or deleted. Both will be referred to as DNA segments. It should be clear after reading this description how the techniques may be extended to many scenarios of aneuploidy and sex determination, or detecting insertions and deletions in the chromosomes of embryos, fetuses or born children. This approach can be applied to a wide range of quantitative and qualitative genotyping platforms including TAQMAN, qPCR, ILLUMINA Arrays, AFFMETRIX Arrays, AGILENT Arrays, the MIPS kit etc.

Formulation of the General Problem

Assume that there are probes at SNPs where two allelic variations occur, x and y. At each locus i, i=1 ... N, data is collected corresponding to the amount of genetic material from the two alleles. In the TAQMAN assay, these measures would be, for example, the cycle time, $C_t$, at which the level of each allele-specific dye crosses a threshold. It will be clear how this approach can be extended to different measurements of the amount of genetic material at each locus or corresponding to each allele at a locus. Quantitative measurements of the amount of genetic material may be non-linear, in which case the change in the measurement of a particular locus caused by the presence of the segment of interest will depend on how many other copies of that locus exist in the sample from other DNA segments. In some cases, a technique may require linear measurements, such that the change in the measurement of a particular locus caused by the presence of the segment of interest will not depend on how many other copies of that locus exist in the sample from other DNA segments. An approach is described for how the measurements from the TAQMAN or qPCR assays may be linearized, but there are many other techniques for linearizing nonlinear measurements that may be applied for different assays.

The measurements of the amount of genetic material of allele x at loci 1 ... N is given by data $d_x=[d_{x1} \ldots d_{xN}]$. Similarly for allele y, $d_y=[d_{y1} \ldots d_{yN}]$. Assume that each segment j has alleles $a_j=[a_{j1} \ldots a_{jN}]$ where each element $a_{j1}$ is either x or y. Describe the measurement data of the amount of genetic material of allele x as $d_x=s_x+\upsilon_x$ where $s_x$ is the signal and $\upsilon_x$ is a disturbance. The signal $s_x=[f_x(a_{11}, \ldots, a_{J1}) \ldots f_x(a_{jN}, \ldots, a_{JN})]$ where $f_x$ is the mapping from the set of alleles to the measurement, and J is the number of DNA segment copies. The disturbance vector $\upsilon_x$ is caused by measurement error and, in the case of nonlinear measurements, the presence of other genetic material besides the DNA segment of interest. Assume that measurement errors are normally distributed and that they are large relative to disturbances caused by nonlinearity (see section on linearizing measurements) so that $\upsilon_{xi}=n_{xi}$ where $n_{xi}$ has variance $\sigma_{xi}^2$ and vector $n_x$ is normally distributed ~N(0,R), R=E$(n_x n_x^T)$. Now, assume some filter h is applied to this data to perform the measurement $m_x=h^T d_x=h^T s_x+h^T \upsilon_x$. In order to maximize the ratio of signal to noise $(h^T s_x/h^T n_x)$ it can be shown that h is given by the matched filter $h=\mu R^{-1}s_x$ where $\mu$ is a scaling constant. The discussion for allele x can be repeated for allele y.

Method 1a: Measuring Aneuploidy or Sex by Quantitative Techniques that do not Make Allele Calls when the Mean and Standard Deviation for Each Locus is Known Assume for this section that the data relates to the amount of genetic material at a locus irrespective of allele value (e.g. using qPCR), or the data is only for alleles that have 100% penetrance in the population, or that data is combined on multiple alleles at each locus (see section on linearizing measurements)) to measure the amount of genetic material at that locus. Consequently, in this section one may refer to data $d_x$ and ignore $d_y$. Assume also that there are two hypotheses: $h_0$ that there are two copies of the DNA segment (these are typically not identical copies), and $h_1$ that there is only 1 copy. For each hypothesis, the data may be described as $d_{xi}(h_0)=s_{xi}(h_0)+n_{xi}$ and $d_{xi}(h_1)=s_{xi}(h_1)+n_{xi}$ respectively, where $s_{xi}(h_0)$ is the expected measurement of the genetic material at locus i (the expected signal) when two DNA segments are present and $s_{xi}(h_1)$ is the expected data for one segment. Construct the measurement for each locus by differencing out the expected signal for hypothesis $h_0$: $m_{xi}=d_{xi}-s_{xi}(h_0)$. If $h_1$ is true, then the expected value of the measurement is $E(m_{xi})=s_{xi}(h_1)-s_{xi}(h_0)$. Using the matched filter concept discussed above, set $h=(1/N)R^{-1}(s_{xi}(h_1)-s_{xi}(h_0))$. The measurement is described as $m=h^T d_x=(1/N)\Sigma_{i=1\ldots N}((s_{xi}(h_1)-s_{xi}(h_0))/\sigma_{xi}^2)m_{xi}$.

If $h_1$ is true, the expected value of $E(m|h_1)=m_1=(1/N)\Sigma_{i=1\ldots N}(s_{xi}(h_1)-s_{xi}(h_0))^2/\sigma_{xi}^2$ and the standard deviation of m is $\sigma_{m|h1}^2=(1/N^2)\Sigma_{i=1\ldots N}(s_{xi}(h_1)-s_{xi}(h_0))^2/\sigma_{xi}^4)\sigma_{xi}^2=(1/N^2)\Sigma_{i=1\ldots N}(s_{xi}(h_1)-s_{xi}(h_0))^2/\sigma_{xi}^2$.

If $h_0$ is true, the expected value of m is $E(m|h_0)=m_0=0$ and the standard deviation of m is again $\sigma_{m|h0}^2=(1/N^2)\Sigma_{i=1\ldots N}(s_{xi}(h_1)-s_{xi}(h_0))^2/\sigma_{xi}^2$.

Figure 3:
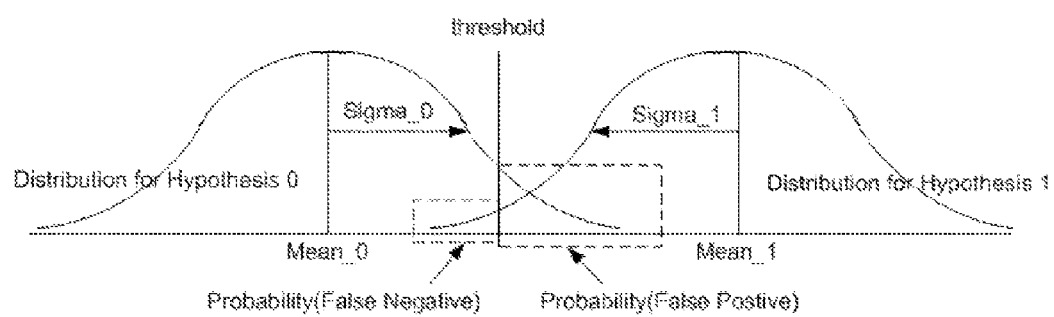
FIG. 3: determining probability of false negatives and false positives for different hypotheses.

FIG. 3 illustrates how to determine the probability of false negatives and false positive detections. Assume that a threshold t is set half-way between $m_1$ and $m_0$ in order to make the probability of false negatives and false positives equal (this need not be the case as is described below). The probability of a false negative is determined by the ratio of $(m_1-t)/\sigma_{m|h1}=(m_1-m_0)/(2\sigma_{m|h1})$. "5-Sigma" statistics may be used so that the probability of false negatives is 1-normcdf(5,0,1)=2.87e−7. In this case, the goal is for $(m_1-m_0)/(2\sigma_{m|h0})>5$ or $10\text{sqrt}((1/N^2)\Sigma_{i=1\ldots N}(s_{xi}(h_1)-s_{xi}(h_0))^2/\sigma_{xi}^2)<(1/N)\Sigma_{i=1\ldots N}(s_{xi}(h_1)-s_{xi}(h_0))^2/\sigma_{xi}^2$ or $\text{sqrt}(\Sigma_{i=1\ldots N}(s_{xi}(h_1)-s_{xi}(h_0))^2/\sigma_{xi}^2)>10$. In order to compute the size of N, Mean Signal to Noise Ratio can be computed from aggregated data: $\text{MSNR}=(1/N)\Sigma_{i=1\ldots N}(s_{xi}(h_1)-s_{xi}(h_0))^2/\sigma_{xi}^2$. N can then be found from the inequality above: $\text{sqrt}(N)\cdot\text{sqrt}(\text{MSNR})>10$ or $N>100/\text{MSNR}$.

Figure 4:
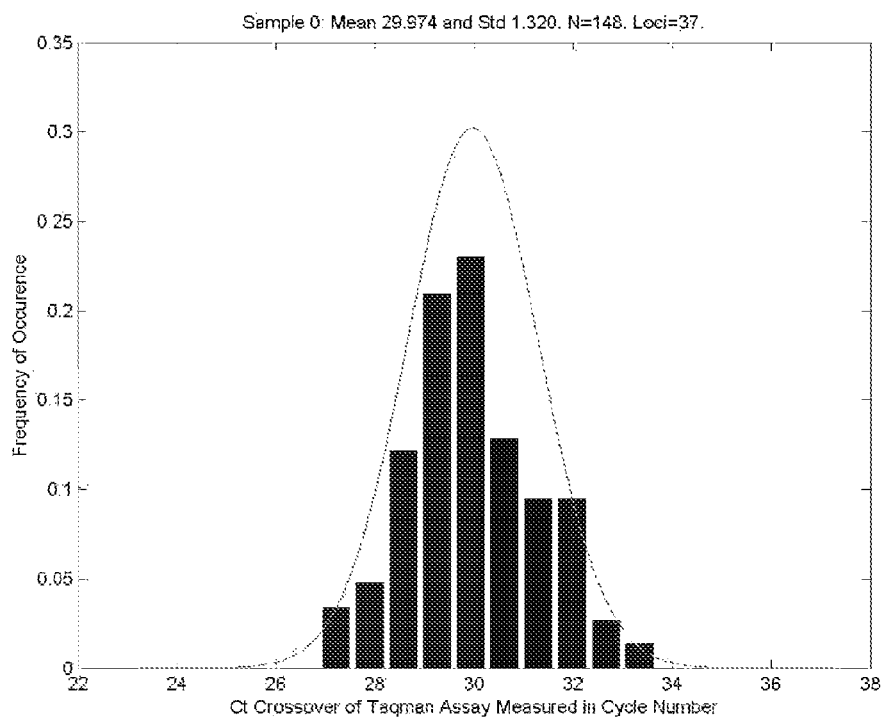
FIG. 4: the results from a mixed female sample, all loci hetero.
Figure 5:
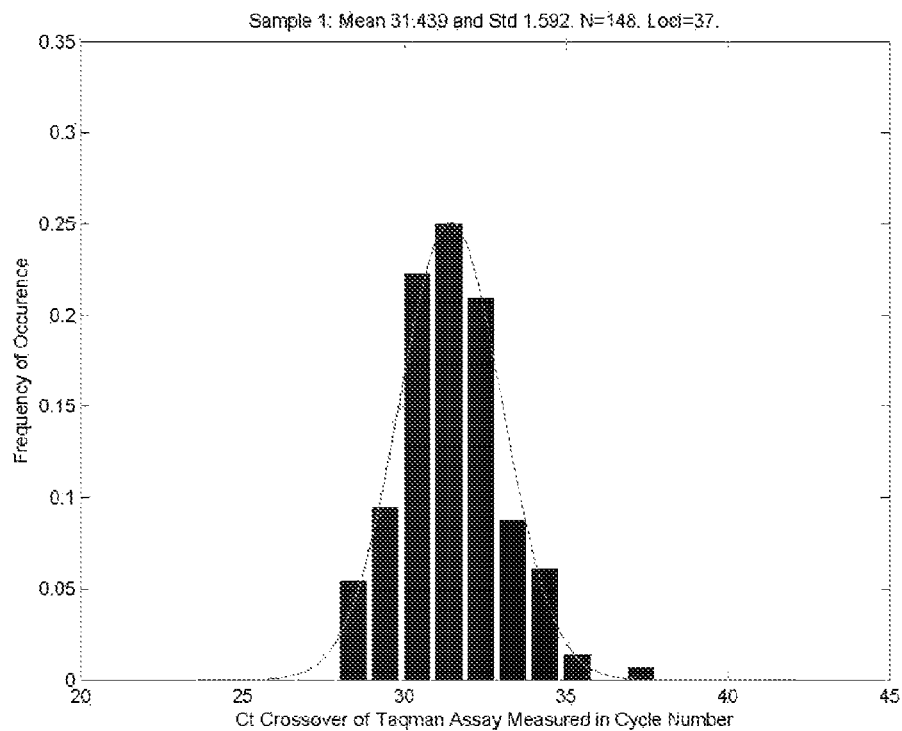
FIG. 5: the results from a mixed male sample, all loci hetero.
Figure 6:
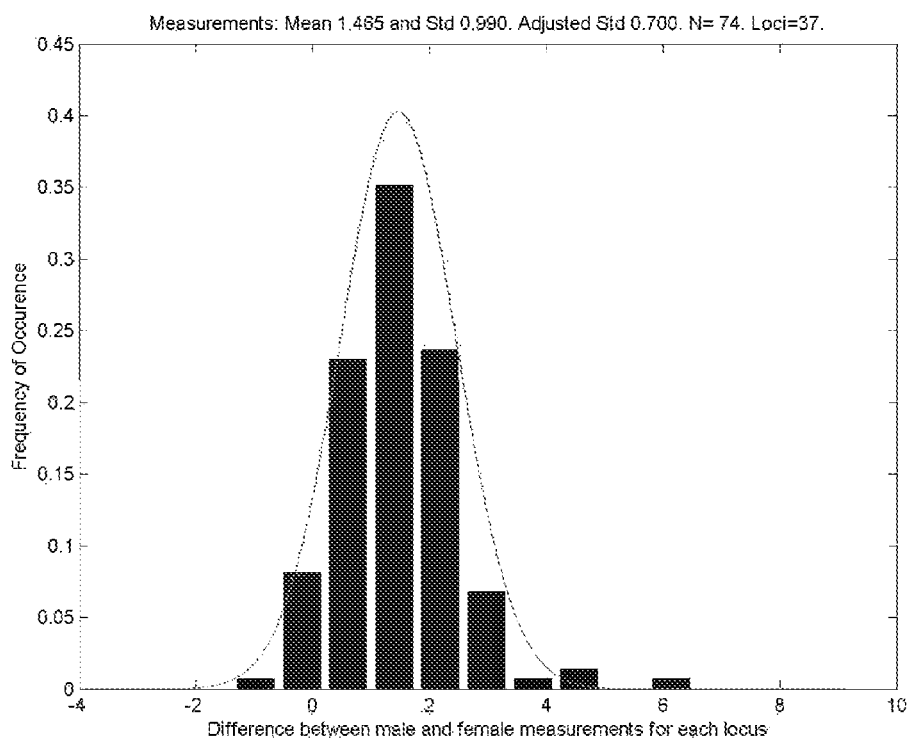
FIG. 6: Ct measurements for male sample differenced from Ct measurements for female sample.

This approach was applied to data measured with the TAQMAN Assay from Applied BioSystems using 48 SNPs on the X chromosome. The measurement for each locus is the time, $C_t$, that it takes the die released in the well corresponding to this locus to exceed a threshold. Sample 0 consists of roughly 0.3 ng (50 cells) of total DNA per well of mixed female origin where subjects had two X chromosomes; sample 1 consisted of roughly 0.3 ng of DNA per well of mixed male origin where subject had one X chromosome. FIG. 4 and FIG. 5 show the histograms of measurements for samples 1 and 0. The distributions for these samples are characterized by $m_0=29.97$; $SD_0=1.32$, $m_1=31.44$, $SD_1=1.592$. Since this data is derived from mixed male and female samples, some of the observed SD is due to the different allele frequencies at each SNP in the mixed samples. In addition, some of the observed SD will be due to the varying efficiency of the different assays at each SNP, and the differing amount of dye pipetted into each well. FIG. 6 provides a histogram of the difference in the measurements at each locus for the male and female sample. The mean difference between the male and female samples is 1.47 and the SD of the difference is 0.99. While this SD will still be subject to the different allele frequencies in the mixed male and female samples, it will no longer be affected the different efficiencies of each assay at each locus. Since the goal is to differentiate two measurements each with a roughly similar SD, the adjusted SD may be approximated for each measurement for all loci as 0.99/sqrt(2)=0.70. Two runs were conducted for every locus in order to estimate $\sigma_{xi}$ for the assay at that locus so that a matched filter could be applied. A lower limit of $\sigma_{xi}$ was set at 0.2 in order to avoid statistical anomalies resulting from only two runs to compute $\sigma_{xi}$. Only those loci (numbering 37) for which there were no allele dropouts over both alleles, over both experiment runs and over both male and female samples were used in the plots and calculations. Applying the approach above to this data, it was found that MSNR=2.26, hence $N=2^2 5^2/2.26^2=17$ loci.

Method 1b: Measuring Aneuploidy or Sex by Quantitative Techniques that do not Make Allele Calls when the Mean and Std. Deviation is not Known or is Uniform When the characteristics of each locus are not known well, the simplifying assumptions that all the assays at each locus will behave similarly can be made, namely that $E(m_{xi})$ and $\sigma_{xi}$ are constant across all loci i, so that it is possible to refer instead only to $E(m_x)$ and $\sigma_x$. In this case, the matched filtering approach $m=h^T d_x$ reduces to finding the mean of the distribution of $d_x$. This approach will be referred to as comparison of means, and it will be used to estimate the number of loci required for different kinds of detection using real data.

As above, consider the scenario when there are two chromosomes present in the sample (hypothesis $h_0$) or one chromosome present ($h_1$). For $h_0$, the distribution is $N(\mu_0, \sigma_0^2)$ and for $h_1$ the distribution is $N(\mu_1,\sigma_1^2)$. Measure each of the distributions using $N_0$ and $N_1$ samples respectively, with measured sample means and SDs $m_1$, $m_0$, $s_1$, and $s_0$. The means can be modeled as random variables $M_0$, $M_1$ that are normally distributed as $M_0\sim N(\mu_0, \sigma_0^2/N_0)$ and $M_1\sim N(\mu_1, \sigma_1^2/N_1)$. Assume $N_1$ and $N_0$ are large enough (>30) so that one can assume that $M_1\sim N(m_1, s_1^2/N_1)$ and $M_0\sim N(m_0, s_0^2/N_0)$. In order to test whether the distributions are different, the difference of the means test may be used, where $d=m_1-m_0$. The variance of the random variable D is $\sigma_d^2=\sigma_1^2/N_1+\sigma_0^2/N_0$ which may be approximated as $\sigma_d^2=s_1^2/N_1+s_0^2/N_0$. Given $h_0$, $E(d)=0$; given $h_1$, $E(d)=\mu_1-\mu_0$. Different techniques for making the call between $h_1$ for $h_0$ will now be discussed.

Figure 7:
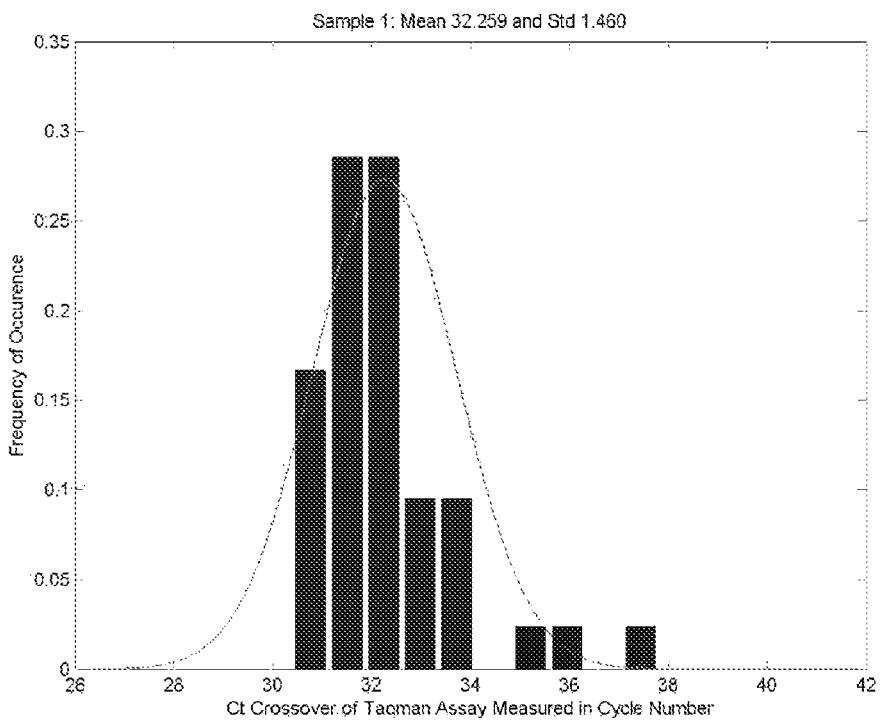
FIG. 7: the results from a mixed female sample; TAQMAN single dye.
Figure 8:
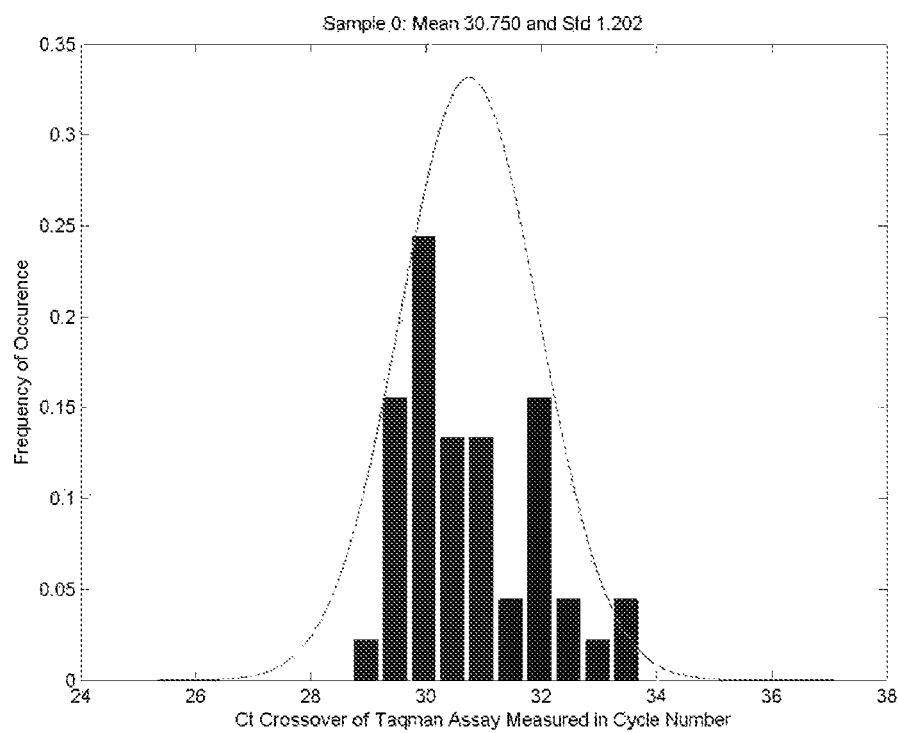
FIG. 8: the results from a mixed male; TAQMAN single dye.

Data measured with a different run of the TAQMAN Assay using 48 SNPs on the X chromosome was used to calibrate performance. Sample 1 consists of roughly 0.3 ng of DNA per well of mixed male origin containing one X chromosome; sample 0 consisted of roughly 0.3 ng of DNA per well of mixed female origin containing two X chromosomes. $N_1=42$ and $N_0=45$. FIG. 7 and FIG. 8 show the histograms for samples 1 and 0. The distributions for these samples are characterized by $m_1=32.259$, $s_1=1.460$, $\sigma_{m1}=s_1/\text{sqrt}(N_1)=0.225$; $m_0=30.75$; $s_0=1.202$, $\sigma_{m0}=s_0/\text{sqrt}(N_0)=0.179$. For these samples $d=1.509$ and $\sigma_d=0.2879$.

Figure 9:
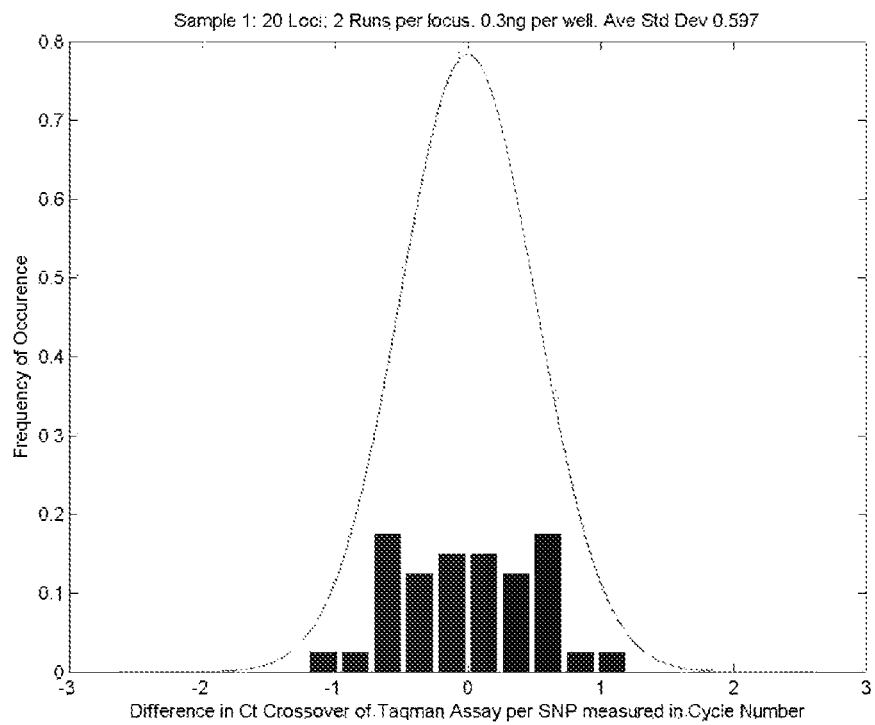
FIG. 9: the distribution of repeated measurements for mixed male sample.

Since this data is derived from mixed male and female samples, much of the standard deviation is due to the different allele frequencies at each SNP in the mixed samples. SD is estimated by considering the variations in $C_t$ for one SNP at a time, over multiple runs. This data is shown in FIG. 9. The histogram is symmetric around 0 since $C_t$ for each SNP is measured in two runs or experiments and the mean value of Ct for each SNP is subtracted out. The average std. dev. across 20 SNPs in the mixed male sample using two runs is s=−0.597. This SD will be conservatively used for both male and female samples, since SD for the female sample will be smaller than for the male sample. In addition, note that the measurement from only one dye is being used, since the mixed samples are assumed to be heterozygous for all SNPs. The use of both dyes requires the measurements of each allele at a locus to be combined, which is more complicated (see section on linearizing measurements). Combining measurements on both dyes would double signal amplitude and increase noise amplitude by roughly sqrt(2), resulting in an SNR improvement of roughly sqrt(2) or 3 dB.

Detection Assuming No Mosaicism and No Reference Sample

Assume that $m_0$ is known perfectly from many experiments, and every experiment runs only one sample to compute $m_1$ to compare with $m_0$. $N_1$ is the number of assays and assume that each assay is a different SNP locus. A threshold t can be set half way between $m_0$ and $m_1$ to make the likelihood of false positives equal the number of false negatives, and a sample is labeled abnormal if it is above the threshold. Assume $s_1=s_2=s=0.597$ and use the 5-sigma approach so that the probability of false negatives or positives is 1−normcdf(5,0,1)=2.87e-7. The goal is for $5s_1/\text{sqrt}(N_1) < (m_1-m_0)/2$, hence $N_1=100\ s_1^2/(m_1-m_0)2=16$. Now, an approach where the probability of a false positive is allowed to be higher than the probability of a false negatives, which is the harmful scenario, may also be used. If a positive is measured, the experiment may be rerun. Consequently, it is possible to say that the probability of a false negative should be equal to the square of the probability of a false positive. Consider FIG. 3, let t=threshold, and assume Sigma_0=Sigma_1=s. Thus $(1-\text{normcdf}((t-m_0)/s,0,1))^2=1-\text{normcdf}((m_1-t)/s,0,1)$. Solving this, it can be shown that $t=m_0+0.32(m_1-m_0)$. Hence the goal is for $5s/\text{sqrt}(N_1) < m_1-m_0-0.32(m_1-m_0)=(m_1-m_0)/1.47$, hence $N_1=(5^2)(1.47^2)s^2/(m_1-m_0)^2=9$.

Detection with Mosaicism without Running a Reference Sample

Assume the same situation as above, except that the goal is to detect mosaicism with a probability of 97.7% (i.e. 2-sigma approach). This is better than the standard approach to amniocentesis which extracts roughly 20 cells and photographs them. If one assumes that 1 in 20 cells is aneuploid and this is detected with 100% reliability, the probability of having at least one of the group being aneuploid using the standard approach is $1-0.95^{20}=64\%$. If 0.05% of the cells are aneuploid (call this sample 3) then $m_3=0.95m_0+0.05m_1$ and $\text{var}(m_3)=(0.95s_0^2+0.05s_1^2)/N_1$. Thus $\text{std}(m_3)2<(m_3-m_0)/2 \Rightarrow \text{sqrt}(0.95s_0^2+0.05s_1^2)/\text{sqrt}(N_1)<0.05(m_1-m_2)/4 \Rightarrow N_1=16(0.95s_2^2+0.05s_1^2)/(0.05^2(m_1-m_2)^2)=1001$. Note that using the goal of 1-sigma statistics, which is still better than can be achieved using the conventional approach (i.e. detection with 84.1% probability), it can be shown in a similar manner that $N_1=250$.

Detection with No Mosaicism and Using a Reference Sample

Although this approach may not be necessary, assume that every experiment runs two samples in order to compare $m_1$ with truth sample $m_2$. Assume that $N=N_1=N_0$. Compute $d=m_1-m_0$ and, assuming $\sigma_1=\sigma_0$, set a threshold $t=(m_0+m_1)/2$ so that the probability of false positives and false negatives is equal. To make the probability of false negatives 2.87e-7, it must be the case that $(m_1-m_2)/2>5\text{sqrt}(s_1^2/N+s_2^2/N) \Rightarrow N=100(s_1^2+s_2^2)/(m_1-m_2)^2=32$.

Detection with Mosaicism and Running a Reference Sample

As above, assume the probability of false negatives is 2.3% (i.e. 2-sigma approach). If 0.05% of the cells are aneuploid (call this sample 3) then $m_3=0.95m_0+0.05m_1$ and $\text{var}(m_3)=(0.95s_0^2+0.05s_1^2)/N_1$. $d=m_3-m_2$ and $\sigma_d^2=(1.95s_0^2+0.05s_1^2)/N$. It must be that $\text{std}(m_3)2<(m_0-m_2)/2 \Rightarrow \text{sqrt}(1.95s_2^2+0.05s_1^2)/\text{sqrt}(N)<0.05(m_1-m_2)/4 \Rightarrow N=16(1.95s_2^2+0.05s_1^2)/(0.05^2(m_1-m_2)^2)=2002$. Again using 1-sigma approach, it can be shown in a similar manner that N=500.

Consider the case if the goal is only to detect 5% mosaicism with a probability of 64% as is the current state of the art. Then, the probability of false negative would be 36%. In other words, it would be necessary to find x such that 1−normcdf(x,0,1)=36%. Thus $N=4(0.36^2)(1.95s_2^2+0.05s_1^2)/(0.05^2(m_1-m_2)^2)=65$ for the 2-sigma approach, or N=33 for the 1-sigma approach. Note that this would result in a very high level of false positives, which needs to be addressed, since such a level of false positives is not currently a viable alternative.

Also note that if N is limited to 384 (i.e. one 384 well TAQMAN plate per chromosome), and the goal is to detect mosaicism with a probability of 97.72%, then it will be possible to detect mosaicism of 8.1% using the 1-sigma approach. In order to detect mosaicism with a probability of 84.1% (or with a 15.90% false negative rate), then it will be possible to detect mosaicism of 5.8% using the 1-sigma approach. To detect mosaicism of 19% with a confidence of 97.72% it would require roughly 70 loci. Thus one could screen for 5 chromosomes on a single plate.

Figure 10:
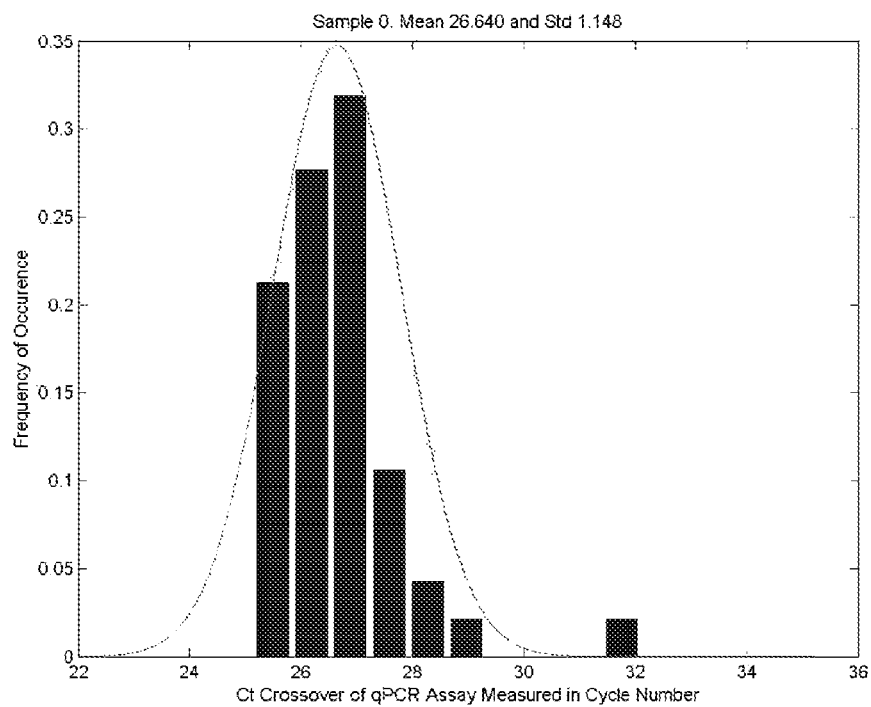
FIG. 10: the results from a mixed female sample; qPCR measures.
Figure 11:
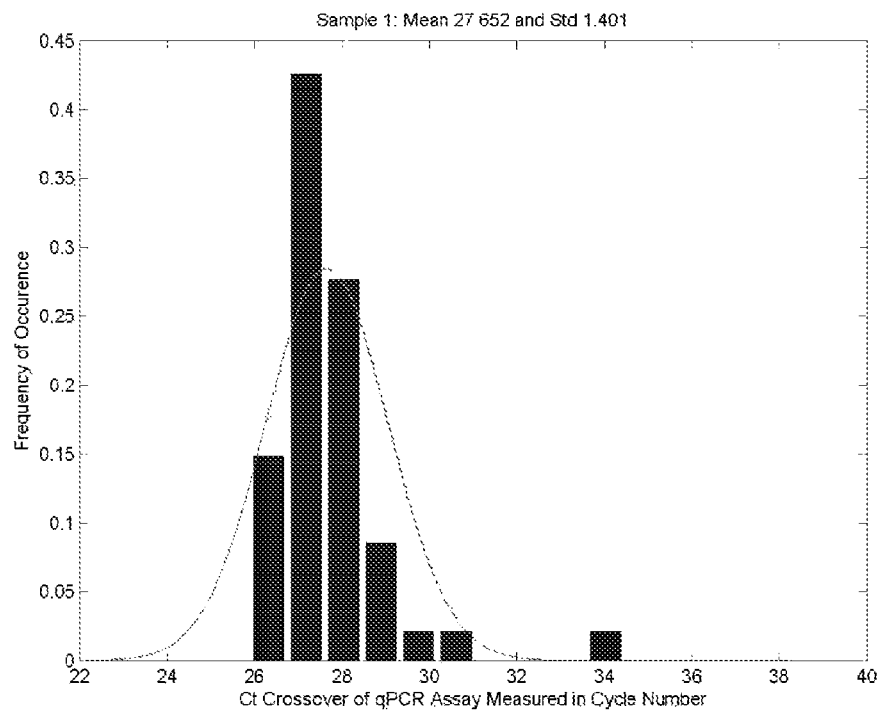
FIG. 11: the results from a mixed male sample; qPCR measures.
Figure 12:
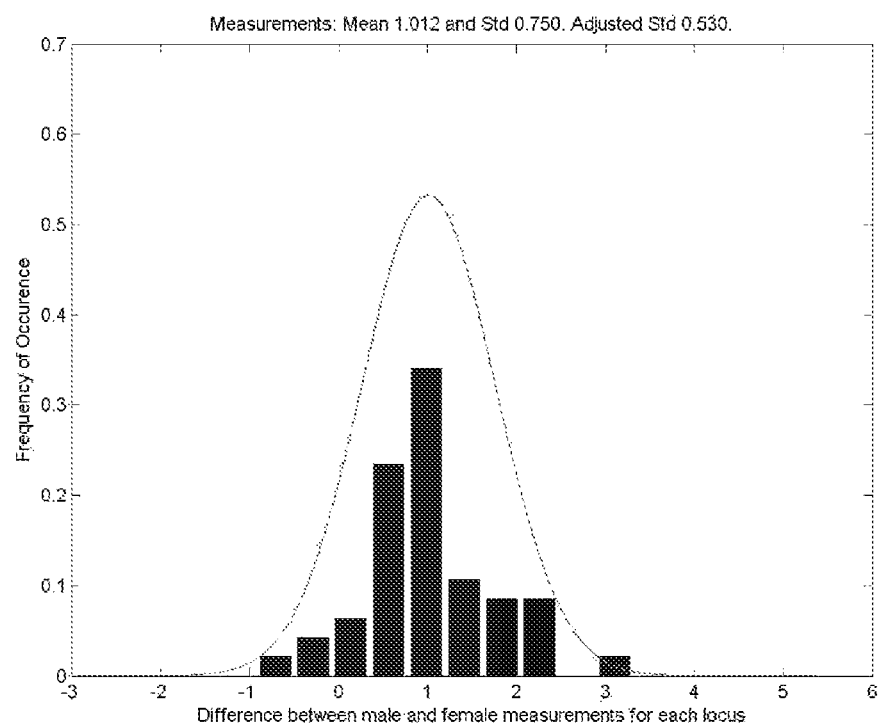
FIG. 12: Ct measurements for male sample differenced from Ct measurements for female sample.

The summary of each of these different scenarios is provided in FIG. 20. Also included in FIG. 20 are the results generated from qPCR and the SYBR assays. The methods described above were used and the simplifying assumption was made that the performance of the qPCR assay for each locus is the same. FIG. 10 and FIG. 11 show the histograms for samples 1 and 0, as described above. $N_0=N_1=47$. The distributions of the measurements for these samples are characterized by $m_1=27.65$, $s_1=1.40$, $\sigma_{m1}=s_1/\text{sqrt}(N_1)=0.204$; $m_0=26.64$; $s_0=1.146$, $\sigma_{m0}=s_0/\text{sqrt}(N_0)=0.167$. For these samples $d=1.01$ and $\sigma_d=0.2636$. FIG. 12 shows the difference between $C_t$ for the male and female samples for each locus, with a standard deviation of the difference over all loci of 0.75. The SD was approximated for each measurement of each locus on the male or female sample as $0.75/\text{sqrt}(2)=0.53$.

Method 2: Qualitative Techniques that Use Allele Calls

Figure 13:
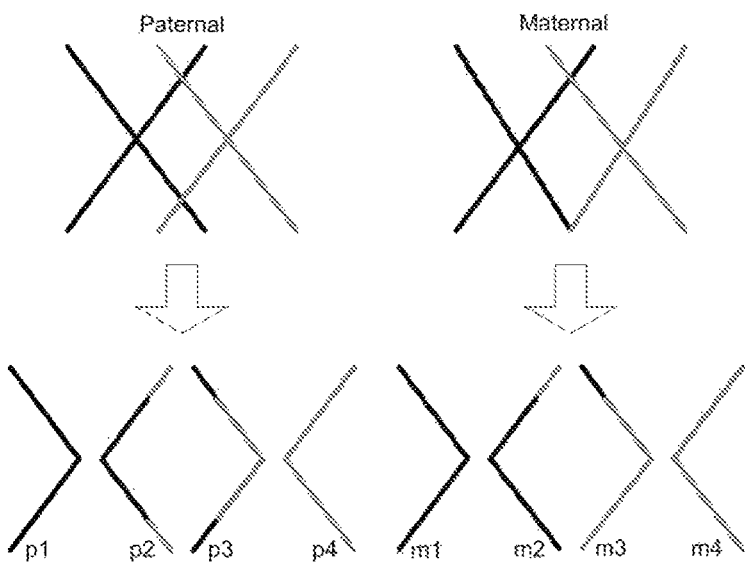
FIG. 13: detecting aneuploidy with a third dissimilar chromosome.

In this section, no assumption is made that the assay is quantitative. Instead, the assumption is that the allele calls are qualitative, and that there is no meaningful quantitative data coming from the assays. This approach is suitable for any assay that makes an allele call. FIG. 13 describes how different haploid gametes form during meiosis, and will be used to describe the different kinds of aneuploidy that are relevant for this section. The best algorithm depends on the type of aneuploidy that is being detected.

Consider a situation where aneuploidy is caused by a third segment that has no section that is a copy of either of the other two segments. From FIG. 13, the situation would arise, for example, if $p_1$ and $p_4$, or $p_2$ and $p_3$, both arose in the child cell in addition to one segment from the other parent. This is very common, given the mechanism which causes aneuploidy. One approach is to start off with a hypothesis $h_0$ that there are two segments in the cell and what these two segments are. Assume, for the purpose of illustration, that $h_0$ is for $p_3$ and $m_4$ from FIG. 13. In a preferred embodiment this hypothesis comes from algorithms described elsewhere in this document. Hypothesis $h_1$ is that there is an additional segment that has no sections that are a copy of the other segments. This would arise, for example, if $p_2$ or $m_1$ was also present. It is possible to identify all loci that are homozygous in $p_3$ and $m_4$. Aneuploidy can be detected by searching for heterozygous genotype calls at loci that are expected to be homozygous.

Assume every locus has two possible alleles, x and y. Let the probability of alleles x and y in general be $p_x$ and $p_y$ respectively, and $p_x + p_y = 1$. If $h_1$ is true, then for each locus i for which $p_3$ and $m_4$ are homozygous, then the probability of a non-homozygous call is $p_y$ or $p_x$, depending on whether the locus is homozygous in x or y respectively. Note: based on knowledge of the parent data, i.e. $p_1$, $p_2$, $p_4$ and $m_1$, $m_2$, $m_3$, it is possible to further refine the probabilities for having non-homozygous alleles x or y at each locus. This will enable more reliable measurements for each hypothesis with the same number of SNPs, but complicates notation, so this extension will not be explicitly dealt with. It should be clear to someone skilled in the art how to use this information to increase the reliability of the hypothesis.

The probability of allele dropouts is $p_d$. The probability of finding a heterozygous genotype at locus i is $p_{0i}$ given hypothesis $h_0$ and $p_{1i}$ given hypothesis $h_1$.

Given $h_0$: $p_{0i} = 0$

Given $h_1$: $p_{1i} = p_x(1 - p_d)$ or $p_{1i} = p_y(1 - p_d)$ depending on whether the locus is homozygous for x or y.

Create a measurement $m = 1/N_h \Sigma_{i=1 \ldots Nh} I_i$ where $I_i$ is an indicator variable, and is 1 if a heterozygous call is made and 0 otherwise. $N_h$ is the number of homozygous loci. One can simplify the explanation by assuming that $p_x = p_y$ and $p_{0i}$, $p_{1i}$ for all loci are the same two values $p_0$ and $p_1$. Given $h_0$, $E(m) = p_0 = 0$ and $\sigma^2_{m|h0} = p_0(1 - p_0)/N_h$. Given $h_1$, $E(m) = p_1$ and $\sigma^2_{m|h1} = p_1(1 - p_1)/N_h$. Using 5 sigma-statistics, and making the probability of false positives equal the probability of false negatives, it can be shown that $(p_1 - p_0)/2 > 5\sigma_{m|h1}$ hence $N_h = 100(p_0(1-p_0) + p_1(1-p_1))/(p_1 - p_0)^2$. For 2-sigma confidence instead of 5-sigma confidence, it can be shown that $N_h = 4.2^2(p_0(1-p_0) + p_1(1-p_1))/(p_1 - p_0)^2$.

It is necessary to sample enough loci N that there will be sufficient available homozygous loci $N_{h\text{-}avail}$ such that the confidence is at least 97.7% (2-sigma). Characterize $N_{h\text{-}avail} = \Sigma_{i=1 \ldots N} J_i$ where $J_i$ is an indicator variable of value 1 if the locus is homozygous and 0 otherwise. The probability of the locus being homozygous is $p_x^2 + p_y^2$. Consequently, $E(N_{h\text{-}avail}) = N(p_x^2 + p_y^2)$ and $\sigma_{Nh\text{-}avail}^2 = N(p_x^2 + p_y^2)(1 - p_x^2 - p_y^2)$. To guarantee N is large enough with 97.7% confidence, it must be that $E(N_{h\text{-}avail}) - 2\sigma N_{h\text{-}avail} = N_h$ where $N_h$ is found from above.

For example, if one assumes $p_d = 0.3$, $p_x = p_y = 0.5$, one can find $N_h = 186$ and $N = 391$ for 5-sigma confidence. Similarly, it is possible to show that $N_h = 30$ and $N = 68$ for 2-sigma confidence i.e. 97.7% confidence in false negatives and false positives.

Note that a similar approach can be applied to looking for deletions of a segment when $h_0$ is the hypothesis that two known chromosome segment are present, and $h_1$ is the hypothesis that one of the chromosome segments is missing. For example, it is possible to look for all of those loci that should be heterozygous but are homozygous, factoring in the effects of allele dropouts as has been done above.

Also note that even though the assay is qualitative, allele dropout rates may be used to provide a type of quantitative measure on the number of DNA segments present.

Method 3: Making Use of Known Alleles of Reference Sequences, and Quantitative Allele Measurements Here, it is assumed that the alleles of the normal or expected set of segments are known. In order to check for three chromosomes, the first step is to clean the data, assuming two of each chromosome. In a preferred embodiment of the invention, the data cleaning in the first step is done using methods described elsewhere in this document. Then the signal associated with the expected two segments is subtracted from the measured data. One can then look for an additional segment in the remaining signal. A matched filtering approach is used, and the signal characterizing the additional segment is based on each of the segments that are believed to be present, as well as their complementary chromosomes. For example, considering FIG. 13, if the results of PS indicate that segments p2 and m1 are present, the technique described here may be used to check for the presence of p2, p3, m1 and m4 on the additional chromosome. If there is an additional segment present, it is guaranteed to have more than 50% of the alleles in common with at least one of these test signals. Note that another approach, not described in detail here, is to use an algorithm described elsewhere in the document to clean the data, assuming an abnormal number of chromosomes, namely 1, 3, 4 and 5 chromosomes, and then to apply the method discussed here. The details of this approach should be clear to someone skilled in the art after having read this document.

Hypothesis $h_0$ is that there are two chromosomes with allele vectors $a_1$, $a_2$. Hypothesis $h_1$ is that there is a third chromosome with allele vector $a_3$. Using a method described in this document to clean the genetic data, or another technique, it is possible to determine the alleles of the two segments expected by $h_0$: $a_1 = [a_{11} \ldots a_{1N}]$ and $a_2 = [a_{21} \ldots a_{2N}]$ where each element $a_{ji}$ is either x or y. The expected signal is created for hypothesis $h_0$: $s_{0x} = [f_{0x}(a_{11}, a_{21}) \ldots f_{x0}(a_{1N}, a_{2N})]$, $s_{0y} = [f_y(a_{11}, a_{21}) \ldots f_y(a_{1N}, a_{2N})]$ where $f_x$, $f_y$ describe the mapping from the set of alleles to the measurements of each allele. Given $h_0$, the data may be described as $d_{xi} = s_{0xi} + n_{xi}$, $n_{xi} \sim N(0, \sigma_{xi}^2)$; $d_{yi} = s_{0yi} + n_{yi}$, $n_{yi} \sim N(0, \sigma_{yi}^2)$. Create a measurement by differencing the data and the reference signal: $m_{xi} = d_{xi} - s_{xi}$; $m_{yi} = d_{yi} - s_{yi}$. The full measurement vector is $m = [m_x^T m_y^T]^T$.

Now, create the signal for the segment of interest—the segment whose presence is suspected, and will be sought in the residual—based on the assumed alleles of this segment: $a_3 = [a_{31} \ldots a_{3N}]$. Describe the signal for the residual as: $s_r = [s_{rx}^T s_{ry}^T]^T$ where $s_{rx} = [f_{rx}(a_{31}) \ldots f_{rx}(a_{3N})]$, $s_{ry} = [f_{ry}(a_{31}) \ldots f_{ry}(a_{3N})]$ where $f_{rx}(a_{3i}) = \delta_{xi}$ if $a_{3i} = x$ and 0 otherwise, $f_{ry}(a_{3i}) = \delta_{yi}$ if $a_{3i} = y$ and 0 otherwise. This analysis assumes that the measurements have been linearized (see section below) so that the presence of one copy of allele x at locus i generates data $\delta_{xi} + n_{xi}$ and the presence of $\kappa_x$ copies of the allele x at locus i generates data $\kappa_x \delta_{xi} + n_{xi}$. Note however that this assumption is not necessary for the general approach described here. Given $h_1$, if allele $a_{3i} = x$ then $m_{xi} = \delta_{xi} + n_{xi}$, $m_{yi} = n_{yi}$ and if $a_{3i} = y$ then $m_{xi} = n_{xi}$, $m_{yi} = \delta_{yi} + n_{yi}$. Consequently, a matched filter $h = (1/N)R^{-1}s_r$ can be created where $R = \text{diag}([\sigma_{x1}^2 \ldots \sigma_{xN}^2 \sigma_{y1}^2 \ldots \sigma_{yN}^2])$. The measurement is $m = h^T d$.

$$h_0: m = (1/N)\Sigma_{i=1 \ldots N} s_{rxi} n_{xi}/\sigma_{xi}^2 + s_{ryi} n_{yi}/\sigma_{yi}^2$$

$$h_1: m = (1/N)\Sigma_{i=1 \ldots N} s_{rxi}(\delta_{xi} + n_{xi})/\sigma_{xi}^2 + s_{ryi}(\delta_{yi} + n_{yi})/\sigma_{yi}^2$$

In order to estimate the number of SNPs required, make the simplifying assumptions that all assays for all alleles and all loci have similar characteristics, namely that $\delta_{xi} = \delta_{yi} = \delta$ and $\sigma_{xi} = \sigma_{yi} = \sigma$ for $i = 1 \ldots N$. Then, the mean and standard deviation may be found as follows:

$h_0: E(m)=m_0=0; \sigma_{m|h0}^2 = (1/N^2\sigma^4)(N/2)(\sigma^2\delta^2+\sigma^2\delta^2) = \delta^2/(N\sigma^2)$ $h_1: E(m)=m_1=(1/N)(N/2\sigma^2)(\delta^2+\delta^2) = \delta^2/\sigma^2; \sigma_{m|h1}^2 = (1/N^2\sigma^4)(N)(\sigma^2\delta^2) = \delta^2/(N\sigma^2)$ Now compute a signal-to-noise ratio (SNR) for this test of $h_1$ versus $h_0$. The signal is $m_1-m_0=\delta^2/\sigma^2$, and the noise variance of this measurement is $\sigma_{m|h0}^2+\sigma_{m|h1}^2=2\delta^2/(N\sigma^2)$. Consequently, the SNR for this test is $(\delta^4/\sigma^4)/(2\delta^2/(N\sigma^2))=N\delta^2/(2\sigma^2)$.

Compare this SNR to the scenario where the genetic information is simply summed at each locus without performing a matched filtering based on the allele calls. Assume that $h=(1/N)\vec{1}$ where $\vec{1}$ is the vector of N ones, and make the simplifying assumptions as above that $\delta_{xi}=\delta_{yi}=\delta$ and $\sigma_{xi}=\sigma_{yi}=\sigma$ for $i=1 \ldots N$. For this scenario, it is straightforward to show that if $m=h^T d$:

$h_0: E(m)=m_0=0; \sigma_{m|h0}^2 = N\sigma^2/N^2 + N\sigma^2/N^2 = 2\sigma^2/N$ $h_1: E(m)=m_1=(1/N)(N\delta/2+N\delta/2)=\delta; \sigma_{m|h1}^2=(1/N^2)(N\sigma^2+N\sigma^2)=2\sigma^2/N$ Consequently, the SNR for this test is $N\delta^2/(4\sigma^2)$. In other words, by using a matched filter that only sums the allele measurements that are expected for segment $a_3$, the number of SNPs required is reduced by a factor of 2. This ignores the SNR gain achieved by using matched filtering to account for the different efficiencies of the assays at each locus.

Note that if we do not correctly characterize the reference signals $s_{xi}$ and $s_{yi}$ then the SD of the noise or disturbance on the resulting measurement signals $m_{xi}$ and $m_{yi}$ will be increased. This will be insignificant if $\delta \ll \sigma$, but otherwise it will increase the probability of false detections. Consequently, this technique is well suited to test the hypothesis where three segments are present and two segments are assumed to be exact copies of each other. In this case, $s_{xi}$ and $s_{yi}$ will be reliably known using techniques of data cleaning based on qualitative allele calls described elsewhere. In one embodiment method 3 is used in combination with method 2 which uses qualitative genotyping and, aside from the quantitative measurements from allele dropouts, is not able to detect the presence of a second exact copy of a segment.

We now describe another quantitative technique that makes use of allele calls. The method involves comparing the relative amount of signal at each of the four registers for a given allele. One can imagine that in the idealized case involving a single, normal cell, where homogenous amplification occurs, (or the relative amounts of amplification are normalized), four possible situations can occur: (i) in the case of a heterozygous allele, the relative intensities of the four registers will be approximately 1:1:0:0, and the absolute intensity of the signal will correspond to one base pair; (ii) in the case of a homozygous allele, the relative intensities will be approximately 1:0:0:0, and the absolute intensity of the signal will correspond to two base pairs; (iii) in the case of an allele where ADO occurs for one of the alleles, the relative intensities will be approximately 1:0:0:0, and the absolute intensity of the signal will correspond to one base pair; and (iv) in the case of an allele where ADO occurs for both of the alleles, the relative intensities will be approximately 0:0:0:0, and the absolute intensity of the signal will correspond to no base pairs.

In the case of aneuploides, however, different situations will be observed. For example, in the case of trisomy, and there is no ADO, one of three situations will occur: (i) in the case of a triply heterozygous allele, the relative intensities of the four registers will be approximately 1:1:1:0, and the absolute intensity of the signal will correspond to one base pair; (ii) in the case where two of the alleles are homozygous, the relative intensities will be approximately 2:1:0:0, and the absolute intensity of the signal will correspond to two and one base pairs, respectively; (iii) in the case where are alleles are homozygous, the relative intensities will be approximately 1:0:0:0, and the absolute intensity of the signal will correspond to three base pairs. If allele dropout occurs in the case of an allele in a cell with trisomy, one of the situations expected for a normal cell will be observed. In the case of monosomy, the relative intensities of the four registers will be approximately 1:0:0:0, and the absolute intensity of the signal will correspond to one base pair. This situation corresponds to the case of a normal cell where ADO of one of the alleles has occurred, however in the case of the normal cell, this will only be observed at a small percentage of the alleles. In the case of uniparental disomy, where two identical chromosomes are present, the relative intensities of the four registers will be approximately 1:0:0:0, and the absolute intensity of the signal will correspond to two base pairs. In the case of UPD where two different chromosomes from one parent are present, this method will indicate that the cell is normal, although further analysis of the data using other methods described in this patent will uncover this.

In all of these cases, either in cells that are normal, have aneuploides or UPD, the data from one SNP will not be adequate to make a decision about the state of the cell. However, if the probabilities of each of the above hypothesis are calculated, and those probabilities are combined for a sufficient number of SNPs on a given chromosome, one hypothesis will predominate, it will be possible to determine the state of the chromosome with high confidence.

Methods for Linearizing Quantitative Measurements

Many approaches may be taken to linearize measurements of the amount of genetic material at a specific locus so that data from different alleles can be easily summed or differenced. We first discuss a generic approach and then discuss an approach that is designed for a particular type of assay.

Assume data $d_{xi}$ refers to a nonlinear measurement of the amount of genetic material of allele x at locus i. Create a training set of data using N measurements, where for each measurement, it is estimated or known that the amount of genetic material corresponding to data $d_{xi}$ is $\beta_{xi}$. The training set $\beta_{xi}$, $i=1 \ldots N$, is chosen to span all the different amounts of genetic material that might be encountered in practice. Standard regression techniques can be used to train a function that maps from the nonlinear measurement, $d_{xi}$, to the expectation of the linear measurement, $E(\beta_{xi})$. For example, a linear regression can be used to train a polynomial function of order P, such that $E(\beta_{xi})=[1 \ d_{xi} \ d_{xi}^2 \ldots d_{xi}^P]c$ where c is the vector of coefficients $c=[c_0 \ c_1 \ldots c_P]^T$. To train this linearizing function, we create a vector of the amount of genetic material for N measurements $\beta_x=[\beta_{x1} \ldots \beta_{xN}]^T$ and a matrix of the measured data raised to powers $0 \ldots P$: $D=[[1 \ d_{x1} \ d_{x1}^2 \ldots d_{x1}^P]^T \ [1 \ d_{x2} \ d_{x2}^2 \ldots d_{x2}^P]^T \ldots [1 \ d_{xN} \ d_{xN}^2 \ldots d_{xN}^P]^T]^T$. The coefficients can then be found using a least squares fit $c=(D^T D)^{-1} D^T \beta_x$.

Rather than depend on generic functions such as fitted polynomials, we may also create specialized functions for the characteristics of a particular assay. We consider, for example, the TAQMAN assay or a qPCR assay. The amount of die for allele x and some locus i, as a function of time up to the point where it crosses some threshold, may be described as an exponential curve with a bias offset: $g_{xi}(t)=\alpha_{xi}+\beta_{xi}\exp(\gamma_{xi}t)$ where $\alpha_{xi}$ is the bias offset, $\gamma_{xi}$ is the exponential growth rate, and $\beta_{xi}$, corresponds to the amount of genetic material. To cast the measurements in terms of $\beta_{xi}$, compute the parameter $\alpha_{xi}$ by looking at the asymptotic limit of the curve $g_{xi}(-\infty)$ and then may find $\beta_{xi}$ and $\gamma_{xi}$ by taking the log of the curve to obtain $\log(g_{xi}(t)-\alpha_{xi})=\log(\beta_{xi})+\gamma_{xi}t$ and performing a standard linear regression. Once we have values for $\alpha_{xi}$ and $\gamma_{xi}$, another approach is to compute $\beta_{xi}$ from the time, $t_x$, at which the threshold $g_x$ is exceeded. $\beta_{xi}=(g_x-\alpha_{xi})\exp(-\gamma_{xi}t_x)$. This will be a noisy measurement of the true amount of genetic data of a particular allele.

Whatever techniques is used, we may model the linearized measurement as $\beta_{xi}=\kappa_x\delta_{xi}+n_{xi}$ where $\kappa_x$ is the number of copies of allele x, $\delta_{xi}$ is a constant for allele x and locus i, and $n_{xi}\sim N(0, \sigma_x^2)$ where $\sigma_x^2$ can be measured empirically.

Method 4: Using a Probability Distribution Function for the Amplification of Genetic Data at Each Locus The quantity of material for a particular SNP will depend on the number of initial segments in the cell on which that SNP is present. However, due to the random nature of the amplification and hybridization process, the quantity of genetic material from a particular SNP will not be directly proportional to the starting number of segments. Let $q_{s,A}$, $q_{s,G}$, $q_{s,T}$, $q_{s,C}$ represent the amplified quantity of genetic material for a particular SNP s for each of the four nucleic acids (A,C,T,G) constituting the alleles. Note that these quantities may be exactly zero, depending on the technique used for amplification. Also note that these quantities are typically measured from the intensity of signals from particular hybridization probes. This intensity measurement can be used instead of a measurement of quantity, or can be converted into a quantity estimate using standard techniques without changing the nature of the invention. Let qs be the sum of all the genetic material generated from all alleles of a particular SNP: $q_s=q_{s,A}+q_{s,G}+q_{s,T}+q_{s,C}$. Let N be the number of segments in a cell containing the SNP s. N is typically 2, but may be 0, 1 or 3 or more. For any high or medium throughput genotyping method discussed, the resulting quantity of genetic material can be represented as $q_s=(A+A_{\theta,s})N+\theta_s$ where A is the total amplification that is either estimated a-priori or easily measured empirically, $A_{\theta,s}$ is the error in the estimate of A for the SNP s, and $\theta_s$ is additive noise introduced in the amplification, hybridization and other process for that SNP. The noise terms $A_{\theta,s}$ and $\theta_s$ are typically large enough that qs will not be a reliable measurement of N. However, the effects of these noise terms can be mitigated by measuring multiple SNPs on the chromosome. Let S be the number of SNPs that are measured on a particular chromosome, such as chromosome 21. It is possible to generate the average quantity of genetic material over all SNPs on a particular chromosome as follows:

$$q = \frac{1}{S}\sum_{s=1}^{S} q_s = NA + \frac{1}{S}\sum_{s=1}^{S} A_{\theta,s}N + \theta_s \quad (16)$$

Assuming that $A_{\theta,s}$ and $\theta_s$ are normally distributed random variables with 0 means and variances $\sigma^2_{A_{\theta,s}}$ and $\sigma^2_{\theta,s}$, one can model $q=NA+\phi$ where $\phi$ is a normally distributed random variable with 0 mean and variance $$\frac{1}{S}(N^2\sigma^2_{A_{\theta,s}} + \sigma^2_\theta).$$

Consequently, if sufficient number of SNPs are measured on the chromosome such that $S\gg(N^2\sigma^2_{A_{\theta,s}}+\sigma^2_\theta)$, then $N=q/A$ can be accurately estimated.

Figure 14A:
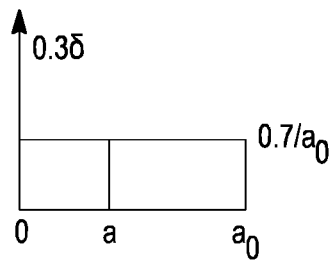
FIGS. 14A and 14B: an illustration of two amplification distributions with constant allele dropout rate.
Figure 14B:
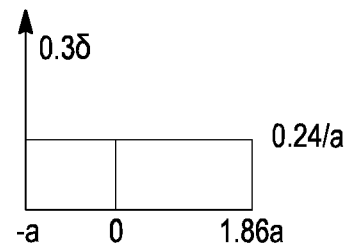

In another embodiment, assume that the amplification is according to a model where the signal level from one SNP is $s=a+\alpha$ where $(a+\alpha)$ has a distribution that looks like the picture in FIG. 14A, left. The delta function at 0 models the rates of allele dropouts of roughly 30%, the mean is a, and if there is no allele dropout, the amplification has uniform distribution from 0 to $a_0$. In terms of the mean of this distribution $a_0$ is found to be $a_0=2.86a$. Now model the probability density function of a using the picture in FIG. 14B, right. Let $s_c$ be the signal arising from c loci; let n be the number of segments; let $\alpha_i$ be a random variable distributed according to FIGS. 14A and 14B that contributes to the signal from locus i; and let $\alpha$ be the standard deviation for all $\{\alpha_i\}$. $s_c=anc+\Sigma_{i=1\ldots nc}\alpha_i$; mean($s_c$)=anc; std($s_c$)=sqrt(nc)$\sigma$. If $\sigma$ is computed according to the distribution in FIG. 14A, right, it is found to be $\sigma=0.907a^2$. We can find the number of segments from $n=s_c/(ac)$ and for "5-sigma statistics" we require std(n)<0.1 so std($s_c$)/(ac)=0.1=>0.95a·sqrt(nc)/(ac)=0.1 so $c=0.95^2$ $n/0.1^2=181$.

Another model to estimate the confidence in the call, and how many loci or SNPs must be measured to ensure a given degree of confidence, incorporates the random variable as a multiplier of amplification instead of as an additive noise source, namely $s=a(1+\alpha)$. Taking logs, $\log(s)=\log(a)+\log(1+\alpha)$. Now, create a new random variable $\gamma=\log(1+\alpha)$ and this variable may be assumed to be normally distributed $\sim N(0, \sigma)$. In this model, amplification can range from very small to very large, depending on a, but never negative. Therefore $\alpha=e^\gamma-1$; and $s_c=\Sigma_{i=1\ldots cn}a(1+\alpha_i)$. For notation, mean($s_c$) and expectation value $E(s_c)$ are used interchangeably $$E(s_c)=acn+aE(\Sigma_{i=1\ldots cn}\alpha_i)=acn+aE(\Sigma_{i=1\ldots cn}\alpha_i)=acn(1+E(\alpha))$$

To find $E(\alpha)$ the probability density function (pdf) must be found for $\alpha$ which is possible since $\alpha$ is a function of $\gamma$ which has a known Gaussian pdf. $p_\alpha(\alpha)=p_\gamma(\gamma)(d\gamma/d\alpha)$. So:

$$p_\gamma(\gamma) = \frac{1}{\sqrt{2\pi}\,\sigma}e^{\frac{-\gamma^2}{2\sigma^2}} \text{ and } \frac{d\gamma}{d\alpha} = \frac{d}{d\alpha}(\log(1+\alpha)) = \frac{1}{1+\alpha} = e^{-\gamma}$$

and:

$$p_\alpha(\alpha) = \frac{1}{\sqrt{2\pi}\,\sigma}e^{\frac{-\gamma^2}{2\sigma^2}}e^{-\gamma} = \frac{1}{\sqrt{2\pi}\,\sigma}e^{\frac{-(\log(1+\alpha))^2}{2\sigma^2}}\frac{1}{1+\alpha}$$

Figure 15:
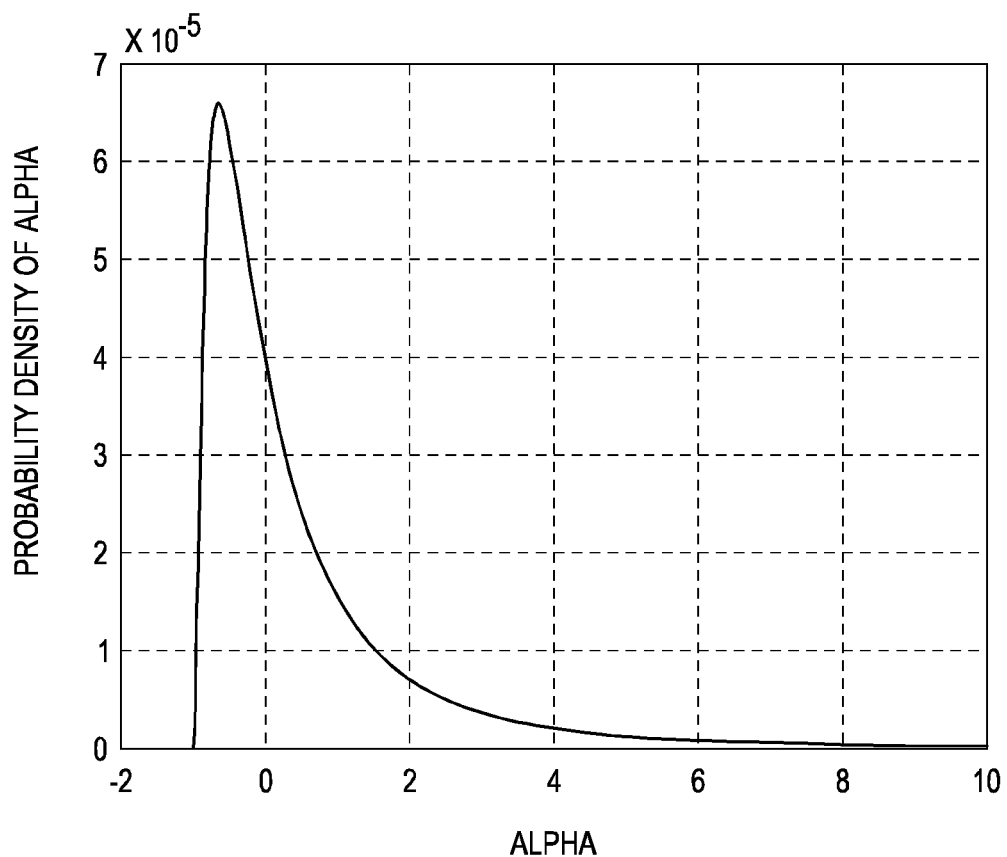
FIG. 15: a graph of the Gaussian probability density function of alpha.

This has the form shown in FIG. 15 for $\sigma=1$. Now, $E(\alpha)$ can be found by integrating over this pdf $E(\alpha)=\int_{-\infty}^{\infty}\alpha p_\alpha(\alpha)d\alpha$ which can be done numerically for multiple different $\sigma$. This gives $E(s_c)$ or mean($s_c$) as a function of $\sigma$. Now, this pdf can also be used to find var($s_c$):

$$\text{var}(s_c) = E(s_c - E(s_c))^2$$

$$= E\left(\sum_{i=1\ldots cn} a(1+\alpha_i) - acn - aE\left(\sum_{i=1\ldots cn}\alpha_i\right)\right)^2$$

$$= E\left(\sum_{i=1\ldots cn} a\alpha_i - aE\left(\sum_{i=1\ldots cn}\alpha_i\right)\right)^2$$

$$= a^2 E\left(\sum_{i=1\ldots cn}\alpha_i - cnE(\alpha)\right)^2$$

-continued $$= a^2 E\left(\left(\sum_{i=1...cn} \alpha_i\right)^2 - 2cnE(\alpha)\left(\sum_{i=1...cn} \alpha_i\right) + c^2 n^2 E(\alpha)^2\right)$$

$$= a^2 E\left(cn\alpha^2 + cn(cn-1)\alpha_i\alpha_j - 2cnE(\alpha)\left(\sum_{i=1...cn} \alpha_i\right) + c^2 n^2 E(\alpha)^2\right)$$

$$= a^2 c^2 n^2 (E(\alpha^2) + (cn-1)E(\alpha_i\alpha_j) - 2cnE(\alpha)^2 + cnE(\alpha)^2)$$

$$= a^2 c^2 n^2 (E(\alpha^2) + (cn-1)E(\alpha_i\alpha_j) - cnE(\alpha)^2)$$

which can also be solved numerically using $p_\alpha(\alpha)$ for multiple different $\sigma$ to get var($s_c$) as a function of $\sigma$. Then, we may take a series of measurements from a sample with a known number of loci c and a known number of segments n and find std($s_c$)/E($s_c$) from this data. That will enable us to compute a value for $\sigma$. In order to estimate n, E($s_c$)=nac(1+E($\alpha$)) so $$\hat{n} = \frac{s_c}{ac(1+E(\alpha))}$$

can be measured so that $$std(\hat{n}) = \frac{std(s_c)}{ac(1+E(\alpha))} std(n)$$

When summing a sufficiently large number of independent random variables of 0-mean, the distribution approaches a Gaussian form, and thus $s_c$ (and $\hat{n}$) can be treated as normally distributed and as before we may use 5-sigma statistics:

$$std(\hat{n}) = \frac{std(s_c)}{ac(1+E(\alpha))} < 0.1$$

in order to have an error probability of 2normcdf(5, 0,1)=2.7e-7. From this, one can solve for the number of loci c.

Sexing

In one embodiment of the system, the genetic data can be used to determine the sex of the target individual. After the method disclosed herein is used to determine which segments of which chromosomes from the parents have contributed to the genetic material of the target, the sex of the target can be determined by checking to see which of the sex chromosomes have been inherited from the father: X indicates a female, and Y indicates a male. It should be obvious to one skilled in the art how to use this method to determine the sex of the target.

Validation of the Hypotheses

In some embodiments of the system, one drawback is that in order to make a prediction of the correct genetic state with the highest possible confidence, it is necessary to make hypotheses about every possible state. However, as the possible number of genetic states are exceptionally large, and computational time is limited, it may not be reasonable to test every hypothesis. In these cases, an alternative approach is to use the concept of hypothesis validation. This involves estimating limits on certain values, sets of values, properties or patterns that one might expect to observe in the measured data if a certain hypothesis, or class of hypotheses are true. Then, the measured values can tested to see if they fall within those expected limits, and/or certain expected properties or patterns can be tested for, and if the expectations are not met, then the algorithm can flag those measurements for further investigation.

For example, in a case where the end of one arm of a chromosome is broken off in the target DNA, the most likely hypothesis may be calculated to be "normal" (as opposed, for example to "aneuploid"). This is because the particular hypotheses that corresponds to the true state of the genetic material, namely that one end of the chromosome has broken off, has not been tested, since the likelihood of that state is very low. If the concept of validation is used, then the algorithm will note that a high number of values, those that correspond to the alleles that lie on the broken off section of the chromosome, lay outside the expected limits of the measurements. A flag will be raised, inviting further investigation for this case, increasing the likelihood that the true state of the genetic material is uncovered.

It should be obvious to one skilled in the art how to modify the disclosed method to include the validation technique. Note that one anomaly that is expected to be very difficult to detect using the disclosed method is balanced translocations.

Application of the Method with Contaminated DNA

In one embodiment of the system, genetic data from target DNA which has been definitely or possibly contaminated with foreign DNA can also be cleaned using the disclosed method. The concept outlined above, that of hypothesis validation, can be used to identify genetic samples that fall outside of expected limits; in the case of contaminated samples it is expected that this validation will cause a flag to be raised, and the sample can be identified as contaminated.

Since large segments of the target DNA will be known from the parental genetic data, and provided the degree of contamination is sufficiently low and sufficient SNPs are measured, the spurious data due to the foreign genetic material can be identified. The method disclosed herein should still allow for the reconstruction of the target genome, albeit with lower confidence levels. Provided that the level of contamination is sufficiently low, the hypothesis that is calculated to be most likely is still expected to correspond to the true state of the genetic material in the target DNA sample.

It should be obvious to one skilled in the art how to optimize these methods for the purpose cleaning genetic data contaminated with spurious signals due to foreign DNA.

Example of Reduction to Practice

Figure 16:
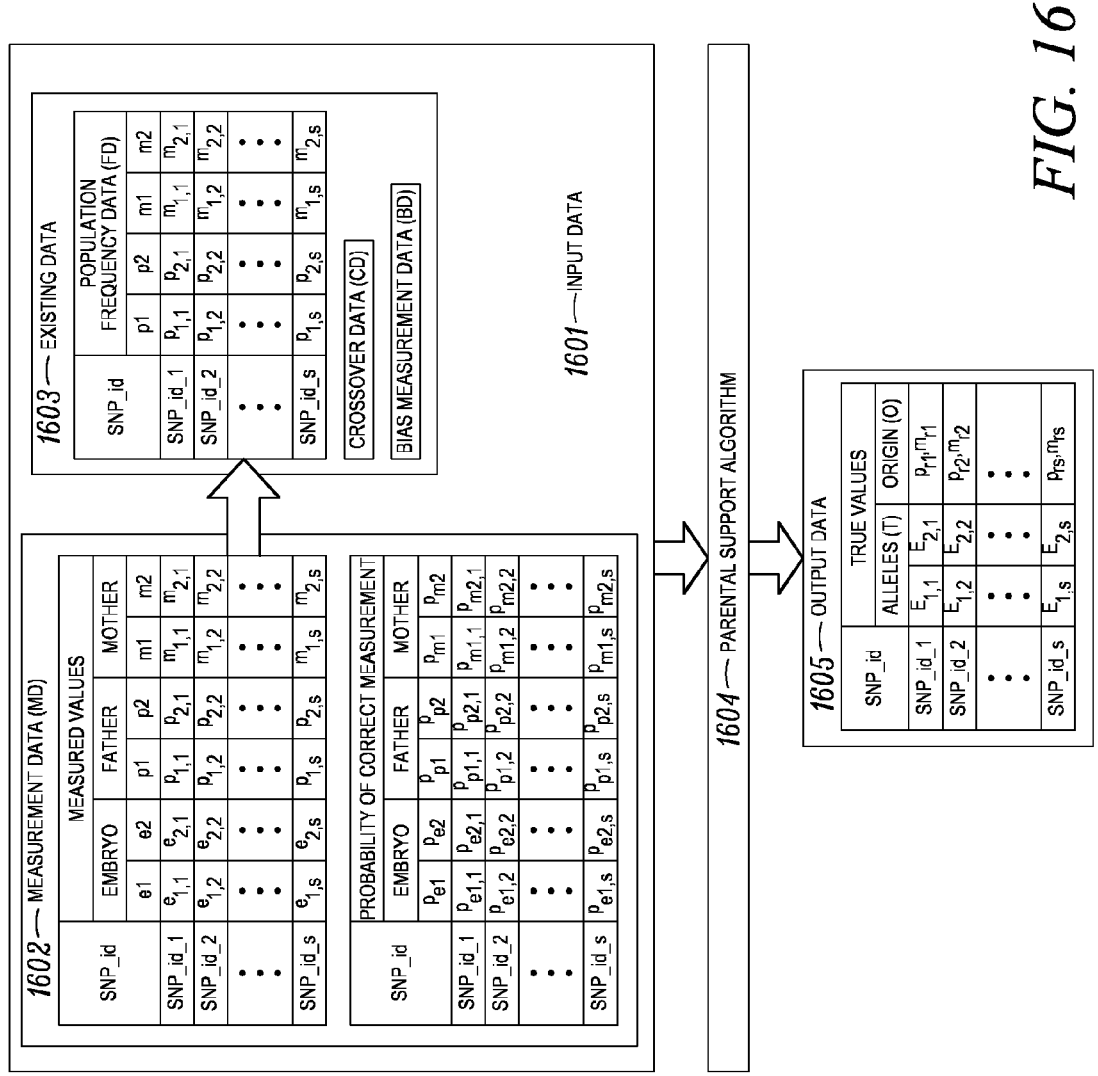
FIG. 16: the general relationship diagram of the input data, the database data, the algorithm and the output.
Figure 17:
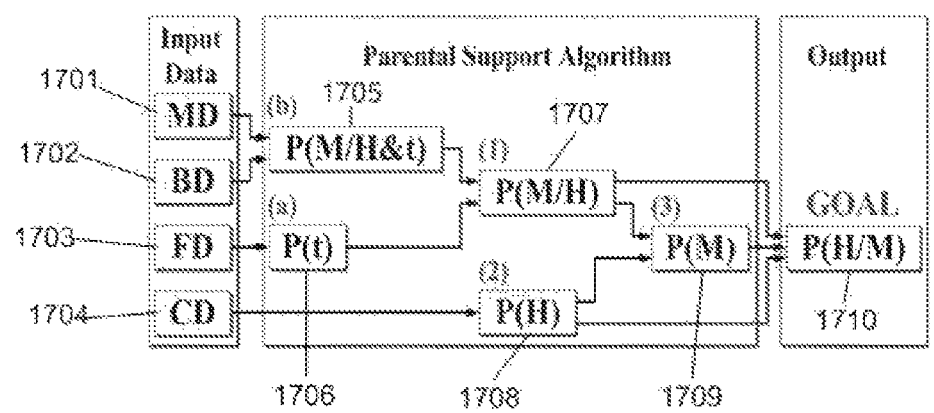
FIG. 17: a visual overview of how to derive P(H|M).

In one embodiment of the system, the method described above can be implemented using a set of algorithms which will calculate the most likely identity of each SNP in a list of relevant SNPs, as well as a confidence level for each SNP call. Described here is one possible way to implement the method disclosed in this patent. FIG. 16 and FIG. 17 visually represent the breakdown of this implementation of the disclosed method, the input requirements and the format of the output. Note that the implementations discussed here were done using the computer program Matlab, and a familiarity with this product will facilitate the understanding of the examples.

FIG. 16 focuses on the input data (1601) and its format and requirements, as well as the output data (1605) and its format. Input to the algorithm consists of the measured data (1602), including input by the user, and existing data (1603) preserved in the database, that is consequently updated by the newly collected data. The measured data (MD, 1602) consists of the genetic data as measured for desired SNPs for the embryo, and the paternal and maternal alleles, as well as the accuracy, or confidence with which each of the alleles is known. The existing data (1603) consists of the population frequency data (FD), measurement bias data (BD), and crossover data (CD).

The population frequency data (FD) contains the allele frequency (for each of the values A,C,T,G) for each of the SNPs available. The data can be previously known or measured, and can be updated with newly collected data as described elsewhere in this document.

Measurement bias data (BD) captures the bias of the measurement process towards certain values. For example, assuming the true value of the allele is X=A, and probability of the correct measurement is $p_X$, the distribution of the measured value x is:

|  | A | C | T | G |
|---|---|---|---|---|
| Probability | $p_X$ | $p_C$ | $p_T$ | $p_G$ |
| probability with no bias | $p_X$ | $(1 - p_X)/3$ | $(1 - p_X)/3$ | $(1 - p_X)/3$ | where $p_X+p_C+p_T+p_G=1$. If there is no bias of measurement towards any of the values then $p_C=p_T=p_G=(1-p_X)/3$. This information can be discerned from empirical and theoretical knowledge about the mechanism of the measurement process and the relevant instruments.

Crossover data (CD) consists of a database of genetic distances and crossover probabilities between pairs of snips, collected from HAPMAP data.

Together, (MD), (FD), (BD), (CD) make up the necessary input to the disclosed method (termed 'Parental Support', 1604) algorithm. This algorithm (1604) then operates on the input data to generate the output data (1605), which describes the most likely "true" value of the target's genetic data given the measured values, as well as the most likely origin of each SNP in terms of the parental alleles.

FIG. 17 focuses on the structure of the algorithm itself (termed 'Parental Support') and how each of these input data are utilized by the algorithm. Working backwards: to find the most likely hypotheses it is necessary to calculate P(H|M) 1707, the probability of the hypothesis given the measurement, for all the possible hypotheses H. As described previously:

$$P(H \mid M) = \frac{P(M \mid H)}{P(M)} P(H), \quad P(M) = \sum_{h \in S_H} P(M \mid h) P(h)$$

In order to find P(H|M) (1710), it is first necessary to find P(M|H) (1707), and P(H) (1708), for all hypotheses H. This allows the calculation of P(M), 1709 by the equation shown above. The probability of the hypothesis P(H) 1708 depends on how many crossovers are assumed and the likelihood of each of these crossovers (CD, 1704), as explained above.

P(M|H) can be calculated using the following equation:

$$P(M \mid H) = \sum_t P(M \mid H \& t) P(t),$$

as explained previously.

P(t), 1706 is the frequency of a particular value t for paternal and maternal alleles and is derived from population frequency data (FD, 1703). P(M|H&t), 1705 is the probability of correctly measuring the allele values of the embryo, the father, and the mother, assuming a particular "true" value t. The measurement data and accuracy entered by the user (MD, 1701), and the measurement bias database (BD, 1702) are the inputs required to calculate P(M|H&t), 1705.

A more detailed description of the method is given forthwith. Begin with SNPs $R=\{r_1, \ldots, r_k\}$, (a set of k SNPs), and the corresponding measured identities of parents and embryo, $M=(e_1, e_2, p_1, p_2, m_1, m_2)$, for k SNPs, identified with id's $s_1, \ldots, s_k$, where:

$e_1=(e_{11}, e_{12}, \ldots, e_{1k})$ is the measurement on one of the chromosomes of the embryo (they don't all have to come from the same parental chromosome) for all the SNPs $e_2=(e_{21}, e_{22}, \ldots, e_{2L})$ is the measurement on the other chromosome of the embryo $p_1=(p_{11}, p_{12}, \ldots, p_{1k})$ is the measurement on the FIRST chromosome of the father (all coming from the same chromosome $p_2=(p_{21}, p_{22}, \ldots, p_{2k})$ is the measurement on the SECOND chromosome of the father (all coming from the same chromosome)

$m_1=(m_{11}, m_{12}, \ldots, m_{1k})$ is the measurement on the FIRST chromosome of the mother (all coming from the same chromosome)

$m_2=(m_{21}, m_{22}, \ldots, m_{2k})$ is the measurement on the SECOND chromosome of the mother (all coming from the same chromosome)

One can also write $M=\{M_1, \ldots, M_k\}$ where $M_i=(e_{1i}, e_{2i}, p_{1i}, p_{2i})$ The goal of the method is to determine the "true" embryo value T=(E1,E2), i.e. the most likely case given the measurement M, where:

$E_1=(E_{11}, E_{12}, \ldots E_{1k})$ is the measurement on the FIRST chromosome of the embryo, corresponding to the PATERNAL chromosome, $E_{1i} \in \{p_{1i}, p_{2i}\}$ $E_2=(E_{21}, E_{22}, \ldots, E_{2k})$ is the measurement on the SECOND chromosome of the embryo, corresponding to the MATERNAL value, $E_{2i} \in \{m_{1i}, m_{2i}\}$ One can also write $T=\{T_1, \ldots, T_k\}$ where $T_i=(E_{1i}, E_{2i})$.

Effectively, the parental chromosome values ($p_1$, $p_2$, $m_1$, $m_2$) are being used as support to check, validate and correct measured values of ($e_1, e_2$), hence the term "Parental Support Algorithm".

To achieve this goal, all the possible hypotheses for the origin of embryo values are developed and the most likely one is chosen, given the measurement M. The hypotheses space is $S_H=\{H^1, \ldots, H^q\}=$ {set of all the hypotheses}, where each hypothesis is of the format $H^j=(H^j_1, \ldots H^j_k)$ where $H^j_i$ is the "mini" hypothesis for SNP i, of the form $H^j_i=(p_i^*, m_i^*)$ where $p_i^* \in \{p_{1i}, p_{2i}\}$ and $m_i^* \in \{m_{1i}, m_{2i}\}$. There are 4 different "mini" hypotheses $H^j_i$, in particular:

$H^j_i1:(e_{1i},e_{2i})=\{(p_{1i},m_{1i})$ or $(m_{1i},p_{1i})\}$; $H^j_i2:(e_{1i},e_{2i})=\{(p_{1i},m_{2i})$ or $(m_{2i},p_{1i})\}$ $H^j_i3:(e_{1i},e_{2i})=\{(p_{2i},m_{1i})$ or $(m_{1i},p_{2i})\}$; $H^j_i4:(e_{1i},e_{2i})=\{(p_{2i},m_{2i})$ or $(m_{2i},p_{2i})\}$

In theory, $S^H$ can have $q=4^k$ different members to pick from, though later this space will be limited with a maximal number of crossovers of paternal and maternal chromosomes.

The most likely hypothesis H* is chosen to be as: $H^*=\operatorname{argmax}_{H \in S_H} P(H|M)$ For a particular H:

$$P(H \mid M) = \frac{P(M \mid H)}{\sum_{h \in S_H} P(M \mid h) P(h)} P(H).$$

So deriving for each hypothesis:
(1) P(M/H) is the probability of measurement M given the particular hypothesis H.
(2) P(H) is the probability of the particular hypothesis H.
(3) P(M) is the probability of the measurement M.

After deriving P(H|M) for all H, the one with the greatest probability is chosen.

Deriving P(M|H)

Since measurements on each SNP are independent, for $M=(M_1, \ldots M_k)$ and the particular hypothesis $H=(H_1, \ldots H_k)$ on all k SNPs then:

$$P(M|H)=P(M_1|H_1)^* \ldots *P(M_k|H_k)$$

For the particular SNP r, derive $P(M_r|H_r)$. For $\Omega=\{A,C,T,G\}X\{A,C,T,G\}X\{A,C,T,G\}X\{A,C,T,G\}$, the space of all the possible values for "true" parent values $(P_{1r},P_{2r},M_{1r},M_{2r})$, by Bayes formula is:

$$P(M_r/H_r) = \sum_{t\in\Omega} P(M_r/H_r \& (P_{1r}, P_{2r}, M_{1r}, M_{2r}) = t) * P((P_{1r}, P_{2r}, M_{1r}, M_{2r}) = t)$$

Deriving $P(M_r/H_r \& (P_{1r},P_{2r},M_{1r},A_{2r})=t)$ $M_r=(e_{1r},e_{2r},p_{1r},p_{2r},m_{1e},m_{2r})$ is a given measurement on this SNP.

$T=(E_{1r},E_{2r},P_{1r},P_{2r},M_{1r},M_{2r})$ is the supposed "true" value, for $t=(P_{1r},P_{2r},M_{1r},M_{2r})$ and $(E_{1r},E_{2r})$ fixed from T by hypothesis. ($\Sigma_{1r}$ is one of $P_{1r},P_{2r}$, $E_{2r}$ is one of $M_{1r},M_{2r}$)

$$P(M_r=(e_{1r},e_{2r},p_{1r},p_{2r},m_{1r},m_{2r})/T=(E_{1r},E_{2r},P_{r1},P_{2r},M_{1r},M_{2r}))=P(e_{1r}/E_{1r})*P(e_{2r}/E_{2r})*P(p_{1r}/P_{r1})*P(p_{2r}/P_{2r})*P(m_{1r}/M_{1r})*P(m_{2r}/M_{2r})$$

Given:
$p_{eri}$=P(accurately measuring the embryo value i, on SNP r)
$p_{pri}$=P(accurately measuring the father value i, on SNP r)
$p_{mri}$=P(accurately measuring the mother value i, on SNP r)

$$P(e_{1r}/E_{1r}) = \begin{cases} p_{er1} & e_{1r} = E_{1r} \\ (1-p_{er1})*p(e_{1r}, E_{1r}, r) & e_{1r} \neq E_{1r} \end{cases}$$
$$= I_{e_{1r}=E_{1r}} * p_{er1} + I_{e_{1r}\neq E_{1r}} * (1-p_{pr1}) * p(e_{1r}, E_{1r}, r)$$
$$= F(e_{1r}, E_{1r}, p_{er1}, r)$$

where $p(e_{1r},E_{1r},r)=1/3$ if there is no measurement bias, otherwise it can be determined from experimental data, such as data from the Hapmap project.

Deriving $P((P_{1r},P_{2r},M_{1r},M_{2r})=t)$

For $t=(t_1,t_2,t_3,t_4)$:

$$P((P_{1r},P_{2r},M_{1r},M_{2r})=(t_1,t_2,t_3,t_4))=P(P_{1r}=t_1)*P(P_{2r}=t_2)*P(M_{1r}=t_3)*P(M_{2r}=t_4)$$

Suppose there are n samples of $(P_1,P_2,M_1,M_2)$, all paternal and maternal values are assumed to be independent, and $t=(t_1,t_2,t_3,t_4)$ for $t_1$ in $\{A,C,T,G\}$ To get a particular $p_{1A}=P(P_1=t_1)$, for $t_1=A$, assume that in absence of any data this probability could be anything between 0 and 1, so it is assigned a value of U(0,1). With the acquisition of data, this is updated with the new values and the distribution of this parameter becomes a beta distribution. Suppose that out of n observations of P1, there are h values P1=A, and w=(event $P_1$=A) and D=(data given). It is described in a prior section the form of the beta distribution $B(\alpha,\beta)$ with $\alpha$=h+1, $\beta$=n−h+1 for p(w|Data) (see equation (8)). The expected value and variance of $X\sim B(\alpha,\beta)$ distribution are:

$$EX = \frac{\alpha}{\alpha + \beta}$$

$$VX = \frac{\alpha\beta}{(\alpha + \beta)^2 + (\alpha + \beta + 1)}$$

So the posterior mean value of the parameter $p_{1rA}$=P$(P_{1r}$=A|Data)=(h+1)/(n+2) Similarly $p_{1rB}$=(#($p_{1r}$=B)+1)/(n+2), ... $m_{2rG}$=(#($m_{2r}$=G)+1)/(n+2), etc. Thus all the values $p_{1rA}, \ldots, m_{2rG}$ have been derived and:

$$P((P_{1r},P_{2r},M_{1r},M_{2r})=(t_1,t_2,t_3,t_4))=p_{1rt_1}*p_{2rt_2}*m_{1rt_3}*m_{2rt_4}$$

Deriving P(H)

The probability of the hypothesis $H=(H_1, \ldots, H_k)$ with $H_i=(p_i^*,m_i^*)$ depends on the amount of chromosome crossover. For example, with P(crossover)=0 then P(H)=1/4 and H=(p*,m*) if p* in $\{(p11, p21, \ldots, ps1), (p12, p22, \ldots, ps2)$, m* in $((m11, m21, \ldots, m21), (m12, m22, \ldots, m22)\}$, 0 otherwise with P(crossover)>0 it is important to incorporate the probability of crossover between each SNP.

Hypothesis H consists of the hypothesis for paternal and maternal chromosomes for each SNP, $p_i^* \in \{p_{1i},P_{2i}\}$ and $m_i^* \in \{m_{1i},m_{2i}\}$, i.e. $H=(H_p,H_m)$ where $H_p=(p_1^*, \ldots p_k^*)$, and $H_m=(m_1^*, \ldots m_k^*)$, which are independent.

$P(H)=P(H_p)*P(H_m)$. Suppose that SNP are ordered by increasing location, $$P(H_p) = \frac{1}{4}\prod_{i=2}^{k}(PC_i*(1-I_i)+(1-PC_i)*I_i)$$

where $PC_i$=P(crossover($r_{i-1},r_i$)) i.e. probability of crossover somewhere between SNPs $r_{i-1},r_i$, and $I_i$=1 if $p_i^*,p_{i-1}^*$ are coming both from $p_1$ or $p_2$, and it is 0 otherwise.

Deriving P(Crossover(a,b))

Given SNPs a,b, at base locations $l_a,l_b$ (given in bases), the probability of crossover is approximated as $P(l_a,l_b)$=0.5 $(1-\exp(-2G(l_a,l_b)))$ where $G(l_a,l_b)$=genetic distance in Morgans between locations $l_a,l_b$. There is no precise closed form function for G but it is loosely estimated as $G(l_a,l_b)$=$|l_a-l_b|*1e^{-8}$. A better approximation can be used by taking advantage of the HapMap database of base locations $s_i$, and distances $G(s_i,s_{i+1})$, for i spanning over all locations. In particular, $$G(l_a, l_b) = \sum_{l_a \leq s_i < l_b} G(s_i, s_{i+1}),$$

so it can be used in crossover probability.

Deriving P(M)

Once P(M|H) is known, P(H) can be found for all the different H in $S_H$, $$P(M) = \sum_{H \in S_H} P(M \mid H) P(H)$$

A More Expedient Method to Derive the Hypothesis of Maximal Probability

Given the limitation of computer time, and the exponential scaling of complexity of the above method as the number of SNPs increases, in some cases it may be necessary to use more expedient methods to determine the hypothesis of maximal probability, and thus make the relevant SNP calls. A more rapid way to accomplish this follows:

From before: P(H|M)=P(M|H)*P(H)/P(M), argmax$_H$P(H|M)=argmax$_H$ and P(M|H)*P(H)=argmax$_H$F(M,H), and the object is to find H, maximizing F(M,H).

Suppose M(s,k)=measurement on snips s to k, $H_{(s,k)}$=hypothesis on snips s to k, and for shorts $M_{(k,k)}$=$M_k$, $H_{(k,k)}$=$H_k$=measurement and hypothesis on snip k. As shown before:

$$P(M_{(1,k)} \mid H_{(1,k)}) = \prod_{i=1}^{k} P(M_i \mid H_i)$$

$$= P(M_k \mid H_k) * \prod_{i=1}^{k-1} P(M_i \mid H_i)$$

$$= P(M_k \mid H_k) * P(M_{(1,k-1)} \mid H_{(1,k-1)})$$

and also $$P(H_{(1,k)}) = 1/4 * \prod_{i=2}^{k} PF(H_{i-1}, H_i)$$

$$= PF(H_{k-1}, H_k) * 1/4 * \prod_{i=2}^{k-1} PF(H_{i-1}, H_i)$$

$$= PF(H_{k-1}, H_k) * P(H_{(1,k-1)})$$

where $$PF(H_{i-1}, H_i) = \begin{cases} 1 - PC(H_{i-1}, H_i) & H_{i-1} = H_i \\ PC(H_{i-1}, H_i) & H_{i-1} \neq H_i \end{cases}$$

and $PC(H_{i-1}, H_i)$=probability of crossover between $H_{i-1}$, $H_i$
So finally, for n snips:

$$F(M, H) = P(M \mid H) * P(H)$$

$$= P(M_{(1,n)} \mid H_{(1,n)}) * P(H_{(1,n)})$$

$$= P(M_{(1,n-1)} \mid H_{(1,n-1)}) * P(H_{(1,n-1)}) * P(M_n \mid H_n) * PF(H_{n-1}, H_n)$$

therefore: F(M,H)=F($M_{(1,n)}$,$H_{(1,n)}$))=F($M_{(1,n-1)}$,$H_{(1,n-1)}$)*P($M_n$|$H_n$)*PF($H_{(n-1)}$,$H_{(n-1)}$)

Thus, it is possible to reduce the calculation on n snips to the calculation on n−1 snips.

For H=($H_1, \ldots H_n$) hypothesis on n snips:

$$\max_H F(M, H) = \max_{(H_{(1,n1)}, H_n)} F(M, (H_{(1,n-1)}, H_n))$$

$$= \max_{H_n} \max_{H_{(1,n-1)}} F(M, (H_{(1,n-1)}, H_n))$$

$$= \max_{H_n} G(M_{(1,n)}, H_n)$$

where $$G(M_{(1,n)}, H_n) = \max_{H_{(1,n-1)}} F(M_{(1,n)}, (H_{(1,n-1)}, H_n))$$

$$= \max_{H_{(1,n-1)}} F(M_{(1,n-1)}, H_{(1,n-1)}) * P(M_n \mid H_n) * PF(H_{n-1}, H_n)$$

$$= P(M_n \mid H_n) * \max_{H_{(1,n-1)}} F(M_{(1,n-1)}, H_{(1,n-1)}) * PF(H_{n-1}, H_n)$$

$$= P(M_n \mid H_n) * \max_{H_{n-1}} \max_{H_{(1,n-2)}} F(M_{(1,n-1)}, (H_{(1,n-2)}, H_{n-1})) * PF(H_{n-1}, H_n)$$

$$= P(M_n \mid H_n) * \max_{H_{n-1}} PF(H_{n-1}, H_n) * G(M_{(1,n-1)}, H_{n-})$$

In summary:

$$\max_H F(M, H) = \max_{H_n} G(M_{(1,n)}, H_n)$$

where G can be found recursively: for i=2, ... n $$G(M_{(1,n)}, H_n) = P(M_n \mid H_n) * \max_{H_{n-1}} \lfloor PF(H_{n-1}, H_n) * G(M_{(1,n-1)}, H_{n-1}) \rfloor$$

and $G(M_{(1,1)}, H_1) = 0.25 * P(M_1 \mid H_1)$.

The best hypothesis can be found by following the following algorithm:
Step 1: For I=1, generate 4 hypotheses for $H_1$, make G($M_1$|$H_1$) for each of these, and remember $G_1, G_2, G_3, G_4$
Step 2: For I=2: generate 4 hypotheses for $H_2$, make G($M_{(1,2)}$|$H_2$) using the above formula:

$$G(M_{(1,2)}, H_2) = P(M_2 \mid H_2) * \max_{H_1} [PF(H_1, H_2) * G(M_1, H_1)],$$

remember these new four $G_n$.
Repeat step 2 for I=k with $k_i = k_{i-1}+1$ until k=n: generate 4 hypothesis for $H_k$, make G($M_{(1,k)}$|$H_k$)

$$G(M_{(1,k)}, H_k) = P(M_k \mid H_k) * \max_{H_{k-1}} \lfloor PF(H_{k-1}, H_k) * G(M_{(1,k-1)}, H_{k-1}) \rfloor$$

and remember these four $G_n$.
Since there are only four hypotheses to remember at any time, and a constant number of operations, the algorithm is linear.
To find P(M): P(H|M)=P(M|H)*P(H)/P(M)=F(M,H)/P(M))
As above:

$$P(M) = P(M_{(1,k)})$$

$$= \sum_{H_{(1,k)}} P(M_{(1,k)} \mid H_{(1,k)}) * P(H_{(1,k)})$$

$$= \sum_{H_k} P(M_K \mid H_k) \sum_{H_{(1,k-1)}} P(M_{(1,k-1)} \mid H_{(1,k-1)}) * P(H_{(1,k-1)}) * PF(H_{k-1}, H_k)$$

$$= \sum_{H_k} P(M_K \mid H_k) * W(M_{(1,k-1)} \mid H_k)$$

-continued where $W(M_{(1,k-1)} | H_k) =$ $$\sum_{H_{(1,k-1)}} P(M_{(1,k-1)} | H_{(1,k-1)}) * P(H_{(1,k-1)}) * PF(H_{k-1}, H_k)$$

W(M,H) can be solved by using recursion:

$$W(M_{(1,k-1)} | H_k) = \sum_{H_{(1,k-1)}} P(M_{(1,k-1)} | H_{(1,k-1)}) * P(H_{(1,k-1)}) *$$

$$PF(H_{k-1}, H_k)$$

$$= \sum_{H_{k-1}} P(M_{k-1} | H_{k-1}) \sum_{H_{(1,k-2)}} P(M_{(1,k-2)} | H_{(1,k-2)}) *$$

$$P(H_{(1,k-2)}) * PF(H_{k-2}, H_{k-1}) * PF(H_{k-1}, H_k)$$

$$= \sum_{H_{k-1}} P(M_{k-1} | H_{k-1}) * PF(H_{k-1}, H_k) *$$

$$W(M_{(1,k-2)} | H_{k-1})$$

Therefore:
$W(M_{(1,k-1)} | H_k) =$ $$\sum_{H_{k-1}} P(M_{k-1} | H_{k-1}) * PF(H_{k-1}, H_k) * W(M_{(1,k-2)} | H_{k-1})$$

and $W(M_{(1,1)} | H_2) = \sum_{H_1} P(M_1 | H_1) * 0.25 * PF(H_1 | H_2)$

The algorithm is similar to the case above, where i=2:n and in each step a new set of W(i) are generated until the final step yields the optimized W.

Deriving the $p_1$, $p_2$, $pp_1$, $pp_2$ Values from $d_1$, $d_2$, h, $pd_1$, $pd_2$, ph For the purpose of explanation, this section will focus on the paternal diploid and haploid data, but it is important to note that maternal data can be treated similarly. Let:

$d_1$, $d_2$—allele calls on the diploid measurements
h—allele call on the haploid measurement
$p_{d1}$, $p_{d2}$—probabilities of a correct allele call on the each of the diploid measurements
ph—probability of a correct allele call on the haploid measurement These data should be mapped to the following input parameters for disclosed algorithm:

pt—allele corresponding to haploid cell and one of the diploid cells
$p_2$—allele corresponding to the remaining diploid cell
$p_{p1}$, $p_{p2}$—probabilities of correct allele call Since h corresponds to $d_1$, then to find the value of $p_1$ it is necessary to use h and $d_1$. Then $p_2$ will automatically correspond to $d_2$. Similarly, if h corresponds to $d_2$, then to find the value of $p_1$ it is necessary to use h and $d_2$, and then $p_2$ will correspond to $d_1$.

The term "correspond" is used since it can mean either "be equal" or "originate with higher probability from" depending on different measurement outcomes and population frequency.

The goal of the algorithm is to calculate probabilities of "true" allele values hidden beyond results of raw measurement h, $d_1$, $d_2$, ph, $p_{d1}$, $p_{d2}$ and population frequencies.

The basic algorithm steps are the following:
(i) determine whether h corresponds to $d_1$ or $d_2$ based on h, $d_1$, $d_2$, ph, $p_{d1}$, $p_{d2}$ values and the population frequency data
(ii) assign the allele calls to $p_1$ and $p_2$; calculate the probabilities $p_{p1}$ and $p_{p2}$ based on step (1)

Assigning h to $d_1$ or $d_2$
Establish two hypotheses:
$H_1$: h corresponds to $d_1$ (h originates from $d_1$)
$H_2$: h corresponds to $d_2$ (h originates from $d_2$)
The task is to calculate probabilities of these two hypotheses given the measurement M:

$$P(H_1/M(h,d_1,d_2,p_h,p_{d1},p_{d2})) \text{ and } P(H_2/M(h,d_1,d_2,p_h,p_{d1},p_{d2}))$$

(To simplify the text, these will be referred to as $P(H_1/M)$ and $P(H_2/M)$) hereafter.

In order to calculate these probabilities, apply the Bayesian rule:

$$P(H_1 | M) = \frac{P(M | H_1) * P(H_1)}{P(M)}; P(H_2 | M) = \frac{P(M | H_2) * P(H_2)}{P(M)},$$

where $P(M)=P(M/H_1)*P(H_1)+P(M/H_2)*P(H_2)$. Since hypotheses H1 and H2 are equally likely, $P(H_1)=P(H_2)=0.5$, therefore:

$$P(H_1 | M) = \frac{P(M | H_1)}{P(M | H_1) + P(M | H_2)} \text{ and}$$

$$P(H_2 | M) = \frac{P(M | H_2)}{P(M | H_1) + P(M | H_2)}$$

In order to calculate $P(M/H_1)$ and $P(M/H_2)$, one must consider the set of all possible values of diploid outcomes $d_1$ and $d_2$, $\Omega=\{AA, AC, \ldots, GG\}$, i.e. any combination of A,C,T,G, so called underlying states. When the hypotheses are applied to the underlying states (i.e. accompany the assumed value of h based on hypothesis $H_1$ or $H_2$, to values $d_1$ and $d_2$), the following tables of all possible combinations (states $S=\{s_1, s_2, \ldots, s_6\}$) of "true values" H, $D_1$ and $D_2$ for h, $d_1$ and $d_2$, can be generated, respectively. These are listed here:

| Hypothesis $H_1$: $h = d_1$ | $\Omega$ = {AA, AC, ..., GG} | | | Hypothesis $H_2$: $h = d_2$ | $\Omega$ = {AA, AC, ... GG} | | |
|---|---|---|---|---|---|---|---|
| state | H | $D_1$ | $D_2$ | state | H | $D_1$ | $D_2$ |
| $s_1$ | A | A | A | $s_1$ | A | A | A |
| $s_2$ | A | A | C | $s_2$ | C | A | C |
| $s_3$ | A | A | T | $s_3$ | T | A | T |
| $s_4$ | A | A | G | $s_4$ | G | A | G |
| $s_5$ | C | C | A | $s_5$ | A | C | A |
| $s_6$ | C | C | C | $s_6$ | C | C | C |
| $s_7$ | C | C | T | $s_7$ | T | C | T |
| $s_8$ | C | C | G | $s_8$ | G | C | G |
| $s_9$ | T | T | A | $s_9$ | A | T | A |
| $s_{10}$ | T | T | C | $s_{10}$ | C | T | C |
| $s_{11}$ | T | T | T | $s_{11}$ | T | T | T |
| $s_{12}$ | T | T | G | $s_{12}$ | G | T | G |
| $s_{13}$ | G | G | A | $s_{13}$ | A | G | A |
| $s_{14}$ | G | G | C | $s_{14}$ | C | G | C |
| $s_{15}$ | G | G | T | $s_{15}$ | T | G | T |
| $s_{16}$ | G | G | G | $s_{16}$ | G | G | G |

Since the "true values" H, $D_1$ and $D_2$ are unknown, and only the raw measurement outcomes h, $d_1$, $d_2$, $p_h$, $p_{d1}$, $p_{d2}$ are known, the calculation of the $P(M/H_1)$ and $P(M/H_2)$ over the entire set $\Omega$ must be performed in the following manner:

$$P(M \mid H_1) = \sum_{(D_1, D_2) \in \Omega} P(M(h, d_1, d_2) \mid H_1 \& D_1, D_2) * P(D_1, D_2)$$

$$P(M \mid H_2) = \sum_{(D_1, D_2) \in \Omega} P(M(h, d_1, d_2) \mid H_2 \& D_1, D_2) * P(D_1, D_2)$$

If, for the purpose of the calculation, one assumes that $d_1$ and $d_2$, as well as $p_{d1}$ and $p_{d2}$ are independent variables, it can be shown that:

$$P(M \mid H_1) = \sum_{\Omega} P(M(h, d_1, d_2) \mid H_1 \& D_1, D_2) * P(D_1, D_2)$$

$$= \sum_{S} P(M(h) \mid H) * P(M(d_1) \mid D_1) * P(M(d_2) \mid D_2) *$$

$$P(D_1) * P(D_2)$$

Consider the first three terms under the last sum above: $P(M(x)/X)$, for x in $\{h, d_1, d_2\}$.

The calculation of the probability of correct allele call (hitting the "true allele value") is based on measurement of outcome x given the true value of allele X. If the measured value x and the true value X are equal, that probability is $p_x$ (the probability of correct measurement). If x and X are different, that probability is $(1-p_x)3$. For example, calculate the probability that the "true value" C is found under the conditions that X=C, and the measured value is x=A. The probability of getting A is $p_x$. The probability of getting C, T or G is $(1-p_x)$. So, the probability of hitting C is $(1-p_x)/3$, since one can assume that C, T and G are equally likely.

If the indicator variable $I_x$ is included in the calculation, where $I_x=1$ if x=X and $I_x=0$ if x≠X, the probabilities are as follows:

$$P(M(x)/X) = I_{\{x=x\}} * p_x + (1 - I_{\{x=x\}}) * (1/3) * (1-p_x), x \text{ in } \{h, d_1, d_2\}$$

Now consider the last two terms in $P(M|H_1)$. $P(D_1)$ and $P(D_2)$ are population frequencies of alleles A, C, T and G, that may be known from prior knowledge.

Consider the expression shown above for a particular state $s_2$, given the particular measurement $M(h=A, d_1=G, d_2=C)$:

$$P(M(h) \mid H) * P(M(d_1) \mid D_1) * P(M(d_2) \mid D_2) * P(D_1) * P(D_2) ==$$

$$P(M(h) = A \mid H = A) * P(M(d_1) = G \mid D_1 = A) *$$

$$P(M(d_2) = C \mid D_2 = C) * P(D_1 = A) * P(D_2 = C) ==$$

$$p_h * ((1 - p_{d1})/3) * p_{d2} * f(D_1 = A) * f(D_2 = C)$$

Similarly, calculate (1) given the particular measurement (in this case $M(h=A, d_1=G, d_2=C)$) for remaining 15 states and sum over the set Q.

Now $P(M/H_1)$ and $P(M/H_2)$ have been calculated. Finally, calculate $P(H_1/M)$ and $P(H_1/M)$ as described before:

$$P(H_1 \mid M) = \frac{P(M \mid H_1)}{P(M \mid H_1) + P(M \mid H_2)}$$

$$P(H_2 \mid M) = \frac{P(M \mid H_2)}{P(M \mid H_1) + P(M \mid H_2)}$$

Assigning the Allele Calls and Corresponding Probabilities

Now establish four different hypotheses:
$H_{p2A}$: "true value" of $p_2$ is A
$H_{p2C}$: "true value" of $p_2$ is C
$H_{p2T}$: "true value" of $p_2$ is T
$H_{p2G}$: "true value" of $p_2$ is G
and calculate $P(H_{p2A}/M)$, $P(H_{p2C}/M)$, $P(H_{p2T}/M)$, $P(H_{p2G}/M)$. The highest value determines the particular allele call and corresponding probability.

Since the origin of $p_2$ is unknown (it is derived from $d_1$ with probability of $P(H_2/M)$ and from $d_2$ with probability $P(H_1/M)$), one must consider both cases that $p_2$ allele originates from $d_1$ or $d_2$. For Hypothesis HA, applying Bayes rule, give:

$$P(H_{p2A}|M) = P(H_{p2A}|M, H_1) * P(H_1|M) + P(H_{p2A}|M, H_2) * P(H_2|M)$$

$P(H_1/M)$ and $P(H_2/M)$ have already been determined in step 1. By Bayes rule:

$$P(H_{p2A} \mid H_1, M) = \frac{P(M \mid H_1, H_{p2A}) * P(H_1, H_{p2A})}{P(H_1 \mid M)}$$

Since $H_1$ implies that $p_2$ originates from $d_2$:

$$P(M|H_1, H_{p2A}) = P(M(d_2)|D_2 = A) = I_{\{d2=D2\}} * P_{d2} + (1 - I_{\{d2=D2\}}) * (1-p_{d2})/3$$

$P(H_1, M/H_{p2A}) = P(M(d_2)/D_2=A) = I_{\{d2=D2\}} * p_{d2} + (1 - I_{\{d2=D2\}}) * (1/3) * (1-p_{d2})$, as described before.

$P(H_{p2A}) = P(D_2 = A) = f_{d2}(A)$, where $f_{d2}(A)$ is obtained from population frequency data.

$P(H_1, M) = P(H_1, M/H_{p2A}) * P(H_{p2A}) + P(H_1, M/H_{p2C}) * P(H_{p2C}) + P(H_1, M/H_{p2T}) * P(H_{p2T}) + P(H_1, M/H_{p2G}) * P(H_{p2G})$.

Similarly, calculate $P(H_{p2A} \& H_2/M)$.

$P(H_{p2A}/M) = P(H_{p2A} \& H_1/M) + P(H_{p2A} \& H_2/M)$, therefore the probability that $p_2$ is equal to A has been calculated. Repeat the calculation for C, T, and G. The highest value will give the answer of $p_2$ allele call and the corresponding probability.

Assigning the Allele Call to $p_1$ (Allele Corresponding to the Haploid Cell and One of the Diploid Cells)

As before, we establish four different hypotheses:
$H_{p1A}$: "true value" of $p_1$ is A
$H_{p1C}$: "true value" of $p_1$ is C
$H_{p1T}$: "true value" of $p_1$ is T
$H_{p1C}$: "true value" of $p_1$ is G
and calculate $P(H_{p1A}/M)$, $P(H_{p1C}/M)$, $P(H_{p1T}/M)$, $P(H_{p1G}/M)$ Here is an elaboration of $H_{p1A}$. In the "true case" case, $p_1$ will be equal to A only if the haploid and the corresponding diploid cell are equal to A. Therefore, in order to calculate $p_1$ and $p_{p1}$ one must consider situations where haploid and corresponding diploid cell are equal. So, the hypothesis $H_{p1A}$: the "true value" of $p_1$ is A and becomes $H_{hd4}$: the "true value" of the haploid cell and corresponding diploid cell is A.

Since the origin of h is unknown (it is derived from $d_1$ with probability of $P(H_1/M)$ and from $d_2$ with probability $P(H_2/M)$), one must consider both cases, that h allele originates from $d_1$ or $d_2$, and implement that in determination of $p_1$. That means, using Bayes rule:

$P(H_{hdA}|M) = P(H_{hdA}|M,H_1) * P(H_1|M) + P(H_{hdA}|M,H_2) * P(H_2|M)$

As before, $P(H_1/M)$ and $P(H_2/M)$ are known from previous calculations.

$$P(H_{hdA}|H_1, M) = \frac{P(H_1, M|H_{hdA}) * P(H_{hdA})}{P(H_1|M)}$$

$$P(H_1, M/H_{hdA}) = P(M(h)/H = A) * P(M(d_1)/D_1 = A)$$
$$= [I_{\{h=H\}} * p_h + (1 - I_{\{h=H\}}) * (1/3) * (1 - p_h)] *$$
$$[I_{\{d1=D1\}} * p_{d1} + (1 - I_{\{d1=D1\}}) * (1/3) * (1 - p_{d1})],$$

since H1 implies that $p_1$ originates from $d_1$. $P(H_{hdA}) = P(h=A) * P(D_1=A) = f_h(A) * f_{d1}(A)$, where $f_h(A)$ and $f_{d2}(A)$ are obtained from population frequency data. $P(H_1,M) = P(H_1, M/H_{hdA})) * P(H_{hdA}) + P(H_1, M/H_{hdC}) + *P(H_{hdC}) + P(H_1, M/H_{hdT}) * P(H_{hdT}) + P(H_1, M/H_{hdG}) * P(H_{hdG})$ Similarly, calculate $P(H_{hdA} \& H_2/M)$. $P(H_{hdA}/M) = P(H_{hdA} \& H_1/M) + P(H_{hdA} \& H_2/M)$ and now we have calculated the probability that $p_1$ is equal to A. Repeat the calculation for C, T, and G. The highest value will give the answer of $p_1$ allele call and corresponding probability.

Example Input

Two input examples are shown. The first example is of a set of SNPs with a low tendency to cosegregate, that is, SNPs spread throughout a chromosome, and the input data is shown in FIG. 21. The second example is of a set of SNPs with a high tendency to cosegregate, that is SNPs clustered on a chromosome, and the input data is shown in FIG. 22. Both sets of data include an individual's measured SNP data, the individual's parents SNP data, and the corresponding confidence values. Note that this data is actual data measured from actual people. Each row represent measurements for one particular SNP location. The columns contain the data denoted by the column header. The key to the abbreviations in the column headers is as follows:

family_id=the unique id for each person (included for clerical reasons)
    snp_id=the SNP identification number
    e1, e2=the SNP nucleotide values for the embryo
    p1, p2=the SNP nucleotide values for the father
    m1, m2=the SNP nucleotide values for the mother
    pe1, pe2=the measurement accuracy for e1,e2
    pp1, pp2=the measurement accuracy for p1,p2
    pm1, pm2=the measurement accuracy for m1,m2

Example Output

The two examples of output data are shown in FIG. 23 and FIG. 24, and correspond to the output data from the data given in FIG. 21 and FIG. 22 respectively. Both figures show an individual's measured SNP data, the individual's parents SNP data, the most likely true value of the individual's SNP data, and the corresponding confidences. Each row represents the data corresponding to one particular SNP. The columns contain the data denoted by the column header. The key to the abbreviations in the column headers is as follows:

snp_id=the SNP identification number
    true_value=the proposed nucleotide value for e1,e2
    true_hyp=the hypothesis for the origin of e1,e2
    ee=the measured SNP nucleotide values for e1,e2
    pp=the measured SNP nucleotide values for p1,p2
    mm=the measured SNP nucleotide values for m1,m2
    HypProb=the probability of the final hypothesis. There is only one number for the output, but due to the excel column structure, this number is replicated in all rows.

Note that this algorithm can be implemented manually, or by a computer. FIG. 21 and FIG. 22 show examples of input data for a computer implemented version of the method. FIG. 23 shows the output data for the input data shown in FIG. 21. FIG. 24 shows the output data for the input data shown in FIG. 22.

Simulation Algorithm

Figure 18:
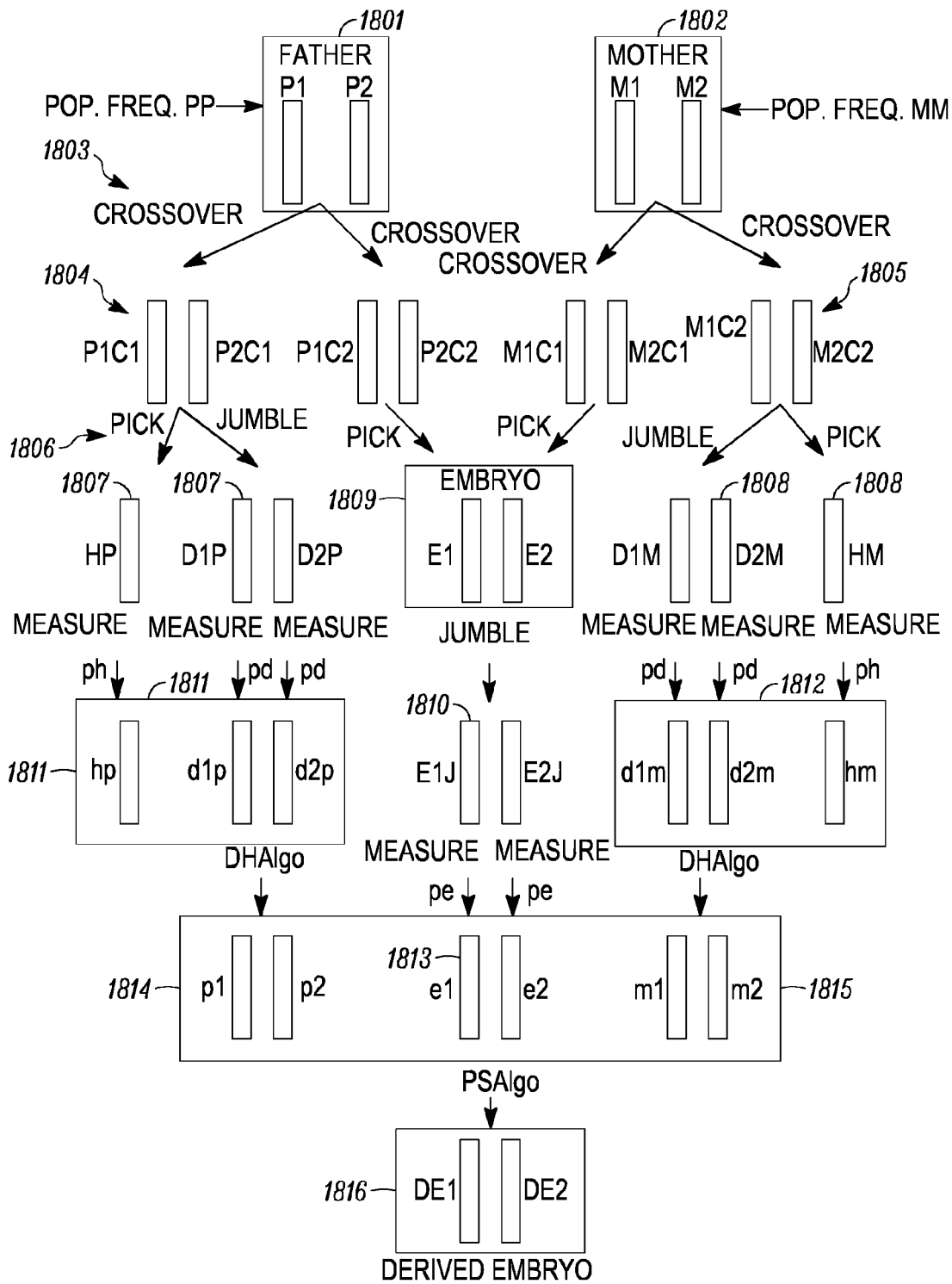
FIG. 18: a visual representation of the flow chart describing the algorithm used to demonstrate the effectiveness of the cleaning algorithm on simulated data.

Below is a second simulation which was done to ensure the integrity of the system, and to assess the actual efficacy of the algorithm in a wider variety of situations. In order to do this, 10,000 full system simulations were run. This involves randomly creating parental genetic data, emulating meiosis in silico to generate embryonic data, simulating incomplete measurement of the embryonic data, and then running the method disclosed herein to clean the simulated measured embryonic data, and then comparing the simulated cleaned data with the simulated real data. A more detailed explanation of the simulation is given below, and the visual representation of the flow of events is given in FIG. 18. Two different implementations of the theory were tested. A fuller explanation is given below.

Simulation Algorithms for DH and PS and Results

For both algorithms, the initial input variables are:
    (i) the list of SNPs to test,
    (ii) the population frequency of the maternal (popfreqlistMM) and paternal (popfreqlistPP) chromosomes,
    (iii) the probabilities of a correct allele call for haploid measurement (ph,pe), and for unordered diploid measurements (pd).

These values should be fixed based on the results from empirical data (population frequency) on relevant SNPs, and from measuring instrumentation performance (ph,pd,pe). The simulation was run for several scenarios such as most likely (informed), uniform (uninformed) and very unlikely (extreme case).

Once the above static parameters are fixed, crossover probabilities given the particular SNPs are the same for all the simulations, and will be derived ahead of the time given the databases for snip location(SNIPLOC_NAME_MAT) and genetic distance (HAPLOC_NAME_MAT).

[crossprob,snips]=GetCrossProb(snips,SNIPLOC_
      NAME_MAT,parameters,HAPLOC_NAME_
      MAT);

Preliminary Simulation Loop

The preliminary simulation loop is to demonstrate that the genetic data that will be used for the full simulation is realistic. Steps 1 through 5 were repeated 10,000 times. Note that this simulation can be run for either or both parents; the steps are identical. In this case, the simulation will be run for the paternal case for the purposes of illustration, and the references to FIG. 18 will also include the corresponding maternal entry in FIG. 18 in parentheses. This simulation was also run using Matlab.

Step 1: Generate Original Parental Diploid Cells (P1,P2).
    [P1,P2]=GenerateOriginalChromosomes(snips,popfreqlistPP); 1801 (1802)

Generate original paternal cells depending on the population frequency for each SNP for father cells.

Step 2: Generate Haploid and Unordered Diploid Data for DHAlgo

Simulate crossover of the parental chromosomes 1803 to give two sets of chromosomes, crossed over: P1C1, P2C1 and P1C2, P2C2; 1804 (1805). Pick one of the father alleles after the crossover 1806 (from the first set) for haploid allele HP 1807 (1808) in this case P1 (since there is no difference which one), and mix up the order in the diploid alleles to get (D1P,D2P) 1807 (1808).
    HP=PickOne(P1C1,P2C1),
    [D1P,D2P]=Jumble(P1,P2).
Step 3: Introduce Error to the Original Dataset in Order to Simulate Measurements
Based on given probabilities of correct measurement (ph-haploid, pd-diploid measurement), introduce error into the measurements to give the simulated measured parental data 1811 (1812).
    hp=MakeError(HP,ph);
    d1p=MakeError(D1P,pd);
    d2p=MakeError(D2P,pd).
Step 4: Apply DHAlgo to Get (p1,p2), (pp1,pp2)
    DHAlgo takes alleles from haploid cell and unordered alleles from diploid cell and returns the most likely ordered diploid alleles that gave rise to these. DHAlgo attempts to rebuild (P1,P2), also returns estimation error for father (pp1,pp2). For comparison, the empirical algorithm that does simple allele matching is also used. The goal is to compare how much better is the disclosed algorithm, compared to the simple empirical algorithm.
[p1,p2,pp1,pp2]=DHAlgo(hp,d1p,d2p,ph,pd,snips,popfreqlistPP,'DH'); [p1s,p2s,pp1s,pp2s]=DHAlgo(hp,d1p,d2p,ph,pd,snips,popfreqlistPP,'ST');
Step 5: Collect Statistics for the Run
    Compare (P1,P2) to derived (p1,p2).

$$[P1cmp(:,i), P2cmp(:,i), P1prob(:,i), P2prob(:,i), P1mn(i), P2mn(i)] = DH\text{SimValidate}(P1, P2, p1, p2, pp1, pp2);$$

Note: $(P1S_i, P2S_i, P1P_i, P2P_i, P1A_i, P2A_i) = (I_{\{P1=p1\}}, I_{\{P1=p2\}}, p_{p1}, p_{p2}, p1_{acc}, p2_{acc})$, where $I_{\{P1=p1\}}$ is binary indicator array for estimation of DH algorithm accuracy for all the SNPs, similarly, for $I_{\{P2=p2\}}$. $p_{p1}, p_{p2}$ are probabilities of a correct allele call derived from the algorithm, and $p1_{acc} = \text{mean}(I_{\{P1=p1\}})$, i.e. average accuracy for this run for p1, similar for $p2_{acc}$.
Preliminary Simulation Results
    Ten thousand simulations were used to estimate the algorithm accuracy DHAccuracy.P1=mean(P1A$_i$), DHAccuracy.P2=mean(P2A$_i$), which shows the overall accuracy of the DH algorithm from P1,P2. On an individual SNP basis, the average accuracy on each SNP SNPAcc.P1=mean(P1S$_i$) should agree with the average of the estimated probability of correctly measuring that SNP, SNPProb.P1=mean(P2P$_i$), i.e. if the algorithm works correctly, the value for SNPAcc.P1 should correspond closely to SNPProb.P1. The relationship between these two is reflected by their correlation.
    The 10000 loops of the simulation were run for different setup scenarios:
(1) The underlying population frequency was given by existing genotyping data which is more realistic, and uniform population frequencies where A,C,T,G have the same probability on each SNP.
(2) Several combinations for measurement accuracy for haploid and unordered diploid measurements (ph,pd). Varying assumptions were made; that the measurements are both very accurate (0.95, 0.95), less accurate (0.75, 0.75) and inaccurate or random (0.25, 0.25), as well as unbalanced combinations of (0.9, 0.5), (0.5, 0.9). What might be closest to reality may be accuracies of approximately 0.6 to 0.8.
(3) The simulation was run in all these cases for both the DHAlgorithm and simple matching STAlgorithm, in order to assess the performance of the disclosed algorithm.
The results of all these runs are summarized in FIG. 25.
    The disclosed algorithm performs better than the existing empirical algorithm in these simulations, especially for the realistic cases of non-uniform population frequency, and unbalanced or reduced probabilities of correct measurements. It has also been confirmed that our estimates of the algorithm accuracy for individual SNPs are very good in these cases, since the correlation between the estimated accuracy of correct allele call and simulation average accuracy is around 99%, with average ratio of 1.
    In the most realistic case, for data population frequency and (ph,pd)=(0.6, 0.8), the average percent of correctly retrieved SNPs for (P1,P2) is (0.852, 0.816) in implementation 1, and (0.601, 0.673 in implementation 2.
    Note that for FIG. 25 and FIG. 26 the rows beginning with "data" use population frequency data was taken from empirical results, while the rows beginning with "uniform" assume uniform populations.
    It is important to note that in FIG. 25 and FIG. 26 the accuracy is defined as the average percent of SNPs where the correct SNP call was made and the correct chromosome of origin was identified. It is also important to note that these simulations reflect two possible implementations of the algorithm. There may be other ways to implement the algorithm that may give better results. This simulation is only meant to demonstrate that the method can be reduced to practice.
Full Simulation Loop
    Steps 1-8 were repeated 10000 times. This is the simulation to test the full disclosed method to clean measured genetic data for a target individual using genetic data measured from related individuals, in this case, the parents. This simulation was run using Matlab.
Step 1: Generate Original Parental Diploid Cells (P1,P2), (M1,M2)
    [P1,P2]=GenerateOriginalChromosomes(snips,popfreqlistPP); (1801)
    [M1,M2]=GenerateOriginalChromosomes(snips,popfreqlistMM); (1802)
    Generate original parental cells depending on the population frequency for each SNP for mother and father cells.
Step 2: Crossover Parental Cells (P1C,P2C), (M1C,M2C) (1803)
    Generate two sets of paternal cells with crossovers: first to get (P1C1,P2C1) used in DHAlgo, and second time to get (P1C2,P2C2) used in PSAlgo. (1804)
    Generate two sets of maternal cells with crossovers: first to get (M1C1,M2C1) used in DHAlgo, and (M1C2,M2C2) used in PSAlgo. (1805)
    [P1C1,P2C1]=Cross(P1,P2,snips,fullprob);
    [P1C2,P2C2]=Cross(P1,P2,snips,fullprob);
    [M1C1,M2C1]=Cross(M1,M2,snips,fullprob);
    [M1C2,M2C2]=Cross(M1,M2,snips,fullprob);
Step 3 Make Haploid Cell and Unordered Diploid Cells for DHAlgo (1806)
    Pick one of the sets of paternal cells (1804, first set) for haploid cell HP, and mix up the order in the diploid cell to get (D1P,D2P) (1807). Do the same for mother cells (1805, first set) to get MH, (D1M,D2M). (1808).
    HP=PickOne(P1C1,P2C1);
    HM=PickOne(M1C1,M2C1);
    [D1P,D2P]=Jumble(P1,P2);
    [D1M,D2M]=Jumble(M1,M2);

Step 4: Make Diploid Embryo Cell (1809)

Pick one of the paternal cells (1804, second set) and one of the maternal cells (1805, second set) for embryo cell. Mix up the order for measurement purposes.

E1=PickOne(P1C2,P2C2);
E2=PickOne(M1C2,M2C2);
[E1J,E2J]=Jumble(E1,E2); (1810)

Step 5: Introduce Error to the Measurements (1811, 1812, 1813)

Based on given measurement error (ph-haploid cells, pd-unordered diploid cells, pe-embryo cells), introduce error into the measurements.

hp=MakeError(HP,ph); (1811)
d1p=MakeError(D1P,pd); (1811)
d2p=MakeError(D2P,pd); (1811)
hm=MakeError(HM,ph); (1812)
d1m=MakeError(D1M,pd); (1812)
d2m=MakeError(D2M,pd); (1812)
e1=MakeError(E1J,pe1); (1813)
e2=MakeError(E2J,pe2); (1813)

Step 6: Apply DHAlgo to Get $(p_1,p_2)$, $(m_1,m_2)$, $(pp1,pp_2)$, $(pm1,pm2)$

DHAlgo takes a haploid cell and an unordered diploid cell and returns the most likely ordered diploid cell that gave rise to these. DHAlgo attempts to rebuild (P1C1,P2C1) for father and (M1C1,M2C1) for mother chromosomes, also returns estimation error for father $(pp1,pp_2)$ and mother (pm1,pm2) cells.

[p1,p2,pp1,pp2]=DHAlgo(hp,d1p,d2p,snips,popfreqlistPP); (1814)
[m1,m2,pm1,pm2]=DHAlgo(hm,d1m,d2m,snips,popfreqlistMM); (1815)

Step 7: Apply PSAlgo to Get (DE1,DE2) (1816)

PSAlgo takes rebuilt parent cells (p1,p2,m1,m2) and unordered measured embryo cell (e1,e2) to return most likely ordered true embryo cell (DE1,DE2). PS Algo attempts to rebuild (E1,E2).

[DE1,DE2,alldata]=PSAlgo(snips,e1,e2,p1,p2,m1,m2,pe,pp1,pp2,pm1,pm2,parameters,crossprob,popfreqlistPP,popreqlistMM);

Step 8: Collect Desired Statistics from this Simulation Run

Get statistics for the run:
simdata=SimValidate(alldata,DE1,DE2,P1,P2,M1,M2,E1,E2,p1,p2,m1,m2,e1,e2,pe,pe,pp1,pp2,pm1,pm2);

Simulation Results

Ten thousand simulations were run and the final estimates for the algorithm accuracy PSAccuracy.E1=mean($E1A_i$), PSAccuracy.E2=mean($E2A_i$), which tells us the overall accuracy of the PS algorithm from E1,E2 were calculated. On an individual SNP basis, the average accuracy on each SNP SNPAcc.E1=mean($E1S_i$) should agree with the average of the estimated probability of correctly measuring that SNP, SNPProb.E1=mean($E2P_i$), i.e. if the algorithm is written correctly, then SNPAcc.E1 should be observed to correlate to SNPProb.E1. The relationship between these two is reflected by their correlation.

Ten thousand loops of the simulation have been run for different setup scenarios:

(1) Underlying population frequency given by existing genotyping data which is more realistic, and uniform population frequencies where A,C,T,G have the same probability on each SNP.

(2) Several combinations of measurement accuracy for haploid, unordered diploid and embryo measurements (ph,pd,pe). A variety of accuracies were simulated: very accurate (0.95, 0.95, 0.95), less accurate (0.75, 0.75, 0.75) and inaccurate or random (0.25, 0.25, 0.25), as well as unbalanced combinations of (0.9, 0.5, 0.5), (0.5, 0.9, 0.9). What may be closest to reality is approximately (0.6, 0.8, 0.8).

(3) We ran the simulation in all these cases for both our PSAlgorithm and simple matching STPSAlgorithm, in order to assess the performance of the disclosed algorithm.

The results of these runs are summarized in the FIG. 26.

The disclosed algorithm is performs better than the existing empirical algorithm in these simulations, especially for the realistic cases of non-uniform population frequency, and unbalanced or reduced probabilities of correct measurements. It has also been shown that the estimates of the algorithm accuracy for individual SNPs are very good in these cases, since the correlation between the estimated accuracy of correct allele call and simulation average accuracy is around 99%, with average ratio of 1.

In the most realistic case, for data population frequency and (ph, pd, pe)=(0.6, 0.8, 0.8), the average percent of correctly retrieved SNPs for (E1,E2) is (0.777, 0.788) in implementation 1 and (0.835, 0.828) in implementation 2. As mentioned above, the number denoting the average accuracy of algorithm refers not only to the correct SNP call, but also the identification of correct parental origin of the SNP. To be effective, an algorithm must return better results than the algorithm that simply accepts the data as it is measured. One might be surprised to see that in some cases, the accuracy of the algorithm is lower than the listed accuracy of measurement. It is important to remember that for the purposes of this simulation a SNP call is considered accurate only if it is both called correctly, and also its parent and chromosome of origin are correctly identified. The chance of getting this correct by chance is considerably lower than the measurement accuracy.

Laboratory Techniques

There are many techniques available allowing the isolation of cells and DNA fragments for genotyping. The system and method described here can be applied to any of these techniques, specifically those involving the isolation of fetal cells or DNA fragments from maternal blood, or blastocysts from embryos in the context of IVF. It can be equally applied to genomic data in silico, i.e. not directly measured from genetic material.

In one embodiment of the system, this data can be acquired as described below.

Isolation of Cells

Adult diploid cells can be obtained from bulk tissue or blood samples. Adult diploid single cells can be obtained from whole blood samples using FACS, or fluorescence activated cell sorting. Adult haploid single sperm cells can also be isolated from sperm sample using FACS. Adult haploid single egg cells can be isolated in the context of egg harvesting during IVF procedures.

Isolation of the target single blastocysts from human embryos can be done following techniques common in in vitro fertilization clinics. Isolation of target fetal cells in maternal blood can be accomplished using monoclonal antibodies, or other techniques such as FACS or density gradient centrifugation.

DNA extraction also might entail non-standard methods for this application. Literature reports comparing various methods for DNA extraction have found that in some cases novel protocols, such as the using the addition of N-lauroylsarcosine, were found to be more efficient and produce the fewest false positives.

Amplification of Genomic DNA

Amplification of the genome can be accomplished by multiple methods including: ligation-mediated PCR (LM-PCR), degenerate oligonucleotide primer PCR (DOP-PCR), and multiple displacement amplification (MDA). Of the three methods, DOP-PCR reliably produces large quantities of DNA from small quantities of DNA, including single copies of chromosomes; this method may be most appropriate for genotyping the parental diploid data, where data fidelity is critical. MDA is the fastest method, producing hundred-fold amplification of DNA in a few hours; this method may be most appropriate for genotyping embryonic cells, or in other situations where time is of the essence.

Background amplification is a problem for each of these methods, since each method would potentially amplify contaminating DNA. Very tiny quantities of contamination can irreversibly poison the assay and give false data. Therefore, it is critical to use clean laboratory conditions, wherein pre- and post-amplification workflows are completely, physically separated. Clean, contamination free workflows for DNA amplification are now routine in industrial molecular biology, and simply require careful attention to detail.

Genotyping Assay and Hybridization

The genotyping of the amplified DNA can be done by many methods including MOLECULAR INVERSION PROBES (MIPs) such as AFFMETRIX's GENFLEX Tag Array, microarrays such as AFFMETRIX's 500K array or the ILLUMINA Bead Arrays, or SNP genotyping assays such as APPLIED BIOSYSTEMS's TAQMAN assay. The AFFMETRIX 500K array, MIPs/GENFLEX, TAQMAN and ILLUMINA assay all require microgram quantities of DNA, so genotyping a single cell with either workflow would require some kind of amplification. Each of these techniques has various tradeoffs in terms of cost, quality of data, quantitative vs. qualitative data, customizability, time to complete the assay and the number of measurable SNPs, among others. An advantage of the 500K and ILLUMINA arrays are the large number of SNPs on which it can gather data, roughly 250,000, as opposed to MIPs which can detect on the order of 10,000 SNPs, and the TAQMAN assay which can detect even fewer. An advantage of the MIPs, TAQMAN and ILLUMINA assay over the 500K arrays is that they are inherently customizable, allowing the user to choose SNPs, whereas the 500K arrays do not permit such customization.

In the context of pre-implantation diagnosis during IVF, the inherent time limitations are significant; in this case it may be advantageous to sacrifice data quality for turn-around time. Although it has other clear advantages, the standard MIPs assay protocol is a relatively time-intensive process that typically takes 2.5 to three days to complete. In MIPs, annealing of probes to target DNA and post-amplification hybridization are particularly time-intensive, and any deviation from these times results in degradation in data quality. Probes anneal overnight (12-16 hours) to DNA sample. Post-amplification hybridization anneals to the arrays overnight (12-16 hours). A number of other steps before and after both annealing and amplification bring the total standard timeline of the protocol to 2.5 days. Optimization of the MIPs assay for speed could potentially reduce the process to fewer than 36 hours. Both the 500K arrays and the ILLUMINA assays have a faster turnaround: approximately 1.5 to two days to generate highly reliable data in the standard protocol. Both of these methods are optimizable, and it is estimated that the turn-around time for the genotyping assay for the 500 k array and/or the ILLUMINA assay could be reduced to less than 24 hours. Even faster is the TAQMAN assay which can be run in three hours. For all of these methods, the reduction in assay time will result in a reduction in data quality, however that is exactly what the disclosed invention is designed to address. Some available techniques that are faster are not particularly high-throughput, and therefore are not feasible for highly parallel prenatal genetic diagnosis at this time.

Naturally, in situations where the timing is critical, such as genotyping a blastocyst during IVF, the faster assays have a clear advantage over the slower assays, whereas in cases that do not have such time pressure, such as when genotyping the parental DNA before IVF has been initiated, other factors will predominate in choosing the appropriate method. For example, another tradeoff that exists from one technique to another is one of price versus data quality. It may make sense to use more expensive techniques that give high quality data for measurements that are more important, and less expensive techniques that give lower quality data for measurements where the fidelity is not critical. Any techniques which are developed to the point of allowing sufficiently rapid high-throughput genotyping could be used to genotype genetic material for use with this method.

Combinations of the Aspects of the Invention

As noted previously, given the benefit of this disclosure, there are more aspects and embodiments that may implement one or more of the systems, methods, and features, disclosed herein. Below is a short list of examples illustrating situations in which the various aspects of the disclosed invention can be combined in a plurality of ways. It is important to note that this list is not meant to be comprehensive; many other combinations of the aspects, methods, features and embodiments of this invention are possible.

Figure 19:
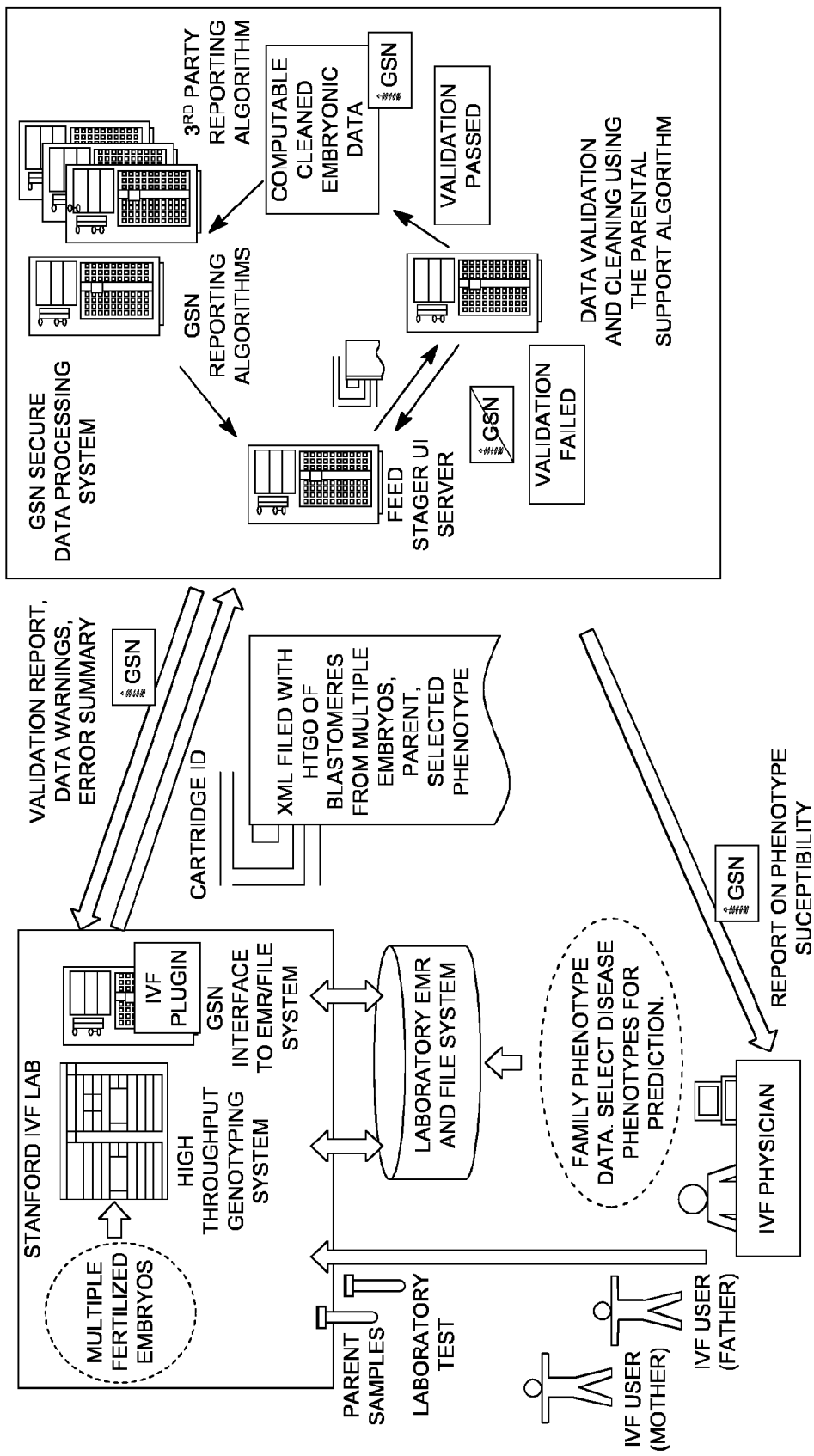
FIG. 19: an illustration of a system that is configured to accomplish the method disclosed herein, in the context of phenotype prediction of embryos during IVF.

One example is the system which may operate in an IVF laboratory (see FIG. 19) that would allow full genotyping of all viable embryos within the time constraints of the IVF procedure. This would require a turn-around time from egg fertilization to embryo implantation of under three days. This system may consist of parental genetic samples 1901 from IVF user (mother) 1902 and IVF user (father) 1903 being analyzed at IVF lab 1904 using a genotyping system. It may involve multiple eggs that are harvested from the mother 1902 and fertilized with sperm from the father 1903 to create multiple fertilized embryos 1905. It may involve a laboratory technician extracting a blastocyst for each embryo, amplifying the DNA of each blastocyst, and analyzing them using a high throughput genotyping system 1906. It may involve sending the genetic data from the parents and from the blastocyst to a secure data processing system 1907 which validates and cleans the embryonic genetic data. It may involve the cleaned embryonic data 1908 being operated on by a phenotyping algorithm 1909 to predict phenotype susceptibilities of each embryo. It may involve these predictions, along with relevant confidence levels, being sent to the physician 1910 who helps the IVF users 1902 and 1903 to select embryos for implantation in the mother 1901.

Another example could utilize a variety of genotyping measurement techniques in a way that would optimize the value of each. For example, a lab could use a technique that is expensive but can give high quality data in cases with low signal, such as APPLIED BIOSYSTEMS's TAQMAN assay, to measure the target DNA, and use a technique that is less expensive but requires a greater amount of genetic material to give good quality data, such as AFFMETRIX's 500K Genechip, or MIPs, to measure the parental DNA.

Another example could be a situation in which a couple undergoing IVF treatment have eggs harvested from the woman, and fertilized with sperm from the man, producing eight viable embryos. A blastocyst is harvested from each embryo, and the genomic data from the blastocysts are measured using TAQMAN Genotyping Assay. Meanwhile, the diploid data is measured from tissue taken from both parents using MOLECULAR INVERSION PROBES. Haploid data from one of the man's sperm, and one of the woman's eggs is also measured using MIPs. The genetic data of the parents is used to clean the SNP data of the eight blastocysts. The cleaned genetic data is then used to allow predictions to be made concerning the potential phenotypes of the embryos. Two embryos are selected which have the most promising profile, and allowed to implant in the woman's uterus.

Another example could be a situation where a pregnant woman whose husband has a family history of Tay-Sachs disease wants to know if the fetus she is carrying is genetically susceptible, but she does not want to undergo amniocentesis, as it carries a significant risk of miscarriage. She has her blood drawn, some fetal DNA is isolated from her blood, and that DNA is analyzed using MIPs. She and her husband had already had their full genomic data analyzed previously and it is available in silico. The doctor is able to use the in silico knowledge of the parental genomes and the method disclosed herein to clean the fetal DNA data, and check if the critical gene that is responsible for Tay-Sachs disease is present in the genome of the fetus.

Another example could be a situation where a 44-year old pregnant woman is concerned that the fetus she is carrying may have Downs Syndrome. She is wary of having an intrusive technique used for pre-natal diagnosis, given a personal history of miscarriages, so she chooses to have her blood analyzed. The health care practitioner is able to find fetal cells in the maternal blood sample, and using the method disclosed herein, together with the knowledge of the woman's own genetic data, is able to diagnose for aneuploidy.

Another example could be a situation where a couple are undergoing IVF treatment, they have eggs harvested from the woman, and fertilized with sperm from the man, producing nine viable embryos. A blastocyst is harvested from each embryo, and the genomic data from the blastocysts are measured using an ILLUMINA BEAD ARRAY. Meanwhile, the diploid data is measured from tissue taken from both parents using MOLECULAR INVERSION PROBES. Haploid data from the father's sperm is measured using the same method. There were no extra eggs available from the mother, so bulk diploid tissue samples are taken from her own father and mother, and a sperm sample from her father. They are all analyzed using MIPs and the method disclosed herein is used to provide a genetic analysis for the mother's genome. That data is then used, along with the father's diploid and haploid data, to allow a highly accurate analysis of the genetic data of each of the blastocysts. Based on the phenotypic predictions, the couple chooses three embryos to implant.

Another example could be a situation where a racehorse breeder wants to increase the likelihood that the foals sired by his champion racehorse become champions themselves. He arranges for the desired mare to be impregnated by IVF, and uses genetic data from the stallion and the mare to clean the genetic data measured from the viable embryos. The cleaned embryonic genetic data allows the breeder to find relevant genotypic-phenotypic correlations and select the embryos for implantation that are most likely to produce a desirable racehorse.

Another example could be a situation where a pregnant woman wants to know whether the fetus she is carrying is predisposed towards any serious illness. The father has since passed away, and so the haploid and diploid data generated from the father's brother and the father's father are used to help clean the genetic data of the fetus, measured from fetal cells gathered during fetal blood sampling. A company contracted by the health care practitioner uses the cleaned fetal genetic data to provide a list of phenotypes that the fetus is likely to exhibit, along with the confidence of each prediction.

Another example could be an amniocentesis lab that must occasionally contend with contaminated fetal genetic data due to poor laboratory techniques. The disclosed method could be used to clean the contaminated fetal genetic data using maternal and paternal genetic data. One could imagine a situation where a laboratory is able to cut costs by relaxing sterility procedures, knowing that the disclosed method would be able to compensate for an increased rate of contaminating DNA.

Another example could be a situation in which a woman in her forties is undergoing IVF to get pregnant. She wants to screen the embryos to select the one(s) that are least likely to have a genetic illness, and are most likely to implant and carry to term. The IVF clinic she is using harvests a blastocyst from each of the viable embryos, and uses standard procedures to amplify the DNA, and measure key SNPs. The technician then uses the methods disclosed herein to screen for chromosomal imbalances, and also to find and clean the genetic data of the embryos to make predictions about the phenotypic predispositions of each embryo.

Another example could be a situation where a pregnant woman has amniocentesis, and the genetic material in the fetal cells in the blood sample are used, along with the methods described herein to screen for aneuploidy and other chromosomal abnormalities.

Miscellaneous Notes

It is important to note that the method described herein concerns the cleaning of genetic data, and as all living creatures contain genetic data, the methods are equally applicable to any human, animal, or plant that inherits chromosomes from parents. The list of animals and plants could include, but is not limited to: gorillas, chimpanzees, bonobos, cats, dogs, pandas, horses, cows, sheep, goats, pigs, cheetahs, tigers, lions, salmon, sharks, whales, camels, bison, manatees, elk, swordfish, dolphins, armadillos, wasps, cockroaches, worms, condors, eagles, sparrows, butterflies, sequoia, corn, wheat, rice, petunias, cow's vetch, sun flowers, ragweed, oak trees, chestnut trees, and head lice.

The measurement of genetic data is not a perfect process, especially when the sample of genetic material is small. The measurements often contain incorrect measurements, unclear measurements, spurious measurements, and missing measurements. The purpose of the method described herein is to detect and correct some or all of these errors. Using this method can improve the confidence with which the genetic data is known to a great extent. For example, using current techniques, uncleaned measured genetic data from DNA amplified from a single cell may contain between 20% and 50% unmeasured regions, or allele dropouts. In some cases the genetic data could contain between 1% and 99% unmeasured regions, or allele dropouts. In addition, the confidence of a given measured SNP is subject to errors as well.

In a case where the uncleaned data has an allele dropout rate of approximately 50%, it is expected that after applying the method disclosed herein the cleaned data will have correct allele calls in at least 90% of the cases, and under ideal circumstances, this could rise to 99%, or even higher.

In a case where the uncleaned data has an allele dropout rate of approximately 80%, it is expected that after applying the method disclosed herein the cleaned data will have correct allele calls in at least 95% of the cases, and under ideal circumstances, this could rise to 99.9% or even higher. In a case where the uncleaned data has an allele dropout rate of approximately 90%, it is expected that after applying the method disclosed herein the cleaned data will have correct allele calls in at least 99% of the cases, and under ideal circumstances, this could rise to 99.99% or even higher. In cases where a particular SNP measurement is made with a confidence rate close to 90%, the cleaned data is expected to have SNP calls with confidence rate of over 95%, and in ideal cases, over 99%, or even higher. In cases where a particular SNP measurement is made with a confidence rate close to 99%, the cleaned data is expected to have SNP calls with confidence rate of over 99.9%, and in ideal cases, over 99.99%, or even higher.

It is also important to note that the embryonic genetic data that can be generated by measuring the amplified DNA from one blastomere can be used for multiple purposes. For example, it can be used for detecting aneuploides, uniparental disomy, sexing the individual, as well as for making a plurality of phenotypic predictions. Currently, in IVF laboratories, due to the techniques used, it is often the case that one blastomere can only provide enough genetic material to test for one disorder, such as aneuploidy, or a particular monogenic disease. Since the method disclosed herein has the common first step of measuring a large set of SNPs from a blastomere, regardless of the type of prediction to be made, a physician or parent is not forced to choose a limited number of disorders for which to screen. Instead, the option exists to screen for as many genes and/or phenotypes as the state of medical knowledge will allow. With the disclosed method, the only advantage to identifying particular conditions to screen for prior to genotyping the blastomere is that if it is decided that certain PSNPs are especially relevant, then a more appropriate set of NSNPs which are more likely to cosegregate with the PSNPs of interest, can be selected, thus increasing the confidence of the allele calls of interest. Note that even in the case where SNPs are not personalized ahead of time, the confidences are expected to be more than adequate for the various purposes described herein.

DEFINITIONS

SNP (Single Nucleotide Polymorphism): A specific locus on a chromosome that tends to show inter-individual variation.
To call a SNP: to interrogate the identity of a particular base pair, taking into account the direct and indirect evidence.
To call an allele: to call a SNP.
To clean genetic data: to take imperfect genetic data and correct some or all of the errors, using genetic data of related individuals and the method describe herein.
Imperfect genetic data: genetic data with any of the following: allele dropouts, unclear base pair measurements, incorrect base pair measurements, spurious signals, or missing measurements.
Confidence: the statistical likelihood that the called SNP, allele, or set of alleles correctly represents the real genetic state of the individual.
Multigenic: affected by multiple genes, or alleles.
Noisy genetic data: incomplete genetic data, also called incomplete genetic data.
Uncleaned genetic data: genetic data as measured, that is, with no method has been used to correct for the presence of noise in the raw genetic data, also called crude genetic data.
Direct relation: mother, father, son, or daughter.
Chromosomal Region: a segment of a chromosome, or a full chromosome.
Parental Support: a name sometimes used for the disclosed method of cleaning genetic data.
Section of a chromosome: a section of a chromosome that can range in size from one base pair to the entire chromosome.
Section: a section of a chromosome.

What is claimed is:

1. A method for detecting the presence or absence of a chromosomal abnormality in a fetus, the method comprising:
   (a) performing a multiplex amplification for at least 70 loci in a single reaction, wherein the reaction comprises cell free DNA derived from maternal blood, and wherein the amplification comprises ligating oligonucleotides that hybridize to target sequences and amplifying the ligated oligonucleotides using PCR;
   (b) performing microarray analysis to measure an amount of genetic material at the at least 70 loci on a chromosome or chromosome segment of interest in a sample comprising DNA derived from the fetus and from the mother of the fetus, wherein the amount of genetic material at a particular locus is determined irrespective of an identity of alleles at that locus;
   (c) determining a probability of the presence and a probability of the absence of a chromosomal abnormality in the fetus by comparing the amount from step (b) to either (i) a threshold value or (ii) an expected amount for a particular copy number hypothesis;
   (d) identifying the presence or absence of a chromosomal abnormality in the fetus by selecting the probability most likely to be true; and
   (e) outputting the selected probability as an indication of whether the fetus has a chromosomal abnormality, thereby detecting the presence or absence of a chromosomal abnormality in the fetus.

2. The method of claim 1, wherein the determining is performed by comparing the amount from step (a) to an expected amount, wherein the expected amount is a mean value of genetic material at multiple loci for a reference chromosome or chromosome segment that is present in two copies.

3. The method of claim 1, wherein the at least 70 loci are loci having alleles with 100% penetrance in the population.

4. The method of claim 1, wherein the chromosome of interest or the chromosome comprising the chromosome segment of interest is selected from the group consisting of chromosome 13, chromosome 18, chromosome 21, X chromosome, Y chromosome, and combinations thereof, and wherein the chromosomal abnormality is selected from the group consisting of monosomy, uniparental disomy, trisomy, other aneuploidies, unbalanced translocations, insertions, deletions, and combinations thereof.

5. The method of claim 1, wherein the method further comprises a PCR amplification using universal amplification sequences.

6. A method for detecting aneuploidy in a fetus, the method comprising:
   (a) performing a multiplex amplification for at least 70 loci in a single reaction, wherein the reaction comprises cell free DNA derived from maternal blood, and wherein the amplification comprises ligating oligonucleotides that hybridize to target sequences and amplifying the ligated oligonucleotides using PCR;
(b) performing microarray analysis to measure an amount of genetic material at the at least 70 loci on a chromosome or chromosome segment of interest in a sample comprising DNA derived from the fetus and from the mother of the fetus, wherein the amount of genetic material at a particular locus is determined irrespective of an identity of alleles at that locus;
(c) computing, for a particular copy number hypothesis, a difference between the mean of the measured amount of genetic material at the at least 70 loci and a mean of an expected amount of genetic material at the at least 70 loci for a reference chromosome or chromosome segment that is present in two copies;
(d) determining a probability of a particular copy number hypothesis by comparing the difference for each particular copy number hypothesis; and
(e) selecting the particular copy number hypothesis with the probability most likely to be true, thereby detecting aneuploidy if the selected hypothesis is an aneuploidy hypothesis.

7. The method of claim 6, wherein the method further comprises using data from a method that makes use of allele calls at a plurality of single nucleotide polymorphism (SNP) loci to determine the probability of a particular copy number hypothesis.

8. The method of claim 6, wherein the at least 70 loci are loci having alleles with 100% penetrance in the population.

9. The method of claim 6, wherein the aneuploidy is trisomy of chromosome 21.

10. A method for detecting aneuploidy in a fetus, the method comprising:
(a) performing a multiplex amplification for at least 70 loci in a single reaction, wherein the reaction comprises cell free DNA derived from maternal blood, and wherein the amplification comprises ligating oligonucleotides that hybridize to target sequences and amplifying the ligated oligonucleotides using PCR;
(b) performing microarray analysis to measure an amount of genetic material at the at least 70 loci on a chromosome or chromosome segment of interest in a sample comprising DNA derived from the fetus and from the mother of the fetus, wherein the at least 70 loci are loci having alleles with 100% penetrance in the population;
(c) determining a probability of aneuploidy in the fetus by comparing the measured amounts of genetic material to an expected amount for a particular copy number hypothesis, wherein the expected amount is determined using a mean value of genetic material at the at least 70 loci for a reference chromosome or chromosome segment that is present in two copies; and
(d) selecting a particular copy number with a greatest probability, thereby detecting aneuploidy if the selected hypothesis is an aneuploidy hypothesis.

11. The method of claim 10, wherein the aneuploidy is trisomy of chromosome 21.

* * * * *